(12) United States Patent
Too et al.

(10) Patent No.: US 12,188,092 B2
(45) Date of Patent: Jan. 7, 2025

(54) METHOD OF DETERMINING THE RISK OF DEVELOPING BREAST CANCER BY DETECTING THE EXPRESSION LEVELS OF microRNAs (miRNAs)

(71) Applicant: AGENCY FOR SCIENCE, TECHNOLOGY AND RESEARCH, Singapore (SG)

(72) Inventors: Heng-Phon Too, Singapore (SG); Lihan Zhou, Singapore (SG); Ruiyang Zou, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/557,457

(22) PCT Filed: Mar. 9, 2016

(86) PCT No.: PCT/SG2016/050113
§ 371 (c)(1),
(2) Date: Sep. 11, 2017

(87) PCT Pub. No.: WO2016/144265
PCT Pub. Date: Sep. 15, 2016

(65) Prior Publication Data
US 2018/0230544 A1    Aug. 16, 2018

(30) Foreign Application Priority Data
Mar. 9, 2015  (SG) .......................... 10201501781W

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01); *C12Q 2600/178* (2013.01)

(58) Field of Classification Search
CPC ............ C12Q 1/6886; C12Q 2600/112; C12Q 2600/178
See application file for complete search history.

(56) References Cited

FOREIGN PATENT DOCUMENTS

WO    WO 2011/094335 A2    8/2011
WO    WO-2013190091 A1 *  12/2013
(Continued)

OTHER PUBLICATIONS

Li, S. et al. Pathology—Research and Practice 209:179-183. (Year: 2012).*

(Continued)

*Primary Examiner* — Diana B Johannsen
(74) *Attorney, Agent, or Firm* — Womble Bond Dickinson (US) LLP

(57) ABSTRACT

The present disclosure describes methods of determining the risk of developing breast cancer in a subject or determining whether a subject suffers from breast cancer. The methods can comprise detecting the expression level of microRNAs (miRNAs) hsa-miR-186-5p (SEQ ID NO: 77) and/or hsa-miR-409-3p (SEQ ID NO: 178) in a bodily fluid sample obtained from the subject and determining whether it is upregulated or downregulated as compared to a control, wherein the upregulation of hsa-miR-186-5p (SEQ ID NO: 77) and/or downregulation of hsa-miR-409-3p (SEQ ID NO: 178) indicates that the subject has breast cancer or is at risk of developing breast cancers. Also encompassed are methods of prognosis or diagnosis of breast cancer by detecting (Continued)

expression levels of combinations of miRNAs and using a score based on a panel of miRNA markers.

8 Claims, 15 Drawing Sheets

Specification includes a Sequence Listing.

(56) References Cited

FOREIGN PATENT DOCUMENTS

| | | |
|---|---|---|
| WO | WO 2014/129975 A1 | 8/2014 |
| WO | WO 2014/134144 A1 | 9/2014 |

OTHER PUBLICATIONS

PCT International Search Report for PCT Counterpart Application No. PCT/SG2016/050113, 8 pgs. (May 13, 2016).
PCT Written Opinion for PCT Counterpart Application No. PCT/SG2016/050113, 7 pgs. (May 13, 2016).
S.M. Leong, et al., "Roles of miR-186 in Circulating Tumour Cells (CTCs)-mediated Metastasis in Breast Cancer," Annals of the Academy of Medicine Singapore, vol. 42 (Supplement), No. 9, pg. S32 (Sep. 31, 2013).
Shuai Li, et al., "MicroRNA-132 is frequently down-regulated in ductal carcinoma in situ (DCIS) of breast and acts as a tumor suppressor by inhibiting cell proliferation," Pathology—Research and Practice, vol. 209, Issue 3, pp. 179-183 (Mar. 2013).
Katarina Cuk, et al., "Plasmas MicroRNA Panel for Minimally Invasive Detection of Breast Cancer," PLOS One, vol. 8, Iss. 10, pp. E76729: 1-10 (Oct. 2013).
Jie Shen, et al., "Circulating miR-148b and miR-133a as biomarkers for breast cancer detection," Oncotarget, vol. 5, No. 14, pp. 5284-5294 (Jul. 2014).
Hua Zhao, et al., "A Pilot Study of Circulating miRNAs as Potential Biomarkers of Early Stage Breast Cancer," PLOS One, vol. 5, Iss. 10, pp. e13735: 1-12 (Oct. 2010).
Aoife J. Lowery, et al., "MicroRNA signatures predict oestrogen receptor, progesterone receptor and HER2/neu receptor status in breast cancer," Breast Cancer Research, vol. 11, No. 3, pp. R27: 1-18 (May 11, 2009).
Andrew McGuire, et al., "Metastatic breast cancer: the potential of miRNA for diagnosis and treatment monitoring," Cancer Metastasis Rev, vol. 34, No. 1, pp. 145-155 (Feb. 27, 2015).
Heidi Schwarzenbach, "Circulating nucleic acids as biomarkers in breast cancer," Breast Cancer Res,, vol. 15, No. 5. pp. 211: 1-9 (Sep. 26, 2013).
Guoqiang Zhang, et al., "Mir-409-3p suppresses breast cancer cell growth and invasion by targeting Akt1," Biomedical and Biophysical Research Communications, vol. 469. Iss. 2, pp. 189-195 (Jan. 8, 2016).
Feng Zhi, et al., "A microRNA expression signature predicts meningioma recurrence," International Journal of Cancer, vol. 132, No. 1, pp. 128-136 (Jun. 26, 2012).
Ni Hou, et al., "MicroRNA profiling in human colon cancer cells furing 5-flurororacil-induced autophagy," PLOS One, vol. 9, No. 12, pp. E114779: 1-16 (Dec. 19, 2014).
U.S. Preventive Services Task Force, "Screening for Breast Cancer: U.S. Preventive Services Task Force Recommendation Statement," Annals of Internal Medicine, Nov. 2009, 11 pgs., vol. 151, No. 10, Agency for Healthcare Research and Quality.
Van Schooneveld, et al., "Expression profiling of cancerous and normal breast tissues identifies microRNAs that are differentially expressed in serum from patients with (metastatic) breast cancer and healthy volunteers," Breast Cancer Research, 2012, 16 pgs., vol. 14, BioMed Central.
Wang, et al., "Correlation and quantitation of microRNA aberrant expression in tissues and sera from patients with breast tumor," Gynecologic Oncology, 2010, pp. 586-593, vol. 119, Elsevier.
Wang, et al., "Higher expression of circulating miR-182 as a novel biomarker for breast cancer," Oncology Letters, 2013, pp. 1681-1686, vol. 6.
Waters, et al., "Impact of Tumour Epithelial Subtype on Circulating microRNAs in Breast Cancer Patients," PLoS One, Mar. 2014, 9 pgs., vol. 9, No. 3.
Wu, et al., "Next-Generation Sequencing of MicroRNAs for Breast Cancer Detection," Journal of Biomedicine and Biotechnology, 2011, 7 pgs., Hindawi Publishing Corporation.
Wu, et al., "Analysis of serum genome-wide microRNAs for breast cancer detection," Clinica Chimica Acta, 2012, pp. 1058-1065, vol. 413, Elsevier.
Wu, et al., "Advances in molecular biomarkers for gastric cancer: miRNAs as emerging novel cancer markers," Expert Reviews in Molecular Medicine, Jan. 2014, 18 pgs., vol. 16, No. 1, Cambridge University Press 2014.
Xiong, et al., "Biomarker Identification by Feature Wrappers," Genome Research, 2001, pp. 1878-1887, vol. 11, Cold Springs Harbor Laboratory.
Zeng, et al., "Down-regluation of miRNA-30a in human plasma is a novel marker for breast cancer," Med Oncol, 2013, 8 pgs., vol. 30, No. 477, Springer.
Zhao, et al., "A Pilot Study of Circulating miRNAs as Potential Biomarkers of Early Stage Breast Cancer," PLoS One, Oct. 2010, vol. 5 No. 10.
Alshatwi, et al., "Differential Expression Profile and Genetic Variants of MicroRNAs Sequences in Breast Cancer Patients," PLoS One, Feb. 2012, 6 pgs., vol. 7, No. 2, PloS One.
Asaga, et al., "Direct Serum Assay for MicroRNA-21 Concentrations in Early and Advanced Breast Cancer," Clinical Chemistry, 2011, pp. 84-91, vol. 57, No. 1.
Benjamini, et al., "Controlling the False Discovery Rate: A Practical and Powerful Approach to Multiple Testing," Journal of the Royal Statistical Society. Series B (Methodological), 1995, pp. 289-300, vol. 57, No. 1, Royal Statistical Society.
Chan, et al., "Identification of Circulating MicroRNA Signatures for Breast Cancer Detection," Clinical Cancer Research, Aug. 15, 2013, 12 pgs., vol. 19, No. 16, American Association for Cancer Research.
Cissell, et al., "Trends in MicroRNA detection," Analytical and Bioanalytical Chemistry, 2009, pp. 1109-1116, vol. 394, Springer-Verlag 2009.
Cortez, et al., "MicroRNAs in body fluids—the mix of hormones and biomarkers," Nature Reviews Clinical Oncology, Aug. 2012, pp. 467-477, vol. 8, No. 8, National Institutes of Health.
Cuk, et al., "Circulating microRNAs in plasma as early detection markers for breast cancer," International Journal of Cancer, 2013, pp. 1602-1612, vol. 132, UICC.
Cuk, et al., "Plasma MircoRNA Panel for Minimally Invasive Detection of Breast Cancer," PloS One, Oct. 2013, 10 pgs., vol. 8, No. 10.
Eichelser, et al., Deregulated Serum Concentrations of Circulating Cell-Free MicroRNAs miR-17, miR-34a, miR-155, and miR-373 in Human Breast Cancer Development and Progression, Clinical Chemistry, 2013, pp. 1489-1496, vol. 59, No. 10.
Etheridge, et al., "Extracellular microRNA: a new source of biomarker," Mutation Research, Dec. 2011, pp. 85-90, vol. 717, Nos. 1-2, National Institutes of Health.
Friedman, et al., "Most mammalian mRNAs are conserved targets of microRNAs," Genome Research, 2009, pp. 92-105, vol. 19, Cold Springs Harbor Laboratory Press.
Friel, et al., "Relevance of Circulating Tumor Cells, Extracellular Nucleic Acids and Exosomes in Breast Cancer," Breast Cancer Research and Treatment, 2010, pp. 613-625, vol. 123, No. 3.
Ganepola, et al., "Novel blood-based microRNA biomarker panel for early diagnosis of pancreatic cancer," World Journal of Gastrointestinal Oncology, Jan. 2014, pp. 22-33, vol. 6, No. 1, Baishideng Publishing Group Co., Limited.
Garcia, et al., "Global Cancer Facts & Figures 2007," 2007, 52 pgs., American Cancer Society, Atlanta, GA.
Goldhirsch, et al., "Strategies for subtypes—dealing with the diversity of breast cancer: highlights of the St Gallen International Expert

(56) References Cited

OTHER PUBLICATIONS

Consensus on the Primary Therapy of Early Breast Cancer 2011," Annals of Oncology, 2011, pp. 1736-1747, vol. 22, Oxford University Press.

Gong, et al., "Characterization of photosystem II in salt-stressed cyanobacterial Spirulina platensis cells," Biochimica et Piophysica Acta, 2008, pp. 488-495, vol. 1777, Elsevier.

Guo, "Decreased serum miR-181a is a potential new tool for breast cancer screening," International Journal of Molecular Medicine, 2012, pp. 680-686, vol. 30.

Hayashita, et al., "A Polycistronic MicroRNA Cluster, miR-17-92, Is Overexpressed in Human Lung Cancers and Enhances Cell Proliferation," Cancer Research, Nov. 2005, 6 pgs., vol. 65, No. 21, American Association for Cancer Research.

Heneghan, et al., "Systemic miRNA-195 Differentiates Breast Cancer from Other Malignancies and Is a Potential Biomarker for Detecting Noninvasive and Early Stage Disease," Cancer Diagnostics and Molecular Pathology, 2010, pp. 673-682, vol. 15, The Oncologist.

Heneghan, et al., "Circulating microRNAs as Novel Minimally Invasive Biomarkers for Breast Cancer," Annals of Surgery, Mar. 2010, 7 pgs., vol. 251, No. 3 Lippincott Williams & Wilkins.

Hindson, et al., "High-Throughput Droplet Digital PCR System for Absolute Quantitation of DNA Copy Number," Analytical Chemistry, 2011, pp. 8604-8610, vol. 83, ACS Publications.

Hu, et al., "Serum microRNA profiling and breast cancer risk: the use of miR-484/191 as endogenous controls," Carcinogenesis, 2012, pp. 828-834, vol. 33, No. 4, Advance Access.

Humphrey, et al., "Breast Cancer Screening: A Summary of the Evidence for the U.S. Preventive Services Task Force," Ann Intern Med, 2002, pp. 347-360, vol. 137, No. 5.

Jarry, et al., "The validity of circulating microRNAs in oncology: Five years of challenges and contradictions," Molecular Oncology, 2014, pp. 819-829, vol. 8, Elsevier.

Jovanovic, et al., "miRNAs and apoptosis: RNAs to die for," Oncogene, 2006, pp. 6176-6187, vol. 25, Nature Publishing Group.

Khan, et al., "miR-379 Regulates Cyclin B1 Expression and Is Decreased in Breast Cancer," PLoS One, 2013, p. 7, vol. 8, No. 7.

Kodhahl, et al., "Novel circulating microRNA signature as a potential non-invasive multi-marker test in ER-positive early-stage breast cancer: A case control study," Molecular Oncology, 2014, pp. 874-883, vol. 8, Elsevier.

Kosaka, et al., "Circulating microRNA in body fluid: a new potential biomarker for cancer diagnosis and prognosis," Cancer Sci, Oct. 2010, pp. 2087-2092, vol. 101, No. 10, Japanese Cancer Association.

Kumar, et al., "Overexpression of circulating miRNA-21 and miRNA-46a in plasma samples of breast cancer patients," Indian Journal of Biochemistry & Biophysics, Jun. 2013, pp. 210-214, vol. 50.

Lee, et al., "The C. elegans Heterochronic Gene lin-4 Encodes Small RNAs with Antisense Complementarity to lin-14," Cell, Dec. 1993, pp. 843-854, vol. 75, Cell Press.

Leidner, et al., "Dampening Enthusiasm for Circulating MicroRNA in Breast Cancer," PLoS One, Mar. 2013, 11 pgs., vol. 8, No. 3.

Li, et al., "Medthod for MicroRNA Isolation from Clinical Serum Samples," Analytical Biochemistry, Dec. 2012, pp. 69-75, vol. 431, No. 1, National Institutes of Health.

Liang, et al., The origin, function, and diagnostic potential of extracellular microRNAs in human body fluids, WIREs RNA, 2014, pp. 285-300, vol. 5, John Wiley & Sons, Ltd.

Liu, et al., "Analysis of miR-205 and miR-155 expression in the blood of breast cancer patients," Chin J Cancer Res, 2013, pp. 46-54, vol. 25, No. 1, Chinese Journal of Cancer Research.

Mabert, et al., "Cancer biomarker discovery: current status and future perspectives," International Journal of Radiation Biology, Feb. 2014, 49 pgs., Informa UK, Ltd.

Mar-Aguilar, et al., "Serum circulating microRNA profiling for identification of potential breast cancer biomarkers," Disease Markers, 2013, pp. 163-169, vol. 34, IOS Press and the authors.

Mestdagh, et al., "Evaluation of quantitative miRNA expression platforms in the microRNA quality control (miRQC) study," Nature Methods, Jun. 2014, 13 pgs., Nature America, Inc.

Molina, et al., "Tumor Markers in Breast Cancer—European Group on Tumor Markers Recommendations," Tumor Biology, 2005, pp. 281-293, vol. 26, S. Karger AG, Basel.

Nelson, et al., "Screening for Breast Cancer: Systematic Evidence Review Update for the U.S. Preventative Services Task Force," Ann Intern Med., Nov. 2009, 22 pgs., vol. 151, No. 10, National Institutes of Health.

Ng, et al., "Circulating microRNAs as Specific Biomarkers for Breast Cancer Detection," PLoS One, Jan. 2013, 10 pgs., vol. 8, No. 1.

Redova, et al., "Circulating miRNAs as new blood-based biomarkers for solid cancers," Future Oncology, 2013, pp. 387-402, vol. 9, No. 3, Future Medicine Ltd.

Roth, et al., "Circulating microRNAs as blood-based markers for patients with primary and metastatic breast cancer," Breast Cancer Research, 2012, 8 pgs., vol. 12, BioMed Central Ltd.

Saeys, et al., "A review of feature selection techniques in bioinformatics," Bioinformatics, 2007, pp. 2507-2517, vol. 23, No. 19, The Authors.

Schrauder, et al., "Circulating Micro-RNAs as Potential Blood-Based Markers for Early Stage Breast Cancer Detection," PLoS One, Jan. 2012, 9 pgs., vol. 7, No. 1.

Schwarzenbach, et al., "Diagnostic potential of PTEN-targeting miR-214 in the blood of breast cancer patients," Breast Cancer Research and Treatment, Feb. 2012, 10 pgs., Springer.

Si, et al., "Circulating microRNA-92a and microRNA-21 as novel minimally invasive biomarkers for primary breast cancer," J Cancer Res Clin Oncol, 2013, pp. 223-239, vol. 13, Springer.

Sun, et al., "Serum MicroRNA-155 as a Potential Biomarker to Track Disease in Breast Cancer," PLoS One, Oct. 2012, 8 pgs., vol. 12, No. 10.

Tong, et al., "MicroRNAs in Gastric Cancer: From Benchtop to Bedside," Dig Dis Sci, 2014, pp. 24-30, vol. 59, Springer.

Tosteson, et al., "Consequences of False-Positive Screening Mammograms," JAMA Intern Med, Jun. 2014, pp. 954-961, vol. 174, No. 6, National Institutes of Health.

Tsongalis, et al., "MicroRNA Analysis: Is It Ready for Prime Time?," Clinical Chemistry, 2013, pp. 343-347, vol. 59, No. 2.

Bagnoli et al., "Development and validation of a microRNA-based signature (MiROvaR) to predict early relapse or progression of epithelial ovarian cancer: a cohort study" The Lancet. Oncology, Jul. 8, 2016, vol. 17 No. 8, pp. 1137-1146.

Lin et al., "A serum microRNA classifier for early detection of hepatocellular carcinoma: a multicentre, retrospective, longitudinal biomarker identification study with a nested case-control study" The Lancet. Oncology, Jun. 16, 2015, vol. 16 No. 7, pp. 804-815.

Schultz et al., "MicroRNA Biomarkers in Whole Blood for Detection of Pancreatic Cancer" Journal of the American Medical Association, Jan. 22/29, 2014, vol. 311 No. 4, pp. 392-404.

Zhang et al., "Prognostic and predictive value of a microRNA signature in stage II colon cancer: a microRNA expression analysis" The Lancet. Oncology, Nov. 13, 2013, vol. 14 No. 13, pp. 1295-1306.

\* cited by examiner

SEQUENCE LISTING

```
<160> NUMBER OF SEQ ID NOS: 241

<210> SEQ ID NO 1
<211> LENGTH: 22
<212> TYPE: RNA
<213> ORGANISM: Artificial Sequence
<220> FEATURE:
<223> OTHER INFORMATION: hsa-let-7a-5p

<400> SEQUENCE: 1
ugagguagua gguuguauag uu                                              22

<210> SEQ ID NO 2
<211> LENGTH: 22
<212> TYPE: RNA
<213> ORGANISM: Artificial Sequence
<220> FEATURE:
<223> OTHER INFORMATION: hsa-let-7b-3p

<400> SEQUENCE: 2
cuauacaacc uacugccuuc cc                                              22

<210> SEQ ID NO 3
<211> LENGTH: 22
<212> TYPE: RNA
<213> ORGANISM: Artificial Sequence
<220> FEATURE:
<223> OTHER INFORMATION: hsa-let-7b-5p

<400> SEQUENCE: 3
ugagguagua gguugugugg uu                                              22

<210> SEQ ID NO 4
<211> LENGTH: 22
<212> TYPE: RNA
<213> ORGANISM: Artificial Sequence
<220> FEATURE:
<223> OTHER INFORMATION: hsa-let-7d-3p

<400> SEQUENCE: 4
```
cuauacgacc ugcugccuuu cu                                    22

<210> SEQ ID NO 5
<211> LENGTH: 22
<212> TYPE: RNA
<213> ORGANISM: Artificial Sequence
<220> FEATURE:
<223> OTHER INFORMATION: hsa-let-7d-5p

<400> SEQUENCE: 5
agagguagua gguugcauag uu                                    22

<210> SEQ ID NO 6
<211> LENGTH: 22
<212> TYPE: RNA
<213> ORGANISM: Artificial Sequence
<220> FEATURE:
<223> OTHER INFORMATION: hsa-let-7e-3p

<400> SEQUENCE: 6
cuauacggcc uccuagcuuu cc                                    22

<210> SEQ ID NO 7
<211> LENGTH: 22
<212> TYPE: RNA
<213> ORGANISM: Artificial Sequence
<220> FEATURE:
<223> OTHER INFORMATION: hsa-let-7f-1-3p

<400> SEQUENCE: 7
cuauacaauc uauugccuuc cc                                    22

<210> SEQ ID NO 8
<211> LENGTH: 22
<212> TYPE: RNA
<213> ORGANISM: Artificial Sequence
<220> FEATURE:
<223> OTHER INFORMATION: hsa-let-7f-5p

<400> SEQUENCE: 8
ugagguagua gauuguauag uu                                    22

<210> SEQ ID NO 9
<211> LENGTH: 21
<212> TYPE: RNA
<213> ORGANISM: Artificial Sequence
<220> FEATURE:
<223> OTHER INFORMATION: hsa-let-7g-3p

<400> SEQUENCE: 9
cuguacaggc cacugccuug c                                     21

<210> SEQ ID NO 10
<211> LENGTH: 22
<212> TYPE: RNA
<213> ORGANISM: Artificial Sequence
<220> FEATURE:
<223> OTHER INFORMATION: hsa-let-7g-5p

<400> SEQUENCE: 10
ugagguagua guuuguacag uu                                    22

<210> SEQ ID NO 11
<211> LENGTH: 22
<212> TYPE: RNA
<213> ORGANISM: Artificial Sequence
<220> FEATURE:
<223> OTHER INFORMATION: hsa-let-7i-5p

<400> SEQUENCE: 11
ugagguagua guuugugcug uu                                           22

<210> SEQ ID NO 12
<211> LENGTH: 22
<212> TYPE: RNA
<213> ORGANISM: Artificial Sequence
<220> FEATURE:
<223> OTHER INFORMATION: hsa-miR-1

<400> SEQUENCE: 12
uggaauguaa agaaguaugu au                                           22

<210> SEQ ID NO 13
<211> LENGTH: 21
<212> TYPE: RNA
<213> ORGANISM: Artificial Sequence
<220> FEATURE:
<223> OTHER INFORMATION: hsa-miR-101-3p

<400> SEQUENCE: 13
uacaguacug ugauaacuga a                                            21

<210> SEQ ID NO 14
<211> LENGTH: 22
<212> TYPE: RNA
<213> ORGANISM: Artificial Sequence
<220> FEATURE:
<223> OTHER INFORMATION: hsa-miR-101-5p

<400> SEQUENCE: 14
caguuaucac agugcugaug cu                                           22

<210> SEQ ID NO 15
<211> LENGTH: 23
<212> TYPE: RNA
<213> ORGANISM: Artificial Sequence
<220> FEATURE:
<223> OTHER INFORMATION: hsa-miR-103a-3p

<400> SEQUENCE: 15
agcagcauug uacagggcua uga                                          23

<210> SEQ ID NO 16
<211> LENGTH: 22
<212> TYPE: RNA
<213> ORGANISM: Artificial Sequence
<220> FEATURE:
<223> OTHER INFORMATION: hsa-miR-106b-3p

<400> SEQUENCE: 16
ccgcacugug gguacuugcu gc                                           22

<210> SEQ ID NO 17
<211> LENGTH: 21
<212> TYPE: RNA
<213> ORGANISM: Artificial Sequence
<220> FEATURE:
<223> OTHER INFORMATION: hsa-miR-106b-5p

<400> SEQUENCE: 17
uaaagugcug acagugcaga u                                            21

```
<210> SEQ ID NO 18
<211> LENGTH: 23
<212> TYPE: RNA
<213> ORGANISM: Artificial Sequence
<220> FEATURE:
<223> OTHER INFORMATION: hsa-miR-107

<400> SEQUENCE: 18
agcagcauug uacagggcua uca                                          23

<210> SEQ ID NO 19
<211> LENGTH: 22
<212> TYPE: RNA
<213> ORGANISM: Artificial Sequence
<220> FEATURE:
<223> OTHER INFORMATION: hsa-miR-10a-3p

<400> SEQUENCE: 19
caaauucgua ucuagggaa ua                                            22

<210> SEQ ID NO 20
<211> LENGTH: 23
<212> TYPE: RNA
<213> ORGANISM: Artificial Sequence
<220> FEATURE:
<223> OTHER INFORMATION: hsa-miR-10a-5p

<400> SEQUENCE: 20
uacccuguag auccgaauuu gug                                          23

<210> SEQ ID NO 21
<211> LENGTH: 23
<212> TYPE: RNA
<213> ORGANISM: Artificial Sequence
<220> FEATURE:
<223> OTHER INFORMATION: hsa-miR-10b-5p

<400> SEQUENCE: 21
uacccuguag aaccgaauuu gug                                          23

<210> SEQ ID NO 22
<211> LENGTH: 22
<212> TYPE: RNA
<213> ORGANISM: Artificial Sequence
<220> FEATURE:
<223> OTHER INFORMATION: hsa-miR-122-5p

<400> SEQUENCE: 22
uggaguguga caauggucuu ug                                           22

<210> SEQ ID NO 23
<211> LENGTH: 22
<212> TYPE: RNA
<213> ORGANISM: Artificial Sequence
<220> FEATURE:
<223> OTHER INFORMATION: hsa-miR-1226-3p

<400> SEQUENCE: 23
ucaccagccc uguguucccu ag                                           22

<210> SEQ ID NO 24
<211> LENGTH: 22
<212> TYPE: RNA
<213> ORGANISM: Artificial Sequence
<220> FEATURE:
<223> OTHER INFORMATION: hsa-miR-124-5p
```

```
<400> SEQUENCE: 24
cguguucaca gcggaccuug au                                            22

<210> SEQ ID NO 25
<211> LENGTH: 22
<212> TYPE: RNA
<213> ORGANISM: Artificial Sequence
<220> FEATURE:
<223> OTHER INFORMATION: hsa-miR-125a-3p

<400> SEQUENCE: 25
acaggugagg uucuugggag cc                                            22

<210> SEQ ID NO 26
<211> LENGTH: 22
<212> TYPE: RNA
<213> ORGANISM: Artificial Sequence
<220> FEATURE:
<223> OTHER INFORMATION: hsa-miR-125b-5p

<400> SEQUENCE: 26
ucccugagac ccuaacuugu ga                                            22

<210> SEQ ID NO 27
<211> LENGTH: 22
<212> TYPE: RNA
<213> ORGANISM: Artificial Sequence
<220> FEATURE:
<223> OTHER INFORMATION: hsa-miR-126-3p

<400> SEQUENCE: 27
ucguaccgug aguaauaaug cg                                            22

<210> SEQ ID NO 28
<211> LENGTH: 21
<212> TYPE: RNA
<213> ORGANISM: Artificial Sequence
<220> FEATURE:
<223> OTHER INFORMATION: hsa-miR-126-5p

<400> SEQUENCE: 28
cauuauuacu uuugguacgc g                                             21

<210> SEQ ID NO 29
<211> LENGTH: 22
<212> TYPE: RNA
<213> ORGANISM: Artificial Sequence
<220> FEATURE:
<223> OTHER INFORMATION: hsa-miR-127-3p

<400> SEQUENCE: 29
ucggauccgu cugagcuugg cu                                            22

<210> SEQ ID NO 30
<211> LENGTH: 21
<212> TYPE: RNA
<213> ORGANISM: Artificial Sequence
<220> FEATURE:
<223> OTHER INFORMATION: hsa-miR-128

<400> SEQUENCE: 30
ucacagugaa ccggucucuu u                                             21

<210> SEQ ID NO 31
```

```
<211> LENGTH: 17
<212> TYPE: RNA
<213> ORGANISM: Artificial Sequence
<220> FEATURE:
<223> OTHER INFORMATION: hsa-miR-1280

<400> SEQUENCE: 31
ucccaccgcu gccaccc                                                  17

<210> SEQ ID NO 32
<211> LENGTH: 22
<212> TYPE: RNA
<213> ORGANISM: Artificial Sequence
<220> FEATURE:
<223> OTHER INFORMATION: hsa-miR-1285-3p

<400> SEQUENCE: 32
ucugggcaac aaagugagac cu                                            22

<210> SEQ ID NO 33
<211> LENGTH: 24
<212> TYPE: RNA
<213> ORGANISM: Artificial Sequence
<220> FEATURE:
<223> OTHER INFORMATION: hsa-miR-1291

<400> SEQUENCE: 33
uggcccugac ugaagaccag cagu                                          24

<210> SEQ ID NO 34
<211> LENGTH: 22
<212> TYPE: RNA
<213> ORGANISM: Artificial Sequence
<220> FEATURE:
<223> OTHER INFORMATION: hsa-miR-1299

<400> SEQUENCE: 34
uucuggaauu cugugugagg ga                                            22

<210> SEQ ID NO 35
<211> LENGTH: 22
<212> TYPE: RNA
<213> ORGANISM: Artificial Sequence
<220> FEATURE:
<223> OTHER INFORMATION: hsa-miR-130a-3p

<400> SEQUENCE: 35
cagugcaaug uuaaaagggc au                                            22

<210> SEQ ID NO 36
<211> LENGTH: 22
<212> TYPE: RNA
<213> ORGANISM: Artificial Sequence
<220> FEATURE:
<223> OTHER INFORMATION: hsa-miR-130b-3p

<400> SEQUENCE: 36
cagugcaaug augaaagggc au                                            22

<210> SEQ ID NO 37
<211> LENGTH: 21
<212> TYPE: RNA
<213> ORGANISM: Artificial Sequence
<220> FEATURE:
<223> OTHER INFORMATION: hsa-miR-130b-5p

<400> SEQUENCE: 37
```

```
acucuuuccc uguugcacua c                                              21

<210> SEQ ID NO 38
<211> LENGTH: 22
<212> TYPE: RNA
<213> ORGANISM: Artificial Sequence
<220> FEATURE:
<223> OTHER INFORMATION: hsa-miR-133a

<400> SEQUENCE: 38
uuuggucccc uucaaccagc ug                                             22

<210> SEQ ID NO 39
<211> LENGTH: 23
<212> TYPE: RNA
<213> ORGANISM: Artificial Sequence
<220> FEATURE:
<223> OTHER INFORMATION: hsa-miR-135a-5p

<400> SEQUENCE: 39
uauggcuuuu uauuccuaug uga                                            23

<210> SEQ ID NO 40
<211> LENGTH: 22
<212> TYPE: RNA
<213> ORGANISM: Artificial Sequence
<220> FEATURE:
<223> OTHER INFORMATION: hsa-miR-136-3p

<400> SEQUENCE: 40
caucaucguc ucaaaugagu cu                                             22

<210> SEQ ID NO 41
<211> LENGTH: 23
<212> TYPE: RNA
<213> ORGANISM: Artificial Sequence
<220> FEATURE:
<223> OTHER INFORMATION: hsa-miR-136-5p

<400> SEQUENCE: 41
acuccauuug uuuugaugau gga                                            23

<210> SEQ ID NO 42
<211> LENGTH: 22
<212> TYPE: RNA
<213> ORGANISM: Artificial Sequence
<220> FEATURE:
<223> OTHER INFORMATION: hsa-miR-139-5p

<400> SEQUENCE: 42
ucuacagugc acgugucucc ag                                             22

<210> SEQ ID NO 43
<211> LENGTH: 21
<212> TYPE: RNA
<213> ORGANISM: Artificial Sequence
<220> FEATURE:
<223> OTHER INFORMATION: hsa-miR-140-3p

<400> SEQUENCE: 43
uaccacaggg uagaaccacg g                                              21

<210> SEQ ID NO 44
<211> LENGTH: 22
<212> TYPE: RNA
```

```
<213> ORGANISM: Artificial Sequence
<220> FEATURE:
<223> OTHER INFORMATION: hsa-miR-140-5p

<400> SEQUENCE: 44
caguguuuuu acccuauggu ag                                             22

<210> SEQ ID NO 45
<211> LENGTH: 22
<212> TYPE: RNA
<213> ORGANISM: Artificial Sequence
<220> FEATURE:
<223> OTHER INFORMATION: hsa-miR-141-3p

<400> SEQUENCE: 45
uaacacuguc ugguaaagau gg                                             22

<210> SEQ ID NO 46
<211> LENGTH: 21
<212> TYPE: RNA
<213> ORGANISM: Artificial Sequence
<220> FEATURE:
<223> OTHER INFORMATION: hsa-miR-142-5p

<400> SEQUENCE: 46
cauaaaguag aaagcacuac u                                              21

<210> SEQ ID NO 47
<211> LENGTH: 21
<212> TYPE: RNA
<213> ORGANISM: Artificial Sequence
<220> FEATURE:
<223> OTHER INFORMATION: hsa-miR-143-3p

<400> SEQUENCE: 47
ugagaugaag cacguagcu c                                               21

<210> SEQ ID NO 48
<211> LENGTH: 20
<212> TYPE: RNA
<213> ORGANISM: Artificial Sequence
<220> FEATURE:
<223> OTHER INFORMATION: hsa-miR-144-3p

<400> SEQUENCE: 48
uacaguauag augauguacu                                                20

<210> SEQ ID NO 49
<211> LENGTH: 22
<212> TYPE: RNA
<213> ORGANISM: Artificial Sequence
<220> FEATURE:
<223> OTHER INFORMATION: hsa-miR-144-5p

<400> SEQUENCE: 49
ggauaucauc auauacugua ag                                             22

<210> SEQ ID NO 50
<211> LENGTH: 23
<212> TYPE: RNA
<213> ORGANISM: Artificial Sequence
<220> FEATURE:
<223> OTHER INFORMATION: hsa-miR-145-5p

<400> SEQUENCE: 50
guccaguuuu cccaggaauc ccu                                            23
```

```
<210> SEQ ID NO 51
<211> LENGTH: 22
<212> TYPE: RNA
<213> ORGANISM: Artificial Sequence
<220> FEATURE:
<223> OTHER INFORMATION: hsa-miR-146a-5p

<400> SEQUENCE: 51
ugagaacuga auuccauggg uu                                              22

<210> SEQ ID NO 52
<211> LENGTH: 22
<212> TYPE: RNA
<213> ORGANISM: Artificial Sequence
<220> FEATURE:
<223> OTHER INFORMATION: hsa-miR-146b-5p

<400> SEQUENCE: 52
ugagaacuga auuccauagg cu                                              22

<210> SEQ ID NO 53
<211> LENGTH: 22
<212> TYPE: RNA
<213> ORGANISM: Artificial Sequence
<220> FEATURE:
<223> OTHER INFORMATION: hsa-miR-148a-3p

<400> SEQUENCE: 53
ucagugcacu acagaacuuu gu                                              22

<210> SEQ ID NO 54
<211> LENGTH: 22
<212> TYPE: RNA
<213> ORGANISM: Artificial Sequence
<220> FEATURE:
<223> OTHER INFORMATION: hsa-miR-148a-5p

<400> SEQUENCE: 54
aaaguucuga gacacuccga cu                                              22

<210> SEQ ID NO 55
<211> LENGTH: 22
<212> TYPE: RNA
<213> ORGANISM: Artificial Sequence
<220> FEATURE:
<223> OTHER INFORMATION: hsa-miR-148b-3p

<400> SEQUENCE: 55
ucagugcauc acagaacuuu gu                                              22

<210> SEQ ID NO 56
<211> LENGTH: 22
<212> TYPE: RNA
<213> ORGANISM: Artificial Sequence
<220> FEATURE:
<223> OTHER INFORMATION: hsa-miR-148b-5p

<400> SEQUENCE: 56
aaguucuguu auacacucag gc                                              22

<210> SEQ ID NO 57
<211> LENGTH: 22
<212> TYPE: RNA
<213> ORGANISM: Artificial Sequence
<220> FEATURE:
```

```
<223> OTHER INFORMATION: hsa-miR-150-3p

<400> SEQUENCE: 57
cugguacagg ccuggggac ag                                                 22

<210> SEQ ID NO 58
<211> LENGTH: 22
<212> TYPE: RNA
<213> ORGANISM: Artificial Sequence
<220> FEATURE:
<223> OTHER INFORMATION: hsa-miR-150-5p

<400> SEQUENCE: 58
ucucccaacc cuuguaccag ug                                                22

<210> SEQ ID NO 59
<211> LENGTH: 21
<212> TYPE: RNA
<213> ORGANISM: Artificial Sequence
<220> FEATURE:
<223> OTHER INFORMATION: hsa-miR-151a-3p

<400> SEQUENCE: 59
cuagacugaa gcuccuugag g                                                 21

<210> SEQ ID NO 60
<211> LENGTH: 21
<212> TYPE: RNA
<213> ORGANISM: Artificial Sequence
<220> FEATURE:
<223> OTHER INFORMATION: hsa-miR-151a-5p

<400> SEQUENCE: 60
ucgaggagcu cacagucuag u                                                 21

<210> SEQ ID NO 61
<211> LENGTH: 21
<212> TYPE: RNA
<213> ORGANISM: Artificial Sequence
<220> FEATURE:
<223> OTHER INFORMATION: hsa-miR-152

<400> SEQUENCE: 61
ucagugcaug acagaacuug g                                                 21

<210> SEQ ID NO 62
<211> LENGTH: 22
<212> TYPE: RNA
<213> ORGANISM: Artificial Sequence
<220> FEATURE:
<223> OTHER INFORMATION: hsa-miR-154-5p

<400> SEQUENCE: 62
uagguuaucc guguugccuu cg                                                22

<210> SEQ ID NO 63
<211> LENGTH: 22
<212> TYPE: RNA
<213> ORGANISM: Artificial Sequence
<220> FEATURE:
<223> OTHER INFORMATION: hsa-miR-15a-3p

<400> SEQUENCE: 63
caggccauau ugugcugccu ca                                                22
```

```
<210> SEQ ID NO 64
<211> LENGTH: 22
<212> TYPE: RNA
<213> ORGANISM: Artificial Sequence
<220> FEATURE:
<223> OTHER INFORMATION: hsa-miR-15a-5p

<400> SEQUENCE: 64
uagcagcaca uaaugguuug ug                                              22

<210> SEQ ID NO 65
<211> LENGTH: 22
<212> TYPE: RNA
<213> ORGANISM: Artificial Sequence
<220> FEATURE:
<223> OTHER INFORMATION: hsa-miR-15b-3p

<400> SEQUENCE: 65
cgaaucauua uuugcugcuc ua                                              22

<210> SEQ ID NO 66
<211> LENGTH: 22
<212> TYPE: RNA
<213> ORGANISM: Artificial Sequence
<220> FEATURE:
<223> OTHER INFORMATION: hsa-miR-15b-5p

<400> SEQUENCE: 66
uagcagcaca ucaugguuua ca                                              22

<210> SEQ ID NO 67
<211> LENGTH: 22
<212> TYPE: RNA
<213> ORGANISM: Artificial Sequence
<220> FEATURE:
<223> OTHER INFORMATION: hsa-miR-16-5p

<400> SEQUENCE: 67
uagcagcacg uaaauauugg cg                                              22

<210> SEQ ID NO 68
<211> LENGTH: 22
<212> TYPE: RNA
<213> ORGANISM: Artificial Sequence
<220> FEATURE:
<223> OTHER INFORMATION: hsa-miR-17-3p

<400> SEQUENCE: 68
acugcaguga aggcacuugu ag                                              22

<210> SEQ ID NO 69
<211> LENGTH: 23
<212> TYPE: RNA
<213> ORGANISM: Artificial Sequence
<220> FEATURE:
<223> OTHER INFORMATION: hsa-miR-17-5p

<400> SEQUENCE: 69
caaagugcuu acagugcagg uag                                             23

<210> SEQ ID NO 70
<211> LENGTH: 22
<212> TYPE: RNA
<213> ORGANISM: Artificial Sequence
<220> FEATURE:
<223> OTHER INFORMATION: hsa-miR-181a-2-3p
```

```
<400> SEQUENCE: 70
accacugacc guugacugua cc                                            22

<210> SEQ ID NO 71
<211> LENGTH: 23
<212> TYPE: RNA
<213> ORGANISM: Artificial Sequence
<220> FEATURE:
<223> OTHER INFORMATION: hsa-miR-181a-5p

<400> SEQUENCE: 71
aacauucaac gcugucggug agu                                           23

<210> SEQ ID NO 72
<211> LENGTH: 23
<212> TYPE: RNA
<213> ORGANISM: Artificial Sequence
<220> FEATURE:
<223> OTHER INFORMATION: hsa-miR-181b-5p

<400> SEQUENCE: 72
aacauucauu gcugucggug ggu                                           23

<210> SEQ ID NO 73
<211> LENGTH: 23
<212> TYPE: RNA
<213> ORGANISM: Artificial Sequence
<220> FEATURE:
<223> OTHER INFORMATION: hsa-miR-181d

<400> SEQUENCE: 73
aacauucauu guugucggug ggu                                           23

<210> SEQ ID NO 74
<211> LENGTH: 18
<212> TYPE: RNA
<213> ORGANISM: Artificial Sequence
<220> FEATURE:
<223> OTHER INFORMATION: hsa-miR-1825

<400> SEQUENCE: 74
uccagugccc uccucucc                                                 18

<210> SEQ ID NO 75
<211> LENGTH: 22
<212> TYPE: RNA
<213> ORGANISM: Artificial Sequence
<220> FEATURE:
<223> OTHER INFORMATION: hsa-miR-183-5p

<400> SEQUENCE: 75
uauggcacug guagaauuca cu                                            22

<210> SEQ ID NO 76
<211> LENGTH: 22
<212> TYPE: RNA
<213> ORGANISM: Artificial Sequence
<220> FEATURE:
<223> OTHER INFORMATION: hsa-miR-185-5p

<400> SEQUENCE: 76
uggagagaaa ggcaguuccu ga                                            22

<210> SEQ ID NO 77
<211> LENGTH: 22
```

```
<212> TYPE: RNA
<213> ORGANISM: Artificial Sequence
<220> FEATURE:
<223> OTHER INFORMATION: hsa-miR-186-5p

<400> SEQUENCE: 77
caaagaauuc uccuuuuggg cu                                              22

<210> SEQ ID NO 78
<211> LENGTH: 23
<212> TYPE: RNA
<213> ORGANISM: Artificial Sequence
<220> FEATURE:
<223> OTHER INFORMATION: hsa-miR-18a-3p

<400> SEQUENCE: 78
acugcccuaa gugcccuuc ugg                                              23

<210> SEQ ID NO 79
<211> LENGTH: 23
<212> TYPE: RNA
<213> ORGANISM: Artificial Sequence
<220> FEATURE:
<223> OTHER INFORMATION: hsa-miR-18a-5p

<400> SEQUENCE: 79
uaaggugcau cuagugcaga uag                                             23

<210> SEQ ID NO 80
<211> LENGTH: 23
<212> TYPE: RNA
<213> ORGANISM: Artificial Sequence
<220> FEATURE:
<223> OTHER INFORMATION: hsa-miR-18b-5p

<400> SEQUENCE: 80
uaaggugcau cuagugcagu uag                                             23

<210> SEQ ID NO 81
<211> LENGTH: 23
<212> TYPE: RNA
<213> ORGANISM: Artificial Sequence
<220> FEATURE:
<223> OTHER INFORMATION: hsa-miR-191-5p

<400> SEQUENCE: 81
caacggaauc ccaaaagcag cug                                             23

<210> SEQ ID NO 82
<211> LENGTH: 21
<212> TYPE: RNA
<213> ORGANISM: Artificial Sequence
<220> FEATURE:
<223> OTHER INFORMATION: hsa-miR-192-5p

<400> SEQUENCE: 82
cugaccuaug aauugacagc c                                               21

<210> SEQ ID NO 83
<211> LENGTH: 22
<212> TYPE: RNA
<213> ORGANISM: Artificial Sequence
<220> FEATURE:
<223> OTHER INFORMATION: hsa-miR-193a-5p

<400> SEQUENCE: 83
```
ugggucuuug cgggcgagau ga                    22

<210> SEQ ID NO 84
<211> LENGTH: 22
<212> TYPE: RNA
<213> ORGANISM: Artificial Sequence
<220> FEATURE:
<223> OTHER INFORMATION: hsa-miR-193b-3p

<400> SEQUENCE: 84
aacuggcccu caaagucccg cu                    22

<210> SEQ ID NO 85
<211> LENGTH: 22
<212> TYPE: RNA
<213> ORGANISM: Artificial Sequence
<220> FEATURE:
<223> OTHER INFORMATION: hsa-miR-194-5p

<400> SEQUENCE: 85
uguaacagca acuccaugug ga                    22

<210> SEQ ID NO 86
<211> LENGTH: 21
<212> TYPE: RNA
<213> ORGANISM: Artificial Sequence
<220> FEATURE:
<223> OTHER INFORMATION: hsa-miR-195-5p

<400> SEQUENCE: 86
uagcagcaca gaaauauugg c                     21

<210> SEQ ID NO 87
<211> LENGTH: 22
<212> TYPE: RNA
<213> ORGANISM: Artificial Sequence
<220> FEATURE:
<223> OTHER INFORMATION: hsa-miR-196a-5p

<400> SEQUENCE: 87
uagguaguuu cauguuguug gg                    22

<210> SEQ ID NO 88
<211> LENGTH: 22
<212> TYPE: RNA
<213> ORGANISM: Artificial Sequence
<220> FEATURE:
<223> OTHER INFORMATION: hsa-miR-196b-5p

<400> SEQUENCE: 88
uagguaguuu ccuguuguug gg                    22

<210> SEQ ID NO 89
<211> LENGTH: 22
<212> TYPE: RNA
<213> ORGANISM: Artificial Sequence
<220> FEATURE:
<223> OTHER INFORMATION: hsa-miR-197-3p

<400> SEQUENCE: 89
uucaccaccu ucuccaccca gc                    22

<210> SEQ ID NO 90
<211> LENGTH: 22
<212> TYPE: RNA
<213> ORGANISM: Artificial Sequence

```
<220> FEATURE:
<223> OTHER INFORMATION: hsa-miR-199a-3p

<400> SEQUENCE: 90
acaguagucu gcacauuggu ua                                              22

<210> SEQ ID NO 91
<211> LENGTH: 23
<212> TYPE: RNA
<213> ORGANISM: Artificial Sequence
<220> FEATURE:
<223> OTHER INFORMATION: hsa-miR-199a-5p

<400> SEQUENCE: 91
cccaguguuc agacuaccug uuc                                             23

<210> SEQ ID NO 92
<211> LENGTH: 22
<212> TYPE: RNA
<213> ORGANISM: Artificial Sequence
<220> FEATURE:
<223> OTHER INFORMATION: hsa-miR-199b-3p

<400> SEQUENCE: 92
acaguagucu gcacauuggu ua                                              22

<210> SEQ ID NO 93
<211> LENGTH: 23
<212> TYPE: RNA
<213> ORGANISM: Artificial Sequence
<220> FEATURE:
<223> OTHER INFORMATION: hsa-miR-19a-3p

<400> SEQUENCE: 93
ugugcaaauc uaugcaaaac uga                                             23

<210> SEQ ID NO 94
<211> LENGTH: 23
<212> TYPE: RNA
<213> ORGANISM: Artificial Sequence
<220> FEATURE:
<223> OTHER INFORMATION: hsa-miR-19b-3p

<400> SEQUENCE: 94
ugugcaaauc caugcaaaac uga                                             23

<210> SEQ ID NO 95
<211> LENGTH: 22
<212> TYPE: RNA
<213> ORGANISM: Artificial Sequence
<220> FEATURE:
<223> OTHER INFORMATION: hsa-miR-200b-3p

<400> SEQUENCE: 95
uaauacugcc ugguaaugau ga                                              22

<210> SEQ ID NO 96
<211> LENGTH: 23
<212> TYPE: RNA
<213> ORGANISM: Artificial Sequence
<220> FEATURE:
<223> OTHER INFORMATION: hsa-miR-200c-3p

<400> SEQUENCE: 96
uaauacugcc ggguaaugau gga                                             23
```

```
<210> SEQ ID NO 97
<211> LENGTH: 22
<212> TYPE: RNA
<213> ORGANISM: Artificial Sequence
<220> FEATURE:
<223> OTHER INFORMATION: hsa-miR-205-5p

<400> SEQUENCE: 97
uccuucauuc caccggaguc ug                                               22

<210> SEQ ID NO 98
<211> LENGTH: 22
<212> TYPE: RNA
<213> ORGANISM: Artificial Sequence
<220> FEATURE:
<223> OTHER INFORMATION: hsa-miR-206

<400> SEQUENCE: 98
uggaauguaa ggaagugugu gg                                               22

<210> SEQ ID NO 99
<211> LENGTH: 23
<212> TYPE: RNA
<213> ORGANISM: Artificial Sequence
<220> FEATURE:
<223> OTHER INFORMATION: hsa-miR-20a-5p

<400> SEQUENCE: 99
uaaagugcuu auagugcagg uag                                              23

<210> SEQ ID NO 100
<211> LENGTH: 23
<212> TYPE: RNA
<213> ORGANISM: Artificial Sequence
<220> FEATURE:
<223> OTHER INFORMATION: hsa-miR-20b-5p

<400> SEQUENCE: 100
caaagugcuc auagugcagg uag                                              23

<210> SEQ ID NO 101
<211> LENGTH: 21
<212> TYPE: RNA
<213> ORGANISM: Artificial Sequence
<220> FEATURE:
<223> OTHER INFORMATION: hsa-miR-21-3p

<400> SEQUENCE: 101
caacaccagu cgaugggcug u                                                21

<210> SEQ ID NO 102
<211> LENGTH: 22
<212> TYPE: RNA
<213> ORGANISM: Artificial Sequence
<220> FEATURE:
<223> OTHER INFORMATION: hsa-miR-214-3p

<400> SEQUENCE: 102
acagcaggca cagacaggca gu                                               22

<210> SEQ ID NO 103
<211> LENGTH: 22
<212> TYPE: RNA
<213> ORGANISM: Artificial Sequence
<220> FEATURE:
<223> OTHER INFORMATION: hsa-miR-21-5p
```

-continued

<400> SEQUENCE: 103
uagcuuauca gacugauguu ga                                        22

<210> SEQ ID NO 104
<211> LENGTH: 21
<212> TYPE: RNA
<213> ORGANISM: Artificial Sequence
<220> FEATURE:
<223> OTHER INFORMATION: hsa-miR-219-5p

<400> SEQUENCE: 104
ugauugucca aacgcaauuc u                                         21

<210> SEQ ID NO 105
<211> LENGTH: 23
<212> TYPE: RNA
<213> ORGANISM: Artificial Sequence
<220> FEATURE:
<223> OTHER INFORMATION: hsa-miR-221-3p

<400> SEQUENCE: 105
agcuacauug ucugcugggu uuc                                       23

<210> SEQ ID NO 106
<211> LENGTH: 22
<212> TYPE: RNA
<213> ORGANISM: Artificial Sequence
<220> FEATURE:
<223> OTHER INFORMATION: hsa-miR-221-5p

<400> SEQUENCE: 106
accuggcaua caauguagau uu                                        22

<210> SEQ ID NO 107
<211> LENGTH: 21
<212> TYPE: RNA
<213> ORGANISM: Artificial Sequence
<220> FEATURE:
<223> OTHER INFORMATION: hsa-miR-222-3p

<400> SEQUENCE: 107
agcuacaucu ggcuacuggg u                                         21

<210> SEQ ID NO 108
<211> LENGTH: 22
<212> TYPE: RNA
<213> ORGANISM: Artificial Sequence
<220> FEATURE:
<223> OTHER INFORMATION: hsa-miR-223-3p

<400> SEQUENCE: 108
ugucaguuug ucaaauaccc ca                                        22

<210> SEQ ID NO 109
<211> LENGTH: 22
<212> TYPE: RNA
<213> ORGANISM: Artificial Sequence
<220> FEATURE:
<223> OTHER INFORMATION: hsa-miR-22-3p

<400> SEQUENCE: 109
aagcugccag uugaagaacu gu                                        22

<210> SEQ ID NO 110

```
<211> LENGTH: 21
<212> TYPE: RNA
<213> ORGANISM: Artificial Sequence
<220> FEATURE:
<223> OTHER INFORMATION: hsa-miR-224-5p

<400> SEQUENCE: 110
caagucacua gugguuccgu u                                              21

<210> SEQ ID NO 111
<211> LENGTH: 22
<212> TYPE: RNA
<213> ORGANISM: Artificial Sequence
<220> FEATURE:
<223> OTHER INFORMATION: hsa-miR-2355-3p

<400> SEQUENCE: 111
auuguccuug cuguuuggag au                                             22

<210> SEQ ID NO 112
<211> LENGTH: 21
<212> TYPE: RNA
<213> ORGANISM: Artificial Sequence
<220> FEATURE:
<223> OTHER INFORMATION: hsa-miR-23a-3p

<400> SEQUENCE: 112
aucacauugc cagggauuuc c                                              21

<210> SEQ ID NO 113
<211> LENGTH: 22
<212> TYPE: RNA
<213> ORGANISM: Artificial Sequence
<220> FEATURE:
<223> OTHER INFORMATION: hsa-miR-23a-5p

<400> SEQUENCE: 113 ggggguuccug gggaugggau uu                                            22

<210> SEQ ID NO 114
<211> LENGTH: 21
<212> TYPE: RNA
<213> ORGANISM: Artificial Sequence
<220> FEATURE:
<223> OTHER INFORMATION: hsa-miR-23b-3p

<400> SEQUENCE: 114
aucacauugc cagggauuac c                                              21

<210> SEQ ID NO 115
<211> LENGTH: 22
<212> TYPE: RNA
<213> ORGANISM: Artificial Sequence
<220> FEATURE:
<223> OTHER INFORMATION: hsa-miR-23c

<400> SEQUENCE: 115
aucacauugc cagugauuac cc                                             22

<210> SEQ ID NO 116
<211> LENGTH: 22
<212> TYPE: RNA
<213> ORGANISM: Artificial Sequence
<220> FEATURE:
<223> OTHER INFORMATION: hsa-miR-24-3p

<400> SEQUENCE: 116
```
uggcucaguu cagcaggaac ag                                              22

<210> SEQ ID NO 117
<211> LENGTH: 22
<212> TYPE: RNA
<213> ORGANISM: Artificial Sequence
<220> FEATURE:
<223> OTHER INFORMATION: hsa-miR-25-3p

<400> SEQUENCE: 117
cauugcacuu gucucggucu ga                                              22

<210> SEQ ID NO 118
<211> LENGTH: 22
<212> TYPE: RNA
<213> ORGANISM: Artificial Sequence
<220> FEATURE:
<223> OTHER INFORMATION: hsa-miR-26a-5p

<400> SEQUENCE: 118
uucaaguaau ccaggauagg cu                                              22

<210> SEQ ID NO 119
<211> LENGTH: 22
<212> TYPE: RNA
<213> ORGANISM: Artificial Sequence
<220> FEATURE:
<223> OTHER INFORMATION: hsa-miR-26b-3p

<400> SEQUENCE: 119
ccuguucucc auuacuuggc uc                                              22

<210> SEQ ID NO 120
<211> LENGTH: 21
<212> TYPE: RNA
<213> ORGANISM: Artificial Sequence
<220> FEATURE:
<223> OTHER INFORMATION: hsa-miR-26b-5p

<400> SEQUENCE: 120
uucaaguaau ucaggauagg u                                               21

<210> SEQ ID NO 121
<211> LENGTH: 21
<212> TYPE: RNA
<213> ORGANISM: Artificial Sequence
<220> FEATURE:
<223> OTHER INFORMATION: hsa-miR-27a-3p

<400> SEQUENCE: 121
uucacagugg cuaaguuccg c                                               21

<210> SEQ ID NO 122
<211> LENGTH: 22
<212> TYPE: RNA
<213> ORGANISM: Artificial Sequence
<220> FEATURE:
<223> OTHER INFORMATION: hsa-miR-27a-5p

<400> SEQUENCE: 122
agggcuuagc ugcuugugag ca                                              22

<210> SEQ ID NO 123
<211> LENGTH: 21
<212> TYPE: RNA

```
<213> ORGANISM: Artificial Sequence
<220> FEATURE:
<223> OTHER INFORMATION: hsa-miR-27b-3p

<400> SEQUENCE: 123
uucacagugg cuaaguucug c                                              21

<210> SEQ ID NO 124
<211> LENGTH: 22
<212> TYPE: RNA
<213> ORGANISM: Artificial Sequence
<220> FEATURE:
<223> OTHER INFORMATION: hsa-miR-28-3p

<400> SEQUENCE: 124
cacuagauug ugagcccug ga                                              22

<210> SEQ ID NO 125
<211> LENGTH: 22
<212> TYPE: RNA
<213> ORGANISM: Artificial Sequence
<220> FEATURE:
<223> OTHER INFORMATION: hsa-miR-28-5p

<400> SEQUENCE: 125
aaggagcuca cagucuauug ag                                             22

<210> SEQ ID NO 126
<211> LENGTH: 22
<212> TYPE: RNA
<213> ORGANISM: Artificial Sequence
<220> FEATURE:
<223> OTHER INFORMATION: hsa-miR-299-3p

<400> SEQUENCE: 126
uaugugggau gguaaaccgc uu                                             22

<210> SEQ ID NO 127
<211> LENGTH: 22
<212> TYPE: RNA
<213> ORGANISM: Artificial Sequence
<220> FEATURE:
<223> OTHER INFORMATION: hsa-miR-29a-3p

<400> SEQUENCE: 127
uagcaccauc ugaaaucggu ua                                             22

<210> SEQ ID NO 128
<211> LENGTH: 22
<212> TYPE: RNA
<213> ORGANISM: Artificial Sequence
<220> FEATURE:
<223> OTHER INFORMATION: hsa-miR-29b-2-5p

<400> SEQUENCE: 128
cugguuucac augguggcuu ag                                             22

<210> SEQ ID NO 129
<211> LENGTH: 23
<212> TYPE: RNA
<213> ORGANISM: Artificial Sequence
<220> FEATURE:
<223> OTHER INFORMATION: hsa-miR-29b-3p

<400> SEQUENCE: 129
uagcaccauu ugaaaucagu guu                                            23
```

```
<210> SEQ ID NO 130
<211> LENGTH: 22
<212> TYPE: RNA
<213> ORGANISM: Artificial Sequence
<220> FEATURE:
<223> OTHER INFORMATION: hsa-miR-29c-3p

<400> SEQUENCE: 130
uagcaccauu ugaaaucggu ua                                              22

<210> SEQ ID NO 131
<211> LENGTH: 22
<212> TYPE: RNA
<213> ORGANISM: Artificial Sequence
<220> FEATURE:
<223> OTHER INFORMATION: hsa-miR-29c-5p

<400> SEQUENCE: 131
ugaccgauuu cuccuggugu uc                                              22

<210> SEQ ID NO 132
<211> LENGTH: 23
<212> TYPE: RNA
<213> ORGANISM: Artificial Sequence
<220> FEATURE:
<223> OTHER INFORMATION: hsa-miR-301a-3p

<400> SEQUENCE: 132
cagugcaaua guauugucaa agc                                             23

<210> SEQ ID NO 133
<211> LENGTH: 22
<212> TYPE: RNA
<213> ORGANISM: Artificial Sequence
<220> FEATURE:
<223> OTHER INFORMATION: hsa-miR-30a-5p

<400> SEQUENCE: 133
uguaaacauc cucgacugga ag                                              22

<210> SEQ ID NO 134
<211> LENGTH: 22
<212> TYPE: RNA
<213> ORGANISM: Artificial Sequence
<220> FEATURE:
<223> OTHER INFORMATION: hsa-miR-30b-5p

<400> SEQUENCE: 134
uguaaacauc cuacacucag cu                                              22

<210> SEQ ID NO 135
<211> LENGTH: 23
<212> TYPE: RNA
<213> ORGANISM: Artificial Sequence
<220> FEATURE:
<223> OTHER INFORMATION: hsa-miR-30c-5p

<400> SEQUENCE: 135
uguaaacauc cuacacucuc agc                                             23

<210> SEQ ID NO 136
<211> LENGTH: 22
<212> TYPE: RNA
<213> ORGANISM: Artificial Sequence
<220> FEATURE:
```

<223> OTHER INFORMATION: hsa-miR-30d-3p

<400> SEQUENCE: 136
cuuucaguca gauguuugcu gc				22

<210> SEQ ID NO 137
<211> LENGTH: 22
<212> TYPE: RNA
<213> ORGANISM: Artificial Sequence
<220> FEATURE:
<223> OTHER INFORMATION: hsa-miR-30d-5p

<400> SEQUENCE: 137
uguaaacauc cccgacugga ag				22

<210> SEQ ID NO 138
<211> LENGTH: 22
<212> TYPE: RNA
<213> ORGANISM: Artificial Sequence
<220> FEATURE:
<223> OTHER INFORMATION: hsa-miR-30e-3p

<400> SEQUENCE: 138
cuuucagucg gauguuuaca gc				22

<210> SEQ ID NO 139
<211> LENGTH: 22
<212> TYPE: RNA
<213> ORGANISM: Artificial Sequence
<220> FEATURE:
<223> OTHER INFORMATION: hsa-miR-30e-5p

<400> SEQUENCE: 139
uguaaacauc cuugacugga ag				22

<210> SEQ ID NO 140
<211> LENGTH: 22
<212> TYPE: RNA
<213> ORGANISM: Artificial Sequence
<220> FEATURE:
<223> OTHER INFORMATION: hsa-miR-320a

<400> SEQUENCE: 140
aaaagcuggg uugagagggc ga				22

<210> SEQ ID NO 141
<211> LENGTH: 22
<212> TYPE: RNA
<213> ORGANISM: Artificial Sequence
<220> FEATURE:
<223> OTHER INFORMATION: hsa-miR-320b

<400> SEQUENCE: 141
aaaagcuggg uugagagggc aa				22

<210> SEQ ID NO 142
<211> LENGTH: 20
<212> TYPE: RNA
<213> ORGANISM: Artificial Sequence
<220> FEATURE:
<223> OTHER INFORMATION: hsa-miR-320c

<400> SEQUENCE: 142
aaaagcuggg uugagagggu				20

```
<210> SEQ ID NO 143
<211> LENGTH: 19
<212> TYPE: RNA
<213> ORGANISM: Artificial Sequence
<220> FEATURE:
<223> OTHER INFORMATION: hsa-miR-320d

<400> SEQUENCE: 143
aaaagcuggg uugagagga                                                    19

<210> SEQ ID NO 144
<211> LENGTH: 18
<212> TYPE: RNA
<213> ORGANISM: Artificial Sequence
<220> FEATURE:
<223> OTHER INFORMATION: hsa-miR-320e

<400> SEQUENCE: 144
aaagcugggu ugagaagg                                                     18

<210> SEQ ID NO 145
<211> LENGTH: 20
<212> TYPE: RNA
<213> ORGANISM: Artificial Sequence
<220> FEATURE:
<223> OTHER INFORMATION: hsa-miR-324-3p

<400> SEQUENCE: 145
acugccccag gugcugcugg                                                   20

<210> SEQ ID NO 146
<211> LENGTH: 23
<212> TYPE: RNA
<213> ORGANISM: Artificial Sequence
<220> FEATURE:
<223> OTHER INFORMATION: hsa-miR-324-5p

<400> SEQUENCE: 146
cgcauccccu agggcauugg ugu                                               23

<210> SEQ ID NO 147
<211> LENGTH: 22
<212> TYPE: RNA
<213> ORGANISM: Artificial Sequence
<220> FEATURE:
<223> OTHER INFORMATION: hsa-miR-32-5p

<400> SEQUENCE: 147
uauugcacau uacuaaguug ca                                                22

<210> SEQ ID NO 148
<211> LENGTH: 20
<212> TYPE: RNA
<213> ORGANISM: Artificial Sequence
<220> FEATURE:
<223> OTHER INFORMATION: hsa-miR-326

<400> SEQUENCE: 148
ccucugggcc cuuccuccag                                                   20

<210> SEQ ID NO 149
<211> LENGTH: 22
<212> TYPE: RNA
<213> ORGANISM: Artificial Sequence
<220> FEATURE:
<223> OTHER INFORMATION: hsa-miR-328
```

<400> SEQUENCE: 149
cuggcccucu cugcccuucc gu                            22

<210> SEQ ID NO 150
<211> LENGTH: 23
<212> TYPE: RNA
<213> ORGANISM: Artificial Sequence
<220> FEATURE:
<223> OTHER INFORMATION: hsa-miR-330-3p

<400> SEQUENCE: 150
gcaaagcaca cggccugcag aga                           23

<210> SEQ ID NO 151
<211> LENGTH: 22
<212> TYPE: RNA
<213> ORGANISM: Artificial Sequence
<220> FEATURE:
<223> OTHER INFORMATION: hsa-miR-331-5p

<400> SEQUENCE: 151
cuagguaugg ucccagggau cc                            22

<210> SEQ ID NO 152
<211> LENGTH: 22
<212> TYPE: RNA
<213> ORGANISM: Artificial Sequence
<220> FEATURE:
<223> OTHER INFORMATION: hsa-miR-335-3p

<400> SEQUENCE: 152
uuuuucauua uugcuccuga cc                            22

<210> SEQ ID NO 153
<211> LENGTH: 23
<212> TYPE: RNA
<213> ORGANISM: Artificial Sequence
<220> FEATURE:
<223> OTHER INFORMATION: hsa-miR-335-5p

<400> SEQUENCE: 153
ucaagagcaa uaacgaaaaa ugu                           23

<210> SEQ ID NO 154
<211> LENGTH: 22
<212> TYPE: RNA
<213> ORGANISM: Artificial Sequence
<220> FEATURE:
<223> OTHER INFORMATION: hsa-miR-337-3p

<400> SEQUENCE: 154
cuccuauaug augccuuucu uc                            22

<210> SEQ ID NO 155
<211> LENGTH: 21
<212> TYPE: RNA
<213> ORGANISM: Artificial Sequence
<220> FEATURE:
<223> OTHER INFORMATION: hsa-miR-337-5p

<400> SEQUENCE: 155
gaacggcuuc auacaggagu u                             21

<210> SEQ ID NO 156
<211> LENGTH: 22

```
<212> TYPE: RNA
<213> ORGANISM: Artificial Sequence
<220> FEATURE:
<223> OTHER INFORMATION: hsa-miR-338-5p

<400> SEQUENCE: 156
aacaauaucc uggugcugag ug                                          22

<210> SEQ ID NO 157
<211> LENGTH: 23
<212> TYPE: RNA
<213> ORGANISM: Artificial Sequence
<220> FEATURE:
<223> OTHER INFORMATION: hsa-miR-339-3p

<400> SEQUENCE: 157
ugagcgccuc gacgacagag ccg                                         23

<210> SEQ ID NO 158
<211> LENGTH: 23
<212> TYPE: RNA
<213> ORGANISM: Artificial Sequence
<220> FEATURE:
<223> OTHER INFORMATION: hsa-miR-339-5p

<400> SEQUENCE: 158
ucccuguccu ccaggagcuc acg                                         23

<210> SEQ ID NO 159
<211> LENGTH: 22
<212> TYPE: RNA
<213> ORGANISM: Artificial Sequence
<220> FEATURE:
<223> OTHER INFORMATION: hsa-miR-340-5p

<400> SEQUENCE: 159
uuauaaagca augagacuga uu                                          22

<210> SEQ ID NO 160
<211> LENGTH: 21
<212> TYPE: RNA
<213> ORGANISM: Artificial Sequence
<220> FEATURE:
<223> OTHER INFORMATION: hsa-miR-342-5p

<400> SEQUENCE: 160
aggggugcua ucugugauug a                                           21

<210> SEQ ID NO 161
<211> LENGTH: 22
<212> TYPE: RNA
<213> ORGANISM: Artificial Sequence
<220> FEATURE:
<223> OTHER INFORMATION: hsa-miR-34a-5p

<400> SEQUENCE: 161
uggcaguguc uuagcugguu gu                                          22

<210> SEQ ID NO 162
<211> LENGTH: 23
<212> TYPE: RNA
<213> ORGANISM: Artificial Sequence
<220> FEATURE:
<223> OTHER INFORMATION: hsa-miR-34b-5p

<400> SEQUENCE: 162
```

```
uaggcagugu cauuagcuga uug                                             23

<210> SEQ ID NO 163
<211> LENGTH: 22
<212> TYPE: RNA
<213> ORGANISM: Artificial Sequence
<220> FEATURE:
<223> OTHER INFORMATION: hsa-miR-361-5p

<400> SEQUENCE: 163
uuaucagaau cuccaggggu ac                                              22

<210> SEQ ID NO 164
<211> LENGTH: 22
<212> TYPE: RNA
<213> ORGANISM: Artificial Sequence
<220> FEATURE:
<223> OTHER INFORMATION: hsa-miR-362-3p

<400> SEQUENCE: 164
aacacaccua uucaaggauu ca                                              22

<210> SEQ ID NO 165
<211> LENGTH: 24
<212> TYPE: RNA
<213> ORGANISM: Artificial Sequence
<220> FEATURE:
<223> OTHER INFORMATION: hsa-miR-362-5p

<400> SEQUENCE: 165
aauccuugga accuaggugu gagu                                            24

<210> SEQ ID NO 166
<211> LENGTH: 22
<212> TYPE: RNA
<213> ORGANISM: Artificial Sequence
<220> FEATURE:
<223> OTHER INFORMATION: hsa-miR-363-3p

<400> SEQUENCE: 166
aauugcacgg uauccaucug ua                                              22

<210> SEQ ID NO 167
<211> LENGTH: 22
<212> TYPE: RNA
<213> ORGANISM: Artificial Sequence
<220> FEATURE:
<223> OTHER INFORMATION: hsa-miR-365a-3p

<400> SEQUENCE: 167
uaaugcsccu aaaaauccuu au                                              22

<210> SEQ ID NO 168
<211> LENGTH: 22
<212> TYPE: RNA
<213> ORGANISM: Artificial Sequence
<220> FEATURE:
<223> OTHER INFORMATION: hsa-miR-369-5p

<400> SEQUENCE: 168
agaucgaccg uguuauauuc gc                                              22

<210> SEQ ID NO 169
<211> LENGTH: 22
<212> TYPE: RNA
<213> ORGANISM: Artificial Sequence
```

```
<220> FEATURE:
<223> OTHER INFORMATION: hsa-miR-370

<400> SEQUENCE: 169
gccugcuggg guggaaccug gu                                           22

<210> SEQ ID NO 170
<211> LENGTH: 22
<212> TYPE: RNA
<213> ORGANISM: Artificial Sequence
<220> FEATURE:
<223> OTHER INFORMATION: hsa-miR-374a-3p

<400> SEQUENCE: 170
cuuaucagau uguauuguaa uu                                           22

<210> SEQ ID NO 171
<211> LENGTH: 22
<212> TYPE: RNA
<213> ORGANISM: Artificial Sequence
<220> FEATURE:
<223> OTHER INFORMATION: hsa-miR-374a-5p

<400> SEQUENCE: 171
uuauaauaca accugauaag ug                                           22

<210> SEQ ID NO 172
<211> LENGTH: 22
<212> TYPE: RNA
<213> ORGANISM: Artificial Sequence
<220> FEATURE:
<223> OTHER INFORMATION: hsa-miR-374b-5p

<400> SEQUENCE: 172
auauaauaca accugcuaag ug                                           22

<210> SEQ ID NO 173
<211> LENGTH: 22
<212> TYPE: RNA
<213> ORGANISM: Artificial Sequence
<220> FEATURE:
<223> OTHER INFORMATION: hsa-miR-375

<400> SEQUENCE: 173
uuuguucguu cggcucgcgu ga                                           22

<210> SEQ ID NO 174
<211> LENGTH: 22
<212> TYPE: RNA
<213> ORGANISM: Artificial Sequence
<220> FEATURE:
<223> OTHER INFORMATION: hsa-miR-376a-5p

<400> SEQUENCE: 174
guagauucuc cuucuaugag ua                                           22

<210> SEQ ID NO 175
<211> LENGTH: 21
<212> TYPE: RNA
<213> ORGANISM: Artificial Sequence
<220> FEATURE:
<223> OTHER INFORMATION: hsa-miR-378a-3p

<400> SEQUENCE: 175
acuggacuug gagucagaag g                                            21
```

```
<210> SEQ ID NO 176
<211> LENGTH: 22
<212> TYPE: RNA
<213> ORGANISM: Artificial Sequence
<220> FEATURE:
<223> OTHER INFORMATION: hsa-miR-378a-5p

<400> SEQUENCE: 176
cuccugacuc cagguccugu gu                                                  22

<210> SEQ ID NO 177
<211> LENGTH: 22
<212> TYPE: RNA
<213> ORGANISM: Artificial Sequence
<220> FEATURE:
<223> OTHER INFORMATION: hsa-miR-382-5p

<400> SEQUENCE: 177
gaaguuguuc gugguggauu cg                                                  22

<210> SEQ ID NO 178
<211> LENGTH: 22
<212> TYPE: RNA
<213> ORGANISM: Artificial Sequence
<220> FEATURE:
<223> OTHER INFORMATION: hsa-miR-409-3p

<400> SEQUENCE: 178
gaauguugcu cggugaaccc cu                                                  22

<210> SEQ ID NO 179
<211> LENGTH: 22
<212> TYPE: RNA
<213> ORGANISM: Artificial Sequence
<220> FEATURE:
<223> OTHER INFORMATION: hsa-miR-411-3p

<400> SEQUENCE: 179
uauguaacac gguccacuaa cc                                                  22

<210> SEQ ID NO 180
<211> LENGTH: 21
<212> TYPE: RNA
<213> ORGANISM: Artificial Sequence
<220> FEATURE:
<223> OTHER INFORMATION: hsa-miR-411-5p

<400> SEQUENCE: 180
uaguagaccg uauagcguac g                                                   21

<210> SEQ ID NO 181
<211> LENGTH: 23
<212> TYPE: RNA
<213> ORGANISM: Artificial Sequence
<220> FEATURE:
<223> OTHER INFORMATION: hsa-miR-423-5p

<400> SEQUENCE: 181
ugaggggcag agagcgagac uuu                                                 23

<210> SEQ ID NO 182
<211> LENGTH: 22
<212> TYPE: RNA
<213> ORGANISM: Artificial Sequence
<220> FEATURE:
<223> OTHER INFORMATION: hsa-miR-424-5p
```

```
<400> SEQUENCE: 182
cagcagcaau ucauguuuug aa                                              22

<210> SEQ ID NO 183
<211> LENGTH: 22
<212> TYPE: RNA
<213> ORGANISM: Artificial Sequence
<220> FEATURE:
<223> OTHER INFORMATION: hsa-miR-425-3p

<400> SEQUENCE: 183
aucgggaaug ucguguccgc cc                                              22

<210> SEQ ID NO 184
<211> LENGTH: 23
<212> TYPE: RNA
<213> ORGANISM: Artificial Sequence
<220> FEATURE:
<223> OTHER INFORMATION: hsa-miR-425-5p

<400> SEQUENCE: 184
aaugacacga ucacucccgu uga                                             23

<210> SEQ ID NO 185
<211> LENGTH: 22
<212> TYPE: RNA
<213> ORGANISM: Artificial Sequence
<220> FEATURE:
<223> OTHER INFORMATION: hsa-miR-429

<400> SEQUENCE: 185
uaauacuguc ugguaaaacc gu                                              22

<210> SEQ ID NO 186
<211> LENGTH: 17
<212> TYPE: RNA
<213> ORGANISM: Artificial Sequence
<220> FEATURE:
<223> OTHER INFORMATION: hsa-miR-4306

<400> SEQUENCE: 186
uggagagaaa ggcagua                                                    17

<210> SEQ ID NO 187
<211> LENGTH: 21
<212> TYPE: RNA
<213> ORGANISM: Artificial Sequence
<220> FEATURE:
<223> OTHER INFORMATION: hsa-miR-431-5p

<400> SEQUENCE: 187
ugucuugcag gccgucaugc a                                               21

<210> SEQ ID NO 188
<211> LENGTH: 23
<212> TYPE: RNA
<213> ORGANISM: Artificial Sequence
<220> FEATURE:
<223> OTHER INFORMATION: hsa-miR-432-5p

<400> SEQUENCE: 188
ucuuggagua ggucauuggg ugg                                             23

<210> SEQ ID NO 189
```

```
<211> LENGTH: 22
<212> TYPE: RNA
<213> ORGANISM: Artificial Sequence
<220> FEATURE:
<223> OTHER INFORMATION: hsa-miR-450a-5p

<400> SEQUENCE: 189
uuuugcgaug uguuccuaau au                                              22

<210> SEQ ID NO 190
<211> LENGTH: 22
<212> TYPE: RNA
<213> ORGANISM: Artificial Sequence
<220> FEATURE:
<223> OTHER INFORMATION: hsa-miR-451a

<400> SEQUENCE: 190
aaaccguuac cauuacugag uu                                              22

<210> SEQ ID NO 191
<211> LENGTH: 22
<212> TYPE: RNA
<213> ORGANISM: Artificial Sequence
<220> FEATURE:
<223> OTHER INFORMATION: hsa-miR-452-5p

<400> SEQUENCE: 191
aacuguuugc agaggaaacu ga                                              22

<210> SEQ ID NO 192
<211> LENGTH: 23
<212> TYPE: RNA
<213> ORGANISM: Artificial Sequence
<220> FEATURE:
<223> OTHER INFORMATION: hsa-miR-454-3p

<400> SEQUENCE: 192
uagugcaaua uugcuuauag ggu                                             23

<210> SEQ ID NO 193
<211> LENGTH: 22
<212> TYPE: RNA
<213> ORGANISM: Artificial Sequence
<220> FEATURE:
<223> OTHER INFORMATION: hsa-miR-454-5p

<400> SEQUENCE: 193
acccuaucaa uauugcucu gc                                               22

<210> SEQ ID NO 194
<211> LENGTH: 21
<212> TYPE: RNA
<213> ORGANISM: Artificial Sequence
<220> FEATURE:
<223> OTHER INFORMATION: hsa-miR-4732-3p

<400> SEQUENCE: 194
gcccugaccu guccuguucu g                                               21

<210> SEQ ID NO 195
<211> LENGTH: 21
<212> TYPE: RNA
<213> ORGANISM: Artificial Sequence
<220> FEATURE:
<223> OTHER INFORMATION: hsa-miR-483-3p

<400> SEQUENCE: 195
```

-continued

```
ucacuccucu ccucccgucu u                                              21

<210> SEQ ID NO 196
<211> LENGTH: 22
<212> TYPE: RNA
<213> ORGANISM: Artificial Sequence
<220> FEATURE:
<223> OTHER INFORMATION: hsa-miR-483-5p

<400> SEQUENCE: 196
aagacgggag gaaagaaggg ag                                             22

<210> SEQ ID NO 197
<211> LENGTH: 22
<212> TYPE: RNA
<213> ORGANISM: Artificial Sequence
<220> FEATURE:
<223> OTHER INFORMATION: hsa-miR-484

<400> SEQUENCE: 197
ucaggcucag uccccucccg au                                             22

<210> SEQ ID NO 198
<211> LENGTH: 22
<212> TYPE: RNA
<213> ORGANISM: Artificial Sequence
<220> FEATURE:
<223> OTHER INFORMATION: hsa-miR-485-3p

<400> SEQUENCE: 198
gucauacacg gcucuccucu cu                                             22

<210> SEQ ID NO 199
<211> LENGTH: 22
<212> TYPE: RNA
<213> ORGANISM: Artificial Sequence
<220> FEATURE:
<223> OTHER INFORMATION: hsa-miR-485-5p

<400> SEQUENCE: 199
agaggcuggc cgugaugaau uc                                             22

<210> SEQ ID NO 200
<211> LENGTH: 22
<212> TYPE: RNA
<213> ORGANISM: Artificial Sequence
<220> FEATURE:
<223> OTHER INFORMATION: hsa-miR-486-5p

<400> SEQUENCE: 200
uccuguacug agcugccccg ag                                             22

<210> SEQ ID NO 201
<211> LENGTH: 22
<212> TYPE: RNA
<213> ORGANISM: Artificial Sequence
<220> FEATURE:
<223> OTHER INFORMATION: hsa-miR-487b

<400> SEQUENCE: 201
aaucguacag ggucauccac uu                                             22

<210> SEQ ID NO 202
<211> LENGTH: 22
<212> TYPE: RNA
```

<213> ORGANISM: Artificial Sequence
<220> FEATURE:
<223> OTHER INFORMATION: hsa-miR-491-5p

<400> SEQUENCE: 202
aguggggaac ccuuccauga gg                              22

<210> SEQ ID NO 203
<211> LENGTH: 22
<212> TYPE: RNA
<213> ORGANISM: Artificial Sequence
<220> FEATURE:
<223> OTHER INFORMATION: hsa-miR-493-5p

<400> SEQUENCE: 203
uuguacaugg uaggcuuuca uu                              22

<210> SEQ ID NO 204
<211> LENGTH: 21
<212> TYPE: RNA
<213> ORGANISM: Artificial Sequence
<220> FEATURE:
<223> OTHER INFORMATION: hsa-miR-497-5p

<400> SEQUENCE: 204
cagcagcaca cugugguuug u                               21

<210> SEQ ID NO 205
<211> LENGTH: 21
<212> TYPE: RNA
<213> ORGANISM: Artificial Sequence
<220> FEATURE:
<223> OTHER INFORMATION: hsa-miR-499a-5p

<400> SEQUENCE: 205
uuaagacuug cagugauguu u                               21

<210> SEQ ID NO 206
<211> LENGTH: 22
<212> TYPE: RNA
<213> ORGANISM: Artificial Sequence
<220> FEATURE:
<223> OTHER INFORMATION: hsa-miR-500a-3p

<400> SEQUENCE: 206
augcaccugg gcaaggauuc ug                              22

<210> SEQ ID NO 207
<211> LENGTH: 23
<212> TYPE: RNA
<213> ORGANISM: Artificial Sequence
<220> FEATURE:
<223> OTHER INFORMATION: hsa-miR-500a-5p

<400> SEQUENCE: 207
uaauccuugc uaccugggug aga                             23

<210> SEQ ID NO 208
<211> LENGTH: 22
<212> TYPE: RNA
<213> ORGANISM: Artificial Sequence
<220> FEATURE:
<223> OTHER INFORMATION: hsa-miR-501-5p

<400> SEQUENCE: 208
aauccuuugu cccuggguga ga                              22

```
<210> SEQ ID NO 209
<211> LENGTH: 22
<212> TYPE: RNA
<213> ORGANISM: Artificial Sequence
<220> FEATURE:
<223> OTHER INFORMATION: hsa-miR-502-3p

<400> SEQUENCE: 209
aaugcaccug ggcaaggauu ca                                          22

<210> SEQ ID NO 210
<211> LENGTH: 22
<212> TYPE: RNA
<213> ORGANISM: Artificial Sequence
<220> FEATURE:
<223> OTHER INFORMATION: hsa-miR-505-3p

<400> SEQUENCE: 210
cgucaacacu ugcugguuuc cu                                          22

<210> SEQ ID NO 211
<211> LENGTH: 22
<212> TYPE: RNA
<213> ORGANISM: Artificial Sequence
<220> FEATURE:
<223> OTHER INFORMATION: hsa-miR-532-3p

<400> SEQUENCE: 211
ccucccacac ccaaggcuug ca                                          22

<210> SEQ ID NO 212
<211> LENGTH: 22
<212> TYPE: RNA
<213> ORGANISM: Artificial Sequence
<220> FEATURE:
<223> OTHER INFORMATION: hsa-miR-532-5p

<400> SEQUENCE: 212
caugccuuga guguaggacc gu                                          22

<210> SEQ ID NO 213
<211> LENGTH: 21
<212> TYPE: RNA
<213> ORGANISM: Artificial Sequence
<220> FEATURE:
<223> OTHER INFORMATION: hsa-miR-551b-3p

<400> SEQUENCE: 213
gcgacccaua cuugguuuca g                                           21

<210> SEQ ID NO 214
<211> LENGTH: 24
<212> TYPE: RNA
<213> ORGANISM: Artificial Sequence
<220> FEATURE:
<223> OTHER INFORMATION: hsa-miR-573

<400> SEQUENCE: 214
cugaagugau uguuaacuga ucag                                        24

<210> SEQ ID NO 215
<211> LENGTH: 22
<212> TYPE: RNA
<213> ORGANISM: Artificial Sequence
<220> FEATURE:
```

```
<223> OTHER INFORMATION: hsa-miR-576-5p

<400> SEQUENCE: 215
auucuaauuu cuccacgucu uu                                              22

<210> SEQ ID NO 216
<211> LENGTH: 22
<212> TYPE: RNA
<213> ORGANISM: Artificial Sequence
<220> FEATURE:
<223> OTHER INFORMATION: hsa-miR-584-5p

<400> SEQUENCE: 216
uuaugguuug ccugggacug ag                                              22

<210> SEQ ID NO 217
<211> LENGTH: 22
<212> TYPE: RNA
<213> ORGANISM: Artificial Sequence
<220> FEATURE:
<223> OTHER INFORMATION: hsa-miR-589-5p

<400> SEQUENCE: 217
ugagaaccac gucugcucug ag                                              22

<210> SEQ ID NO 218
<211> LENGTH: 21
<212> TYPE: RNA
<213> ORGANISM: Artificial Sequence
<220> FEATURE:
<223> OTHER INFORMATION: hsa-miR-596

<400> SEQUENCE: 218
aagccugccc ggcuccucgg g                                               21

<210> SEQ ID NO 219
<211> LENGTH: 22
<212> TYPE: RNA
<213> ORGANISM: Artificial Sequence
<220> FEATURE:
<223> OTHER INFORMATION: hsa-miR-616-3p

<400> SEQUENCE: 219
agucauugga ggguuugagc ag                                              22

<210> SEQ ID NO 220
<211> LENGTH: 22
<212> TYPE: RNA
<213> ORGANISM: Artificial Sequence
<220> FEATURE:
<223> OTHER INFORMATION: hsa-miR-616-5p

<400> SEQUENCE: 220
acucaaaacc cuucagugac uu                                              22

<210> SEQ ID NO 221
<211> LENGTH: 23
<212> TYPE: RNA
<213> ORGANISM: Artificial Sequence
<220> FEATURE:
<223> OTHER INFORMATION: hsa-miR-618

<400> SEQUENCE: 221
aaacucuacu uguccuucug agu                                             23
```

```
<210> SEQ ID NO 222
<211> LENGTH: 22
<212> TYPE: RNA
<213> ORGANISM: Artificial Sequence
<220> FEATURE:
<223> OTHER INFORMATION: hsa-miR-627

<400> SEQUENCE: 222
gugagucucu aagaaaagag ga                                              22

<210> SEQ ID NO 223
<211> LENGTH: 22
<212> TYPE: RNA
<213> ORGANISM: Artificial Sequence
<220> FEATURE:
<223> OTHER INFORMATION: hsa-miR-629-3p

<400> SEQUENCE: 223
guucucccaa cguaagccca gc                                              22

<210> SEQ ID NO 224
<211> LENGTH: 21
<212> TYPE: RNA
<213> ORGANISM: Artificial Sequence
<220> FEATURE:
<223> OTHER INFORMATION: hsa-miR-629-5p

<400> SEQUENCE: 224
uggguuuacg uugggagaac u                                               21

<210> SEQ ID NO 225
<211> LENGTH: 21
<212> TYPE: RNA
<213> ORGANISM: Artificial Sequence
<220> FEATURE:
<223> OTHER INFORMATION: hsa-miR-650

<400> SEQUENCE: 225
aggaggcagc gcucucagga c                                               21

<210> SEQ ID NO 226
<211> LENGTH: 22
<212> TYPE: RNA
<213> ORGANISM: Artificial Sequence
<220> FEATURE:
<223> OTHER INFORMATION: hsa-miR-651

<400> SEQUENCE: 226
uuuaggauaa gcuugacuuu ug                                              22

<210> SEQ ID NO 227
<211> LENGTH: 21
<212> TYPE: RNA
<213> ORGANISM: Artificial Sequence
<220> FEATURE:
<223> OTHER INFORMATION: hsa-miR-652-3p

<400> SEQUENCE: 227
aauggcgcca cuaggguugu g                                               21

<210> SEQ ID NO 228
<211> LENGTH: 22
<212> TYPE: RNA
<213> ORGANISM: Artificial Sequence
<220> FEATURE:
<223> OTHER INFORMATION: hsa-miR-660-5p
```

<400> SEQUENCE: 228
uacccauugc auaucggagu ug					22

<210> SEQ ID NO 229
<211> LENGTH: 23
<212> TYPE: RNA
<213> ORGANISM: Artificial Sequence
<220> FEATURE:
<223> OTHER INFORMATION: hsa-miR-668

<400> SEQUENCE: 229
ugucacucgg cucggcccac uac					23

<210> SEQ ID NO 230
<211> LENGTH: 17
<212> TYPE: RNA
<213> ORGANISM: Artificial Sequence
<220> FEATURE:
<223> OTHER INFORMATION: hsa-miR-720

<400> SEQUENCE: 230
ucucgcuggg gccucca					17

<210> SEQ ID NO 231
<211> LENGTH: 22
<212> TYPE: RNA
<213> ORGANISM: Artificial Sequence
<220> FEATURE:
<223> OTHER INFORMATION: hsa-miR-874

<400> SEQUENCE: 231
cugcccuggc ccgagggacc ga					22

<210> SEQ ID NO 232
<211> LENGTH: 22
<212> TYPE: RNA
<213> ORGANISM: Artificial Sequence
<220> FEATURE:
<223> OTHER INFORMATION: hsa-miR-885-5p

<400> SEQUENCE: 232
uccauuacac uacccugccu cu					22

<210> SEQ ID NO 233
<211> LENGTH: 22
<212> TYPE: RNA
<213> ORGANISM: Artificial Sequence
<220> FEATURE:
<223> OTHER INFORMATION: hsa-miR-92a-3p

<400> SEQUENCE: 233
uauugcacuu gucccggccu gu					22

<210> SEQ ID NO 234
<211> LENGTH: 22
<212> TYPE: RNA
<213> ORGANISM: Artificial Sequence
<220> FEATURE:
<223> OTHER INFORMATION: hsa-miR-92b-3p

<400> SEQUENCE: 234
uauugcacuc gucccggccu cc					22

<210> SEQ ID NO 235
<211> LENGTH: 22

```
<212> TYPE: RNA
<213> ORGANISM: Artificial Sequence
<220> FEATURE:
<223> OTHER INFORMATION: hsa-miR-93-3p

<400> SEQUENCE: 235
acugcugagc uagcacuucc cg                                        22

<210> SEQ ID NO 236
<211> LENGTH: 23
<212> TYPE: RNA
<213> ORGANISM: Artificial Sequence
<220> FEATURE:
<223> OTHER INFORMATION: hsa-miR-93-5p

<400> SEQUENCE: 236
caaagugcug uucgugcagg uag                                       23

<210> SEQ ID NO 237
<211> LENGTH: 23
<212> TYPE: RNA
<213> ORGANISM: Artificial Sequence
<220> FEATURE:
<223> OTHER INFORMATION: hsa-miR-96-5p

<400> SEQUENCE: 237
uuuggcacua gcacauuuuu gcu                                       23

<210> SEQ ID NO 238
<211> LENGTH: 22
<212> TYPE: RNA
<213> ORGANISM: Artificial Sequence
<220> FEATURE:
<223> OTHER INFORMATION: hsa-miR-98

<400> SEQUENCE: 238
ugagguagua aguuguauug uu                                        22

<210> SEQ ID NO 239
<211> LENGTH: 22
<212> TYPE: RNA
<213> ORGANISM: Artificial Sequence
<220> FEATURE:
<223> OTHER INFORMATION: hsa-miR-99a-5p

<400> SEQUENCE: 239
aacccguaga uccgaucuug ug                                        22

<210> SEQ ID NO 240
<211> LENGTH: 22
<212> TYPE: RNA
<213> ORGANISM: Artificial Sequence
<220> FEATURE:
<223> OTHER INFORMATION: hsa-miR-99b-3p

<400> SEQUENCE: 240
caagcucgug ucuguggguc cg                                        22

<210> SEQ ID NO 241
<211> LENGTH: 22
<212> TYPE: RNA
<213> ORGANISM: Artificial Sequence
```

```
<220> FEATURE:
<223> OTHER INFORMATION: hsa-miR-99b-5p

<400> SEQUENCE: 241
cacccguaga accgaccuug cg                                        22
```

METHOD OF DETERMINING THE RISK OF DEVELOPING BREAST CANCER BY DETECTING THE EXPRESSION LEVELS OF microRNAs (miRNAs)

CROSS-REFERENCE TO RELATED APPLICATIONS

This patent application is a U.S. National Phase Application under 35 U.S.C. § 371 of International Application No. PCT/SG2016/050113, filed on 9 Mar. 2016, entitled METHOD OF DETERMINING THE RISK OF DEVELOPING BREAST CANCER BY DETECTING THE EXPRESSION LEVELS OF MICRORNAS (MIRNAS), which claims the benefit of priority of Singapore provisional application No. 10201,501781W, filed 9 Mar. 2015, the contents of which were incorporated by reference in its entirety for all purposes.

INCORPORATION BY REFERENCE

This patent application incorporates by reference the material (i.e., Sequence Listing) in the ASCII text file named Sequence Listing 9322P084 1.txt, created on March 2018, having a file size of 45,751 bytes.

FIELD OF THE INVENTION

The present invention relates generally to the field of molecular biology. In particular, the present invention relates to the use of biomarkers for the detection and diagnosis of cancer.

BACKGROUND OF THE INVENTION

Breast cancer is the most common cancer afflicting women globally, despite improvements in cancer screening. Currently, the most widely used method for breast cancer screening is mammography, with sensitivity varying from 71% to 96% and specificity in the range of 94% to 97% but with a lower sensitivity in younger women. False-positive mammograms are common occurrences in breast cancer screening programs, which result in unnecessary additional breast imaging and biopsies, and cause psychological distress to many women. The diagnosis of breast cancer relies mainly on the histological examination of tissue biopsies, or cytology of fine-needle aspirates (FNA). An attractive alternative is the use blood-based tests. To date, serum tumour markers such as CA15.3 or BR27.29 have low sensitivity and thus are not used for breast cancer detection. There is thus a need for minimally invasive methods to improve detection and early diagnosis of breast cancer.

SUMMARY OF THE INVENTION

In one aspect, the present invention refers to a method of determining the risk of developing breast cancer in a subject or determining whether a subject suffers from breast cancer, the method comprising detecting the expression level of hsa-miR-186-5p (SEQ ID NO: 77) and/or hsa-miR-409-3p (SEQ ID NO: 178) in a bodily fluid sample obtained from the subject and determining whether it is upregulated or downregulated as compared to a control, wherein upregulation of hsa-miR-186-5p (SEQ ID NO: 77) and/or downregulation of hsa-miR-409-3p (SEQ ID NO: 178) indicates that the subject has breast cancer or is at a risk of developing breast cancer.

In another aspect, the present invention refers to a method of determining the risk of developing breast cancer in a subject or determining whether a subject suffers from breast cancer, comprising the steps of detecting the presence of miRNA in a bodily fluid sample obtained from the subject; measuring the expression level of at least two miRNA listed in Table 14 in the bodily fluid sample; and using a score based on the expression level of the miRNAs measured previously to predict the likelihood of the subject to develop or to have breast cancer, wherein one of the miRNA listed in Table 14 is hsa-miR-409-3p (SEQ ID NO: 178), hsa-miR-382-5p (SEQ ID NO: 177), hsa-miR-375 (SEQ ID NO: 173), or hsa-miR-23a-3p (SEQ ID NO: 112) and wherein the hsa-miR-409-3p (SEQ ID NO: 178), hsa-miR-382-5p (SEQ ID NO: 177), hsa-miR-375 (SEQ ID NO: 173), or hsa-miR-23a-3p (SEQ ID NO: 112) is downregulated in the subject, as compared to a control.

In yet another aspect, the present invention refers to a method of determining the risk of developing breast cancer in a subject or determining whether a subject suffers from breast cancer, comprising the steps of detecting the presence of miRNA in a bodily fluid sample obtained from the subject; measuring the expression level of at least one miRNA listed in Table 13 in the bodily fluid sample; and using a score based on the expression level of the miRNAs measured previously to predict the likelihood of the subject to develop or to have breast cancer.

BRIEF DESCRIPTION OF THE DRAWINGS

The invention will be better understood with reference to the detailed description when considered in conjunction with the non-limiting examples and the accompanying drawings, in which.

DEFINITIONS

Figure 1:
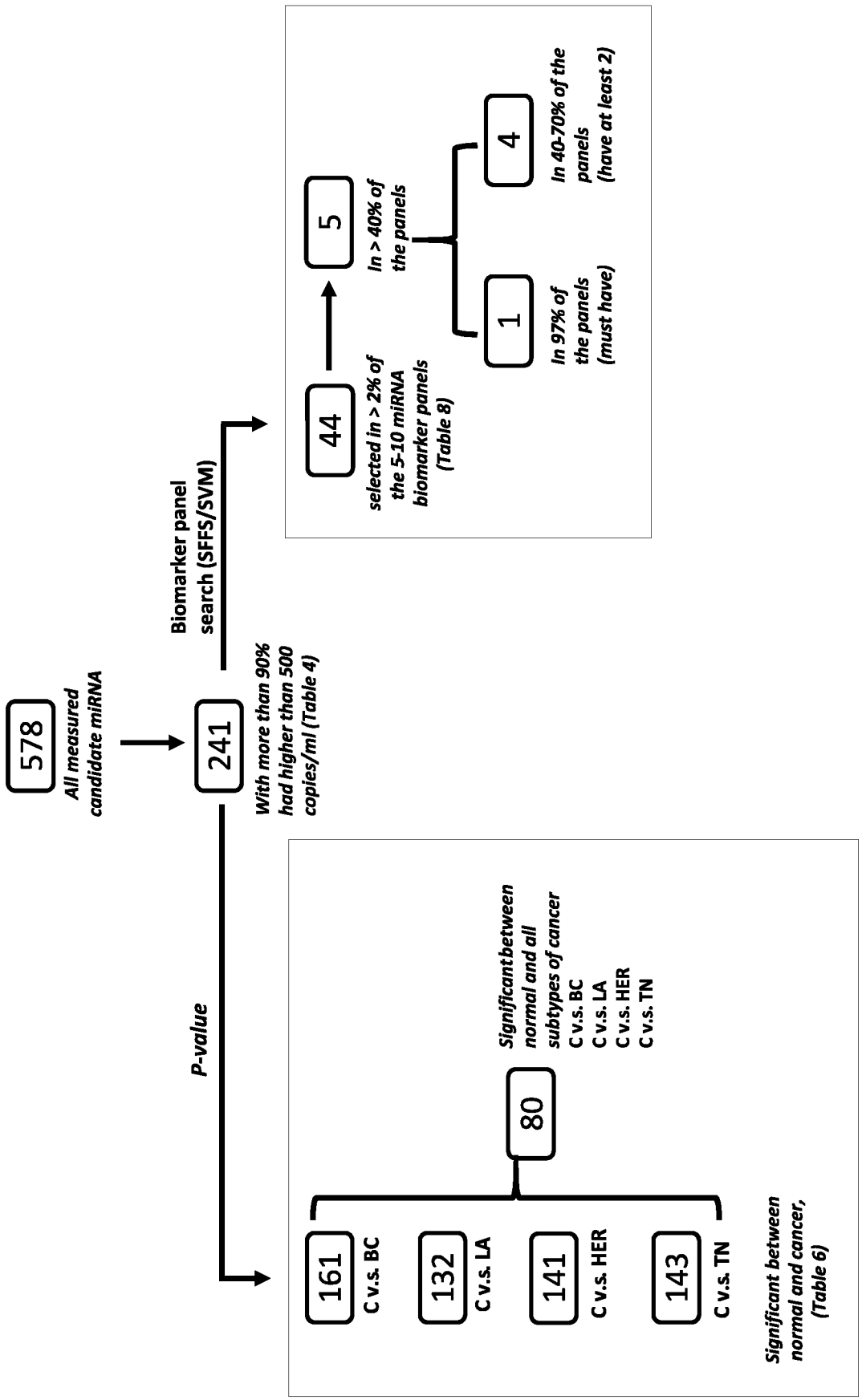
FIG. 1 shows a schematic summary of the number of miRNAs identified from studies described herein. A detailed description of how the results were established is provided in the present disclosure. C—control (cancer free (normal) subjects), BC—all breast cancer subjects, LA—luminal A subtype, HER—Her2 subtype, TN—triple negative subtype.

As used herein, the term "miRNA" refers to microRNA, small non-coding RNA molecules, which in some examples contain about 22 nucleotides, and are found in plants, animals and some viruses. miRNA are known to have functions in RNA silencing and post-transcriptional regulation of gene expression. These highly conserved RNAs regulate the expression of genes by binding to the 3'-untranslated regions (3'-UTR) of specific mRNAs. For example, each miRNA is thought to regulate multiple genes, and since hundreds of miRNA genes are predicted to be present in higher eukaryotes. miRNAs tend to be transcribed from several different loci in the genome. These genes encode for long RNAs with a hairpin structure that when processed by a series of RNaseIII enzymes (including Drosha and Dicer) form a miRNA duplex of usually ~22 nt long with 2nt overhangs on the 3'end.

As used herein, the term "regulation" refers to the process by which a cell increases or decreases the quantity of a cellular component, such as RNA or protein, in response to an external variable. An increase of a cellular component is called upregulation, while a decrease of a cellular component is called downregulation. The terms "deregulated" or "dysregulated", as used herein, mean either up or down-regulated. An example of downregulation is the cellular decrease in the number of receptors to a molecule, such as a hormone or neurotransmitter, which reduces the cell's sensitivity to the molecule. This phenomenon is an example of a locally acting negative feedback mechanism. An example of upregulation is the increased number of cytochrome P450 enzymes in liver cells when xenobiotic molecules, such as dioxin, are administered, thereby resulting in greater degradation of these molecules. Upregulation and downregulation can also happen as a response to toxins or hormones. An example of upregulation in pregnancy is hormones that cause cells in the uterus to become more sensitive to oxytocin.

As used herein, the term "differential expression" refers to the measurement of a cellular component in comparison to a control or another sample, and thereby determining the difference in, for example concentration, presence or intensity of said cellular component. The result of such a comparison can be given in the absolute, that is a component is present in the samples and not in the control, or in the relative, that is the expression or concentration of component is increased or decreased compared to the control. The terms "increased" and "decreased" in this case can be interchanged with the terms "upregulated" and "downregulated" which are also used in the present disclosure.

As used herein, the term "HER" or "Her2" refers to the human epidermal growth factor 2, a member of the human epidermal growth factor receptor (HER/EGFR/ERBB) family involved in normal cell growth. It is found on some types of cancer cells, including breast and ovarian. Cancer cells removed from the body may be tested for the presence of HER2/neu to help decide the best type of treatment. HER2/neu is a type of receptor tyrosine kinase. Also called c-erbB-2, human EGF receptor 2, and human epidermal growth factor receptor 2

As used herein, the term "Luminal A" or "LA" refers to a sub-classification of breast cancers according to a multitude of genetic markers. A breast cancer can be determined to be luminal A or luminal B, in addition to being estrogen receptor (ER) positive, progesterone receptor (PR) positive and/or hormone receptor (HR) negative, among others. Clinical definition of a luminal A cancer is a cancer that is ER positive and PR positive, but negative for HER2. Luminal A breast cancers are likely to benefit from hormone therapy and may also benefit from chemotherapy. A luminal B cancer is a cancer that is ER positive, PR negative and HER2 positive. Luminal B breast cancers are likely to benefit from chemotherapy and may benefit from hormone therapy and treatment targeted to HER2.

As used herein, the term "triple negative" or "TN" refers to a breast cancer, which had been tested and found to lack (or be negative) for hormone epidermal growth factor receptor 2 (HER-2), estrogen receptors (ER), and progesterone receptors (PR). Triple negative cancers are also known to be called "basal-like" cancers Since the tumour cells in triple negative breast cancers lack the necessary receptors, common treatments, for example hormone therapy and drugs that target estrogen, progesterone, and HER-2, are ineffective. Using chemotherapy to treat triple negative breast cancer is still an effective option. In fact, triple negative breast cancer may respond even better to chemotherapy in the earlier stages than many other forms of cancer.

As used herein, the term "(statistical) classification" refers to the problem of identifying to which of a set of categories (sub-populations) a new observation belongs, on the basis of a training set of data containing observations (or instances) whose category membership is known. An example is assigning a diagnosis to a given patient as described by observed characteristics of the patient (gender, blood pressure, presence or absence of certain symptoms, etc.). In the terminology of machine learning, classification is considered an instance of supervised learning, i.e. learning where a training set of correctly identified observations is available. The corresponding unsupervised procedure is known as clustering, and involves grouping data into categories based on some measure of inherent similarity or distance. Often, the individual observations are analysed into a set of quantifiable properties, known variously as explanatory variables or features. These properties may variously be categorical (e.g. "A", "B", "AB" or "O", for blood type), ordinal (e.g. "large", "medium" or "small"), integer-valued (e.g. the number of occurrences of a part word in an email) or real-valued (e.g. a measurement of blood pressure). Other classifiers work by comparing observations to previous observations by means of a similarity or distance function. An algorithm that implements classification, especially in a concrete implementation, is known as a classifier. The term "classifier" sometimes also refers to the mathematical function, implemented by a classification algorithm, which maps input data to a category.

As used herein, the term "pre-trained" or "supervised (machine) learning" refers to a machine learning task of inferring a function from labelled training data. The training data can consist of a set of training examples. In supervised learning, each example is a pair consisting of an input object (typically a vector) and a desired output value (also called the supervisory signal). A supervised learning algorithm, that is the algorithm to be trained, analyses the training data and produces an inferred function, which can be used for mapping new examples. An optimal scenario will allow for the algorithm to correctly determine the class labels for unseen instances. This requires the learning algorithm to generalize from the training data to unseen situations in a "reasonable" way.

As used herein, the term "score" refers to an integer or number, that can be determined mathematically, for example by using computational models a known in the art, which can include but are not limited to, SMV, as an example, and that is calculated using any one of a multitude of mathematical equations and/or algorithms known in the art for the purpose of statistical classification. Such a score is used to enumerate one outcome on a spectrum of possible outcomes. The relevance and statistical significance of such a score depends on the size and the quality of the underlying data set used to establish the results spectrum. For example, a blind sample may be input into an algorithm, which in turn calculates a score based on the information provided by the analysis of the blind sample. This results in the generation of a score for said blind sample. Based on this score, a decision can be made, for example, how likely the patient, from which the blind sample was obtained, has cancer or not. The ends of the spectrum may be defined logically based on the data provided, or arbitrarily according to the requirement of the experimenter. In both cases the spectrum needs to be defined before a blind sample is tested. As a result, the score generated by such a blind sample, for example the number "45" may indicate that the corresponding patient has cancer, based on a spectrum defined as a scale from 1 to 50, with "1" being defined as being cancer-free and "50" being defined as having cancer.

A description of breast cancer stages as described by the National Cancer Institute at the National Institutes of Health are as follows.

Stage 0 (carcinoma in situ)

There are 3 types of breast carcinoma in situ: Ductal carcinoma in situ (DCIS) is a non-invasive condition in which abnormal cells are found in the lining of a breast duct. The abnormal cells have not spread outside the duct to other tissues in the breast. In some cases, DCIS may become invasive cancer and spread to other tissues. At this time, there is no way to know which lesions could become invasive. Lobular carcinoma in situ (LCIS) is a condition in which abnormal cells are found in the lobules of the breast. This condition seldom becomes invasive cancer. Paget disease of the nipple is a condition in which abnormal cells are found in the nipple only.

Stage 1: In stage I, cancer has formed. Stage I is divided into stages IA and IB:

In stage IA, the tumour is 2 centimetres or smaller. Cancer has not spread outside the breast. In stage IB, small clusters of breast cancer cells (larger than 0.2 millimetres but not larger than 2 millimetres) are found in the lymph nodes and either: no tumour is found in the breast; or the tumour is 2 centimetres or smaller.

Stage II: Stage II is divided into stages IIA and IIB.

In stage IIA: no tumour is found in the breast or the tumour is 2 centimetres or smaller. Cancer (larger than 2 millimetres) is found in 1 to 3 axillary lymph nodes or in the lymph nodes near the breastbone (found during a sentinel lymph node biopsy); or the tumour is larger than 2 centimetres but not larger than 5 centimetres. Cancer has not spread to the lymph nodes. In stage IIB, the tumour is: larger than 2 centimetres but not larger than 5 centimetres. Small clusters of breast cancer cells (larger than 0.2 millimetres but not larger than 2 millimetres) are found in the lymph nodes; or larger than 2 centimetres but not larger than 5 centimetres. Cancer has spread to 1 to 3 axillary lymph nodes or to the lymph nodes near the breastbone (found during a sentinel lymph node biopsy); or larger than 5 centimetres. Cancer has not spread to the lymph nodes.

Stage III: Stage III is divided into stages IIIA, IIIB and IIIC.

In stage IIIA: no tumour is found in the breast or the tumour may be any size. Cancer is found in 4 to 9 axillary lymph nodes or in the lymph nodes near the breastbone (found during imaging tests or a physical exam); or the tumour is larger than 5 centimetres. Small clusters of breast cancer cells (larger than 0.2 millimetres but not larger than 2 millimetres) are found in the lymph nodes; or the tumour is larger than 5 centimetres. Cancer has spread to 1 to 3 axillary lymph nodes or to the lymph nodes near the breastbone (found during a sentinel lymph node biopsy). In stage IIIB: the tumour may be any size and cancer has spread to the chest wall and/or to the skin of the breast and caused swelling or an ulcer. Also, cancer may have spread to: up to 9 axillary lymph nodes; or the lymph nodes near the breastbone. Cancer that has spread to the skin of the breast may also be inflammatory breast cancer. In stage IIIC: no tumour is found in the breast or the tumour may be any size. Cancer may have spread to the skin of the breast and caused swelling or an ulcer and/or has spread to the chest wall. Also, cancer has spread to: 10 or more axillary lymph nodes; or lymph nodes above or below the collarbone; or axillary lymph nodes and lymph nodes near the breastbone.

Stage IV: In stage IV, cancer has spread to other organs of the body, most often the bones, lungs, liver, or brain.

DETAILED DESCRIPTION OF THE PRESENT INVENTION

The risk of false positive results is a common occurrence in mammograms, which are a regular part of breast cancer screening programs worldwide. Therefore, the diagnosis of cancer relies heavily on the histological analysis of samples obtained through, for example, fine needle aspirates (FNA). Thus, there is a need to improve detection and early diagnosis of breast cancer, thereby resulting in minimally invasive methods for the early diagnosis of breast cancer. An integrated multidimensional method for the analysis of breast cancer using miRNA in conjunction with mammography may provide a novel approach to increasing the diagnostic accuracy. To that end, the present disclosure includes lists and combinations of microRNA biomarker/biomarker panel for the diagnosis of early stage breast cancer and classification of various subtypes and stages of breast cancer subjects.

MicroRNAs (miRNAs) are small noncoding RNAs that play a central role in gene-expression regulation and aberrant expression is implicated in the pathogenesis of a variety of cancers. Since their discovery in 1993, microRNAs have been estimated to regulate more than 60% of all human genes, with many microRNAs identified as being key players in critical cellular functions such as proliferation and apoptosis. The discovery of circulating miRNAs in serum and plasma of cancer patients has raised the possibility of using circulating miRNA as biomarkers for diagnosis, prognosis, and treatment decisions for a variety of cancers.

Recently, various attempts had been made to identify circulating cell-free miRNA biomarkers in serum or plasma for the classification of breast cancer and normal, cancer-free subjects (Table 1).

TABLE 1

Summary of serum/plasma microRNA biomarker studies for breast cancer.

| Publication | Upregulated | Downregulated | Sample | Remarks |
|---|---|---|---|---|
| Kodahl et al | miR-423-5p, miR-425, miR-15a, miR-142-3p, miR-107, miR-18a | miR-365, miR-133a, miR-143, miR-145, miR-378, miR-139-5p, let-7b | Serum, 108 BC/75C | Start with 174 miRNA (qPCR), ER-positive Breast Cancer |
| Waters et al | miR-138 | — | Serum, 83 BC/83 C | Start with 3 miRNAs based on murine model |
| Si et al | miR-21 | miR-92a | Serum, 100 BC/20 C | Start with 11 miRNA, |
| Mar-Aguilar et al | miR-10b, miR-21, miR-125b, miR-145, miR-155, miR-191, miR-382 | — | Serum, 61 BC/10 C | Start with 7 miRNA, |
| Wang et al | miR-182 | — | Serum, 46 BC/58 C | Start with only one miRNA, |
| Kumar et al | miR-21, miR-146a | — | Plasma, 14 BC/8 C | Start with the two miRNAs |
| Chan et al | miR-1, miR-92a, miR-133a, miR-133b | — | Serum, 132 BC/101 C | Validate 4 miRNA based on microarray (1300 targets) |
| Eichelser et al | miR-34a, miR-93, miR-373 | — | Serum, 120 BC/40 C | Start with the 6 miRNA |
| Liu et al | miR-155 | miR-205 | Serum, 20 BC/10 C | Start with the two miRNAs |
| Sun et al | miR-155 | — | Serum, 103 BC/55 C | Start with only one miRNA |
| Schwarzenbach et al | miR-214 | — | Serum, 102 BC/53 C | Start with 4 miRNAs |
| van Schooneveld et al | miR-452 | miR-215, miR-299-5p, miR-411 | Serum, 75 BC/20 C | Validate 4 miRNA based on low density array (TaqMan) |
| Guo et al | — | miR-181a | Serum, 152 BC/75 C | Start with only one miRNA |
| Wu et al | miR-222 | — | Serum, 50 BC/50 C | Validate only one miRNA based on sequencing data |
| Hu et al | miR-16, miR-25, miR-222, miR-324-3p | — | Serum, 124 BC/124 C | Validate 10 miRNAs based on sequencing data |
| Wu et al | miR-29a, miR-21 | | Serum, 20 BC/20 C | Validate 5 miRNAs based on the sequencing data of tissues |
| Asaga et al | miR-21 | — | Serum 102 BC/20 C | Start with only one miRNA |
| Roth et al | miR-155, miR-10b, miR34a | — | Serum 89 BC/29 C | Start with 4 miRNA |
| Wang et al | miR-21, miR-106a, miR-155 | miR-126, miR-199a, miR-335 | Serum 68 BC/44 C | Start with 6 miRNA |
| Zeng et al | — | miR-30a | Plasma, 100 BC/64 C | Start with only one miRNA |
| Cuk et al | miR-148b, miR-376c, miR-409-3p, miR-801 | — | Plasma, 127 BC/80 C | Validate 7 miRNA based on low density array (TaqMan) |
| Ng et al | miR-16, miR-21, miR-451 | miR-145 | Plasma 240 BC/150 C | Validate 4 miRNA based on array (TaqMan) |
| Cuk et al | miR-127-3p, miR-148b, miR-376a, miR-376c, miR-409-3p, miR-652, miR-801 | — | Plasma, 277 BC/140 C | Validate 7 miRNA based on array (TaqMan) |
| Zhao et al | miR-589 | let-7c | Plasma 25 BC/25 C | Validate 2 miRNAs based on Microarray |
| Zhao et al | miR-425* | let-7c* | Plasma 10 BC/10 C | Validate 2 miRNAs based on Microarray |
| Heneghan et al | miR-195, let-7a | — | Whole blood 82 BC/44 C | Start with 6 miRNA |
| Heneghan et al | miR-195 | — | Whole blood 83 BC/60 C | Start with 7 miRNA |
| Khan et al | — | miR-379 | Whole blood, 40 BC/34 C | Start with only one miRNA |

TABLE 1-continued

Summary of serum/plasma microRNA biomarker studies for breast cancer.

| Publication | Upregulated | Downregulated | Sample | Remarks |
|---|---|---|---|---|
| Alshatwi et a | miR-196a2, miR-499, miR-146a | — | Whole blood, 92 BC/89 C | Start with 3 miRNA |
| Schrauder et al | miR-202 | — | Whole blood, 24 BC/24 C | Validate 2 miRNA based on microarray (1100 targets) |

The studies that measured the cell-free serum/plasma miRNAs or the whole blood were included in Table 1. Only the results validated with real-time quantitative polymerase chain reaction (RT-qPCR or qPCR) were shown. BC: breast cancer subjects. C: control subjects A number of studies have shown that the expressions of some miRNAs were differentially regulated in cancer subjects and the consistencies between these studies were disappointingly poor (Table 1). The lack of agreements in these studies can be due to a number of reasons including the use of small sample sizes or the variability in the sample sources examined. These pre-analytical issues including experimental design and workflow are predictably critical to the discovery of biomarkers. With respect to experimental design, most studies to date often begin with a high-throughput array to screen a limited set of samples (n=10–40). Due to the limitation in the sensitivity as well as the reproducibility of the technology used in these screening exercises, usually only a small set of targets (lesser than 10 miRNAs) were identified for further validation. Alternatively, attempts were made to validate candidate miRNAs (previously selected from literature) by quantitative polymerase chain reaction (qPCR) on a larger set of samples. It was shown that substantial differences exist in the performance of various measurement platforms for miRNAs and hence, significantly contribute to the inconsistency of the results from various reports. Thus, as yet, there is no consensus on the types of circulating serum/plasma miRNA that can be used as biomarkers to detect breast cancers. It is likely that the use of multivariate biomarkers for breast cancer will be highly technology dependent and may not be readily replicable across all platfoims. Hence, from discovery to eventual validated panels of biomarkers, there is also a need to build the whole workflow on pre-designated technology platform.

In the present disclosure, about 600 miRNAs were quantified by real-time quantitative polymerase chain reaction (qPCR) in the sera of 160 early stage (stage 1-2, Luminal A (LA), Her2 (HER) and triple negative (TN) subtypes) breast cancer subjects and 88 breast cancer-free healthy subjects (control group). A summary of the number of miRNAs identified for various proposed approaches used in this study is described in FIG. 1.

The result of the differential comparison for any one of the miRNAs as described in the present disclosure can result in the expression status of the miRNA being termed to be upregulated, or downregulated, or unchanged or unchanged. The combined results of the expression status of at least one or more miRNAs thus results in a diagnosis being made of a subject to have breast cancer, to not have breast cancer or to be cancer-free. Such a diagnosis can be made on the basis that a particular miRNA expression is considered to be upregulated or downregulated compared to a control or a second comparison sample. Thus, in one example, the method further comprises measuring the expression level of at least one miRNAs, which when compared to a control, the expression level is not altered in the subject. In another example, the method as described herein further comprises measuring the expression level of at least one miRNA, wherein the upregulation of miRNAs as listed as "upregulated" in, for example, Table 12, as compared to the control, diagnoses the subject to have breast cancer. In another example, the downregulation of miRNAs as listed as "downregulated" in, for example, Table 12 as compared to the control, diagnoses the subject to have breast cancer. In yet another example, the present disclosure describes a method of deteiiriining the risk of developing breast cancer in a subject or determining whether a subject suffers from breast cancer, the method comprising detecting the expression level of, for example, hsa-miR-186-5p and/or hsa-miR-409-3p in a bodily fluid (or extracellular fluid) sample obtained from the subject and determining whether it is upregulated or downregulated as compared to a control, wherein upregulation of, for example, hsa-miR-186-5p and/or downregulation of hsa-miR-409-3p indicates that the subject has breast cancer or is at a risk of developing breast cancer. In one example, the miRNA comprises hsa-miR-186-5p (SEQ ID NO: 77). In another example, the miRNA comprises hsa-miR-409-3p (SEQ ID NO: 178). In another example, the miRNA comprise hsa-miR-409-3p (SEQ ID NO: 178) and hsa-miR-186-5p (SEQ ID NO: 77). In yet another example, the miRNA comprises hsa-miR-382-5p (SEQ ID NO: 177). In yet another example, the miRNA hsa-miR-375 (SEQ ID NO: 173).

In yet another example, the miRNA comprises hsa-miR-23a-3p (SEQ ID NO: 112).

In yet another example, the miRNA comprises hsa-miR-409-3p (SEQ ID NO: 178), hsa-miR-382-5p (SEQ ID NO: 177), hsa-miR-375 (SEQ ID NO: 173), and hsa-miR-23a-3p (SEQ ID NO: 112).

In another example, the present invention refers to a method of determining the risk of developing breast cancer in a subject or determining whether a subject suffers from breast cancer, comprising the steps of detecting the presence of miRNA in a bodily fluid sample obtained from the subject; measuring the expression level of at least one, at least two, at least three, at least four, at least five or more miRNAs listed in, for example, Table 13 in the bodily fluid sample; and using a score based on the expression level of the miRNAs measured previously to predict the likelihood of the subject to develop or to have breast cancer. It is possible, for example to choose one miRNA from table 12, and then choose 3 miRNAs from table 11 and another miRNA from table 9. Thus, it is possible to choose varying numbers of miRNAs from the various tables as provided herein. A person skilled in the art, being in possession of the present disclosure, would be able to ascertain which combination would be effective for determining the presence of cancer in a subject and would also be aware that some of the miRNAs are interchangeable. As an illustrative example, the person skilled in the art having obtained a sample from a subject, would proceed to measure, for example, 6 miRNAs selected according to the methods disclosed herein from the tables disclosed herein. Having performed the measurements, in the event that, for example, the signal of one particular miRNA of the 6 selected is not in a concentration that would result in a reliable results, the person skilled in the art would be able to select a substitute miRNA based on the tables as provided herein and therefore exchange the unreadable miRNA with another. Thus, there are a multitude of combinations disclosed herein, wherein different panels of miRNAs can be used to determine the same result, that is whether the subject has cancer and, if required, what subtype the cancer is.

In the event that for example, 5 miRNAs are selected, of which only 4 have resulted in viable readings, a person skilled in the art would still be able to determine whether or not a subject has cancer, based on the significance given to each miRNA. For example, Table 14 lists both (statistically) significant and (statistically) insignificant miRNA, the latter being the last 7 rows of the table. This division of the miRNAs into significant and insignificant miRNA is based on the statistical significance and probability (in the form of, for example, p-values) that are awarded to each miRNA based on statistical validation processes, as disclosed herein. Thus, if one were to measure 3 significant and 2 insignificant miRNAs according to Table 14, and the results for the insignificant miRNAs are inconclusive, it would still be possible to obtain statistically sound determination based on the remaining 3 significant miRNAs.

Statistically speaking however, it is in the interest of statistical robustness that as many miRNAs as practical be measured in order for the result to achieve the required or expected reliability.

In another example, the method is as disclosed herein, wherein the miRNAs, which when compared to a control, the expression level is not altered in the subject is any one of the miRNAs as listed as "insignificant" in Table 14. In yet another example, the present invention refers to a method of determining the risk of developing breast cancer in a subject or determining whether a subject suffers from breast cancer, comprising the steps of detecting the presence of miRNA in a bodily fluid sample obtained from the subject; measuring the expression level of at least two miRNA listed in, for example, Table 14 in the bodily fluid sample; and using a score based on the expression level of the miRNAs measured previously to predict the likelihood of the subject to develop or to have breast cancer, wherein one of the miRNA listed in, for example, Table 14 is hsa-miR-409-3p, hsa-miR-382-5p, hsa-miR-375, or hsa-miR-23a-3p and wherein the hsa-miR-409-3p, hsa-miR-382-5p, hsa-miR-375, or hsa-miR-23a-3p is downregulated in the subject, as compared to a control. In yet another example, the miRNA is hsa-miR-122-5p.

The comparison of miRNA expression levels, as described in the methods disclosed in the present disclosure, include comparison of miRNA expression levels between miRNA from samples obtained from subject with cancer and a control group. The control group is defined as a group of subjects, wherein the subjects do not have cancer. In another example, the control group is a cancer-free group. In one example, the control group is a group of subjects, wherein the subject do not have breast cancer. In another example, the control group is a group of normal, cancer-free subjects. In another example, the control is at least one selected from the group consisting of a breast cancer free control (normal) and a breast cancer patient.

The present disclosure thus includes methods for diagnosis of breast cancer patients by measuring the level of circulating microRNAs in blood (serum), for example, a list of circulating microRNAs that can be used to classify subjects with and without early stage breast cancer; and/or a list of circulating microRNAs that can be used to classify subjects with various subtypes of breast cancer; and/or serum microRNA biomarker panels for the diagnosis of breast cancer.

It is well known that cancer is a heterogeneous disease with aberrations in the expressions of multiple genes/ pathways. Thus, combining multiple genetic targets can provide better predictions for the diagnosis, prognosis, and treatment decisions of cancers. This is especially true when analysing circulating cell-free targets like miRNAs in serum/plasma where these miRNAs are known to be contributed by a variety of tissue sources and not all of these are tumour related. Hence, the correlation of the expressions of multiple miRNAs to a disease is expected be more informative than merely using a single miRNA as biomarker.

In the present disclosure, miRNAs are identified as biomarkers for the development of multivariate index assays, which are used in the multidimensional identification of biomarkers for breast cancer. These multivariate index assays are defined by the Federal Drug Authority (FDA) as assays that, "combines the values of multiple variables using an interpretation function to yield a single, patient-specific result (e.g., a "classification," "score," "index," etc.), that is intended for use in the diagnosis of disease or other conditions, or in the cure, mitigation, treatment or prevention of disease, and provides a result whose derivation is non-transparent and cannot be independently derived or verified by the end user." Thus, highly reliable quantitative data is a pre-requisite and the use of the state-of-the art mathematical tools is essential to determine the interrelationship of these multiple variables simultaneously.

The term "score", as previously defined herein, refers to a mathematical score, which can be calculated using any one of a multitude of mathematical equations and/or algorithms known in the art for the purpose of statistical classification. Examples of such mathematical equations and/or algorithms can be, but are not limited to, a (statistical) classification algorithm selected from the group consisting of support vector machine algorithm, logistic regression algorithm, multinomial logistic regression algorithm, Fisher's linear discriminant algorithm, quadratic classifier algorithm, perceptron algorithm, k-nearest neighbours algorithm, artificial neural network algorithm, random forests algorithm, decision tree algorithm, naive Bayes algorithm, adaptive Bayes network algorithm, and ensemble learning method combining multiple learning algorithms. In another example, the classification algorithm is pre-trained using the expression level of the control. In another example, the classification algorithm compares the expression level of the subject with that of the control and returns a mathematical score that identifies the likelihood of the subject to belong to either one of the control groups.

There are a variety of methods for the measurement of miRNAs and miRNA expression including, but not limited to, hybridization-based methods, for example, microarray, northern blotting, bioluminescent, sequencing methods and real-time quantitative polymerase chain reaction (qPCR or RT-qPCR). Due to the small size of miRNA (-22 nucleotides), the most robust technology that provides precise, reproducible and accurate quantitative result and highest dynamic range is qPCR, which is currently considered the standard commonly used to validate the results of other technologies. A variation of such method is, for example, digital polymerase chain reaction (digital PCR), may also be used. Thus, in one example, the method as disclosed herein further comprises measuring the expression level of at least one microRNA (miRNA) as listed in any one of Table 9, Table 10, Table 11, Table 12, or Table 13. In another example, the method measures the differential expression level of at least one miRNA as listed in Table 12 or 13.

The present disclosure discusses the differential comparison of expression levels of miRNA in the establishment of a panel of miRNAs, based on which a deteimination of whether a subject is at risk of developing breast cancer, or a determination whether a subject suffers from breast cancer can be made. As disclosed therein, the methods as disclosed herein require the differential comparison of miRNA expression levels, usually from different groups. In one example, the comparison is made between two groups. These comparison groups can be defined as being, but are not limited to, breast-cancer, cancer-free (normal). Within the breast-cancer groups, further subgroups, for example but not limited to, HER, luminal A and triple negative, can be found. Differential comparisons can also be made between these at least two of any of the groups described herein. In one example, the expression level of the miRNAs can be expressed as, but not limited to, concentration, log(concentration), threshold cycle/quantification cycle (Ct/Cq) number, two to the power of threshold cycle/quantification cycle (Ct/Cq) number and the like.

Any sample obtained from a subject can be used according to the method of the present disclosure, so long as the sample in question contains nucleic acid sequences. More specifically, the sample is to contain RNA. In one example, the sample is obtained from a subject that may or may not have cancer. In another example, the sample is obtained from a subject who has cancer. In another example, the sample is obtained from a subject who is cancer-free. In yet another example, the sample is obtained from a subject who is breast cancer-free. In a further example, the sample is obtained from a subject who is normal and breast cancer-free.

In the case where the subject has breast cancer, the breast cancer of the subject can be attributed to a specific cancer subset, that is the breast cancer subtype can be, but not limited to, the luminal A subtype, the HER subtype, the triple negative (TN) subtype, the basal-like/basal subtype or combinations thereof. Therefore, in one example, the method is as described herein, wherein differential expression of miRNA expression in the sample obtained from the subject, as compared to a control, is indicative of the subject having any one of the breast cancer subtypes selected from the group consisting of luminal A breast cancer subtype, Her2 overexpression (HER) breast cancer subtype and triple negative (TN or basal) breast cancer subtype. In another example, the method is as described herein, wherein upregulation of miRNAs as listed as "upregulated" in, for example, Table 9, as compared to the control, diagnoses the subject to have luminal A breast cancer subtype. In another example, the downregulation of miRNAs as listed as "downregulated" in, for example, Table 9 as compared to the control, diagnoses the subject to have luminal A breast cancer subtype. In yet another example, the upregulation of miRNAs as listed as "upregulated" in, for example, Table 10, as compared to the control, diagnoses the subject to have HER breast cancer subtype. In a further example, the downregulation of miRNAs as listed as "downregulated" in, for example, Table 10 as compared to the control, diagnoses the subject to have HER breast cancer subtype. In another example, the upregulation of miRNAs as listed as "upregulated" in, for example, Table 11, as compared to the control, diagnoses the subject to have triple negative (TN) breast cancer subtype. In yet another example, the downregulation of miRNAs as listed as "downregulated" in, for example, Table 11 as compared to the control, diagnoses the subject to have triple negative (TN) breast cancer subtype.

More specifically, the sample used according to the method of the present disclosure is expected to contain ribonucleic acid sequences. Biopsy samples, for example fine needle aspirates (FNA) and the like can contain ribonucleic acid sequences required for working the methods as described herein. However, such samples would require further manipulation in order to be workable according to the methods described herein. Also, based on the disclosure herein, it is preferred to use samples that are not solid in nature, as the identification methods described herein may not be applicable. Also, in comparison, analyses performed using methods known in the art, for example histological analysis of biopsy samples are prone to produce false positives, as these histological analyses are performed by a, for example, a histopathologist, thus resulting in possible handler-based bias when analysing samples. This means that it is possible that two different people using the same method of analysis could come to different conclusion when histologically analysing tumour biopsy samples. Thus, the methods described herein disclose the use of bodily or extracellular fluids. Having said that, the sample, as described herein, can be, but is not limited to, a sample of bodily fluid or a sample of extracellular fluid. Examples of bodily or extracellular fluids are, but are not limited to, cellular and non-cellular components of amniotic fluid, breast milk, bronchial lavage, cerebrospinal fluid, colostrum, interstitial fluid, peritoneal fluids, pleural fluid, saliva, seminal fluid, urine, tears, whole blood, blood plasma, serum plasma, red blood cells, white blood cells and serum. In one example, the bodily fluid is blood serum.

A well-designed workflow with multi-layered technical controls enabled the reliable and quantitative measurement of all miRNAs simultaneously with minimized cross-over and technical noise. From such measurements, 241 miRNAs were reliably detected in all the serum samples, where 161 informative miRNAs were identified to be significantly altered between breast cancer (regardless of stages and subtypes) and normal, cancer-free subjects, with the false discovered corrected P value being lower than 0.01. Thus, in one example, the method is as disclosed herein, wherein the method measures the differential expression of at least two, at least three, at least four, at least five, at least six, at least seven, at least eight, at least nine, at least 10, at least 11, at least two to at least 20, at least 10 to at least 50, at least 40 to at least 100, at least 50 to at least 150, at least 60 to at least 163, or all miRNA as listed in, for example, Table 12. In another example, the method measures the differential expression of at least two, at least three, at least four, at least five, at least six, at least seven, at least eight, at least nine, at least 10, at least 11, at least 12, at least 13, at least 14, at least 15, at least two to at least 20, at least 10 to at least 50, at least 40 to at least 100, at least 50 to at least 134, or all of the miRNA as listed in, for example, Table 9. In yet another example, the method measures the differential expression of at least two, at least three, at least four, at least five, at least six, at least seven, at least eight, at least nine, at least 10, at least 11, at least 12, at least 13, at least 14, at least 15, at least two to at least 20, at least 10 to at least 50, at least 40 to at least 100, at least 50 to at least 143, or all of the miRNA as listed in, for example, Table 10. In a further example, the method measures the differential expression of at least two, at least three, at least four, at least five, at least six, at least seven, at least eight, at least nine, at least 10, at least 11, at least 12, at least 13, at least 14, at least 15, at least two to at least 20, at least 10 to at least 50, at least 40 to at least 100, at least 50 to at least 145, or all of the miRNA as listed in, for example, Table 11.

The present disclosure also considers the scenario in which the identified and/or measured miRNA is not 100% identical to the miRNAs as claimed in the present disclosure. Therefore, in one example, the measured miRNA has at least 90%, 95%, 97.5%, 98%, or 99% sequence identity to the miRNAs as listed in any one of Table 8, Table 9, Table 10, Table 11, Table 12, Table 13, or Table 14.

A larger number of miRNAs (total of 161) was found to be informative in stratifying breast cancer of all subtypes from normal, cancer-free subjects. In focusing on stratifying the various subtypes of breast cancer, which are luminal A (LA), HER, triple negative (TN), from noi !nal breast tissue, 131 miRNAs (LA), 141 miRNAs (HER) and 143 miRNAs (TN), respectively, were found to be informative. Of these identified miRNAs, where 80 miRNAs were found to be deregulated in the sera of all three subtypes of breast cancer. Multivariate miRNA biomarker panels were then formulated by sequence forward floating search and support vector machine using all the quantitative data obtained for the expression of 241 miRNAs with multiple times of cross-validation in silico. Using at least 5 miRNAs, the biomarker panels consistently produced values of≥0.93 when represented as areas under the curve (AUC) in the receiver operating characteristic (ROC) plot. This disclosure thus describes both novel methods and compositions of serum-based miRNAs/ miRNA panels for the detection of breast cancer on a designated technology platform. Therefore, in one example, the methods, as disclosed herein, wherein the breast cancer. In another example, the breast cancer at any stage as described by the National Cancer Institute at the National Institutes of Health. In yet another example, the breast cancer is an early stage breast cancer (stage 1 or stage 2 breast cancer).

The methods as disclosed herein can be used to determine the presence of cancer regardless of the stage of the cancer. The definition of cancer stages, as provided in the definitions section above, not only describes the phenotypical appearance of cancer cells and other hallmarks of breast cancer, but also implies a timeline in which the cancer develops. Thus, as an example, a stage 1 cancer would not have been present in the subject as long as a stage III cancer. This has implications on the methods with which the determination of the presence of cancer in a subject is made, as some methods, for example biopsies, require the positive, histological identification of tumour tissue in order to make a reliable determination. Otherwise, such diagnostic methods are hampered by the sample size or by having to wait for certain physiological changes to take place, which require time and which in term result in some breast cancers only being able to be identified at later stages, thus possibly adversely effecting prognosis of the subject. Thus, the present disclosure describes the early detection of cancer, and also the detection of the early stages of breast cancer. This is because the methods known in the art and presently used for the diagnosis of cancer are based on possibly aged technology. Thus, these, as with all technologies available to a person skilled in the art, are limited by the detection levels afforded by the physical limitations of the technology on which the methods are based. For example, may concentration related methods, for example enzyme-linked immunosorbent assays (ELISAs), are dependent on the sensitivity of the antibodies used as well as the concentration of the analyte in the sample, thereby resulting in false positive results being concluded. In terms of the methods as disclosed herein, the miRNA are secreted into the blood or other bodily fluids through various methods and are understood to be present in those fluids as soon as cancerous cells are present, thereby enabling the detection of these miRNAs using methods such as, but not limited to polymerase chain reactions (PCRs) and northern blots.

The miRNAs and the methods disclosed herein are utilised in making an early diagnosis of breast cancer. Therefore, as a result of the determination based on the methods provided herein, a subject, having been diagnosed with breast cancer using the methods described herein, can as a result of the diagnosis be treated with the necessary and relevant medication, for example chemotherapeutics, or be put on the requisite treatment regime, for example radiation treatment. Thus, the presently disclosed methods result in the treatment of a subject who is diagnosed with having breast cancer with compounds and compositions known in the art to be effective in the treatment of breast cancer. Therefore, in one example, the methods as disclosed herein result in a subject being diagnosed as having breast cancer, wherein the subject is then administered a treatment for breast cancer as known in the art. The methods as disclosed herein, can thus result in the treatment of breast cancer.

The subject, as described herein can be a mammal, whereby the mammal can be, but is not limited to humans, canines, felines and the like. In cases where the subject is a human, the ethnicity of the human can be, but is not limited to African-American, Asian, Caucasian, European, Hispanic and Pacific Islander. In one example, the human is Caucasian.

As person skilled in the art, having possession of the present disclosure, would be capable of working the present invention. An illustrative example as to the use of the present invention is provided as follows: having obtained a sample from a subject, of which is not known if they suffer from breast cancer or if they are breast cancer free, is analysed and a differential expression of a set of miRNAs, according to the present disclosure and as described in any one of Tables 9 to 14, is determined. This differential expression data is then compared to the differential expression levels as provided in Tables 9 to 12, as provided herein, and which a person skilled in the art would understand the data. Optionally, a further mathematical score may be determined, which would also take into consideration further statistical parameters relevant to increasing the significance and the accuracy of the provided data set. Based on this information, the person skilled in the art would then be able to determine if the subject in question is cancer-free or has cancer. Furthermore, based on this information, a person skilled in the art would also be able to determine if the subject, if found to have cancer, has cancer which falls into any of the three cancer subtypes as disclosed herein. These are luminal A (LA), HER2 and triple negative (TN, also known as basal-like). It would, for example, be possible to confirm whether a subject has a certain type of cancer subtype, by choosing miRNA which predominantly occur in a Table defining the miRNAs for a specific cancer subtype. For example, Table 9, as shown herein, provides data on the regulated miRNA for the cancer subtype luminal A. Thus, if a person skilled in the art chose miRNAs predominantly from this table, and the regulation indicates that the subject has cancer, then it is possible to say that the patient not only suffers from cancer, but that the cancer subtype in question is luminal A. The same conclusion may be drawn when other tables are consulted, for example, Table 10 for HER cancer subtype and Table 11 to triple negative (TN) cancer subtype. While it may not be possible to determine at what stage the cancer is at, as this would require histological analysis of a biopsy sample, it would be possible to also make a prognosis on the subject determined to have breast cancer based on the clinical severity of the subtypes as known to a person skilled in the art.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

I—Study Design

A well-designed clinical study (case-control study) was carried out to ensure the accurate identification of biomarkers for the diagnosis of breast cancer. A total of 160 Caucasian female patients with breast cancer of average age of 57.5 years old: stage 1 (n=79) and stage 2 (n=81); LA subtype (n=62), HER subtype (n=49) and TN subtype (n=49) were used in this study and comparisons were made with another 88 age-matched, normal cancer-free (healthy) Caucasian female subjects, serving as the control group. All samples were purchased from the College of American Pathologists (CAPs) accredited biobank, Asterand. All the cancer subjects were confirmed by biopsy and the serum samples were collected before any treatment. All control samples were confirmed not having any type of cancer with follow-up. The detailed clinical information of the subjects was listed in Table 2 (cancer) and Table 3 (control). All serum samples were stored at −80° C. prior to use.

TABLE 2

Clinical information of breast cancer subjects

| Subtype | AJCC/UICC Stage | Case ID | Country of Collection Site | ER | PR | Allred Hercep Her2 Test | Age |
|---|---|---|---|---|---|---|---|
| LA | I | 51715 | Romania | Positive | Positive | 1+ | 56 |
| LA | I | 51931 | Russian Federation | Positive | Positive | 0 | 47 |
| LA | I | 52618 | Ukraine | Positive | Positive | 1+ | 65 |
| LA | I | 52611 | Ukraine | Positive | Positive | 0 | 47 |
| LA | I | 52612 | Ukraine | Positive | Positive | 0 | 71 |
| LA | I | 53103 | Ukraine | Positive | Positive | 1+ | 49 |
| LA | I | 53090 | Ukraine | Positive | Positive | 0 | 54 |
| LA | I | 53060 | Ukraine | Positive | Positive | 0 | 71 |
| LA | I | 53948 | Ukraine | Positive | Positive | 0 | 59 |
| LA | I | 52665 | Ukraine | Positive | Positive | 0 | 71 |
| LA | I | 52699 | Ukraine | Positive | Positive | 1+ | 52 |
| LA | I | 53937 | Ukraine | Positive | Positive | 0 | 51 |
| LA | I | 54800 | Ukraine | Positive | Positive | 0 | 68 |
| LA | I | 53051 | Ukraine | Positive | Positive | 1+ | 59 |
| LA | I | 55072 | Ukraine | Positive | Positive | 1+ | 52 |
| LA | I | 55997 | Ukraine | Positive | Positive | 1+ | 49 |
| LA | IA | 56624 | Ukraine | Positive | Positive | 0 | 55 |
| LA | IA | 56610 | Ukraine | Positive | Positive | 0 | 50 |
| LA | IA | 56635 | Ukraine | Positive | Positive | 1+ | 47 |
| LA | IA | 56633 | Ukraine | Positive | Positive | 1+ | 53 |
| LA | IA | 56634 | Ukraine | Positive | Positive | 1+ | 55 |
| LA | I | 55988 | Ukraine | Positive | Positive | 0 | 65 |
| LA | I | 55976 | Ukraine | Positive | Positive | 1+ | 67 |
| LA | I | 55102 | Ukraine | Positive | Positive | 0 | 60 |
| LA | I | 55980 | Ukraine | Positive | Positive | 0 | 61 |
| LA | I | 55978 | Ukraine | Positive | Positive | 1+ | 58 |
| LA | I | 56047 | Ukraine | Positive | Positive | 0 | 72 |
| LA | IA | 56588 | Ukraine | Positive | Positive | 1+ | 54 |
| LA | IA | 56594 | Ukraine | Positive | Positive | 1+ | 62 |
| LA | I | 56062 | Ukraine | Positive | Positive | 0 | 48 |
| LA | IA | 58173 | Ukraine | Positive | Positive | 0 | 68 |
| LA | IIA | 51968 | Russian Federation | Positive | Positive | 0 | 62 |
| LA | IIA | 51964 | Russian Federation | Positive | Positive | 1+ | 71 |
| LA | IIA | 50900 | Russian Federation | Positive | Positive | 1+ | 72 |

TABLE 2-continued

Clinical information of breast cancer subjects

| Sub-type | AJCC/UICC Stage | Case ID | Country of Collection Site | ER | PR | Allred Her2 | Hercep Test | Age |
|---|---|---|---|---|---|---|---|---|
| LA | IIA | 52626 | Ukraine | Positive | Positive | | 0 | 67 |
| LA | IIA | 52620 | Ukraine | Positive | Positive | | 1+ | 70 |
| LA | IIA | 52682 | Ukraine | Positive | Positive | | 0 | 54 |
| LA | IIA | 53057 | Ukraine | Positive | Positive | | 0 | 55 |
| LA | IIA | 54788 | Ukraine | Positive | Positive | | 1+ | 60 |
| LA | II | 53940 | Ukraine | Positive | Positive | | 0 | 61 |
| LA | IIA | 55074 | Ukraine | Positive | Positive | | 0 | 67 |
| LA | IIA | 53105 | Ukraine | Positive | Positive | | 0 | 72 |
| LA | IIA | 53110 | Ukraine | Positive | Positive | | 0 | 48 |
| LA | IIA | 53054 | Ukraine | Positive | Positive | | 0 | 40 |
| LA | IIA | 53951 | Ukraine | Positive | Positive | | 0 | 72 |
| LA | IIA | 53952 | Ukraine | Positive | Positive | | 0 | 59 |
| LA | IIA | 53063 | Ukraine | Positive | Positive | | 0 | 72 |
| LA | IIA | 55003 | Ukraine | Positive | Positive | | 1+ | 68 |
| LA | IIA | 54998 | Ukraine | Positive | Positive | | 1+ | 64 |
| LA | IIA | 55108 | Ukraine | Positive | Positive | | 0 | 69 |
| LA | IIA | 55110 | Ukraine | Positive | Positive | | 0 | 59 |
| LA | IIA | 57159 | Ukraine | Positive | Positive | | 1+ | 47 |
| LA | IIA | 57150 | Ukraine | Positive | Positive | | 0 | 58 |
| LA | IIA | 57166 | Ukraine | Positive | Positive | | 1+ | 69 |
| LA | IIA | 57626 | Ukraine | Positive | Positive | | 0 | 54 |
| LA | IIA | 56596 | Ukraine | Positive | Positive | | 1+ | 55 |
| LA | IIA | 56019 | Ukraine | Positive | Positive | | 0 | 62 |
| LA | IIA | 56046 | Ukraine | Positive | Positive | | 1+ | 71 |
| LA | IIA | 56564 | Ukraine | Positive | Positive | | 1+ | 72 |
| LA | IIA | 57171 | Ukraine | Positive | Positive | | 0 | 71 |
| LA | IIA | 58210 | Ukraine | Positive | Positive | | 0 | 53 |
| LA | IIA | 58191 | Ukraine | Positive | Positive | | 1+ | 64 |
| TN | I | 17850 | Russian Federation | Negative | Negative | | 0 | 56 |
| TN | I | 22491 | Russian Federation | Negative | Negative | Negative | | 67 |
| TN | I | 26571 | Russian Federation | Negative | Negative | Negative | | 68 |
| TN | I | 31177 | Russian Federation | Negative | Negative | Negative | | 70 |
| TN | I | 32325 | Russian Federation | Negative | Negative | Negative | | 59 |
| TN | I | 34146 | Russian Federation | Negative | Negative | Negative | | 48 |
| TN | I | 34605 | Moldova, Republic of | Negative | Negative | Negative | | 55 |
| TN | I | 38718 | Russian Federation | Negative | Negative | Negative | | 51 |
| TN | I | 39749 | Russian Federation | Negative | Negative | Negative | | 57 |
| TN | I | 39756 | Russian Federation | Negative | Negative | Negative | | 59 |
| TN | I | 22557 | Russian Federation | Negative | Negative | | 0 | 44 |
| TN | I | 43555 | Russian Federation | Negative | Negative | Negative | | 44 |
| TN | I | 43556 | Russian Federation | Negative | Negative | Negative | | 51 |
| TN | I | 51928 | Russian Federation | Negative | Negative | | 0 | 51 |
| TN | I | 52610 | Ukraine | Negative | Negative | | 0 | 45 |
| TN | I | 52624 | Ukraine | Negative | Negative | | 0 | 47 |
| TN | I | 53059 | Ukraine | Negative | Negative | | 0 | 63 |
| TN | I | 53099 | Ukraine | Negative | Negative | | 0 | 59 |
| TN | I | 55011 | Ukraine | Negative | Negative | | 0 | 49 |
| TN | I | 56003 | Ukraine | Negative | Negative | | 0 | 43 |
| TN | I | 56004 | Ukraine | Negative | Negative | | 0 | 63 |
| TN | IA | 57140 | Ukraine | Negative | Negative | | 0 | 60 |
| TN | IA | 57183 | Ukraine | Negative | Negative | | 0 | 64 |
| TN | IA | 57204 | Ukraine | Negative | Negative | | 0 | 51 |
| TN | IIA | 25063 | Russian Federation | Negative | Negative | Negative | | 55 |
| TN | IIA | 26368 | Russian Federation | Negative | Negative | | 0 | 56 |
| TN | IIA | 26559 | Russian Federation | Negative | Negative | Negative | | 48 |
| TN | IIA | 29168 | Russian Federation | Negative | Negative | Negative | | 57 |
| TN | IIA | 29440 | Russian Federation | Negative | Negative | Negative | | 67 |
| TN | IIA | 29450 | Russian Federation | Negative | Negative | Negative | | 69 |
| TN | IIA | 31165 | Russian Federation | Negative | Negative | Negative | | 56 |
| TN | IIA | 32432 | Russian Federation | Negative | Negative | Negative | | 47 |
| TN | IIA | 32462 | Russian Federation | Negative | Negative | Negative | | 67 |
| TN | IIA | 32519 | Russian Federation | Negative | Negative | Negative | | 48 |
| TN | IIA | 34272 | Russian Federation | Negative | Negative | Negative | | 68 |
| TN | IIA | 34273 | Russian Federation | Negative | Negative | Negative | | 45 |
| TN | IIA | 34329 | Russian Federation | Negative | Negative | Negative | | 50 |
| TN | IIA | 36370 | Russian Federation | Negative | Negative | | 0 | 49 |
| TN | IIA | 36428 | Russian Federation | Negative | Negative | Negative | | 53 |
| TN | IIA | 39755 | Russian Federation | Negative | Negative | Negative | | 69 |
| TN | IIA | 39759 | Russian Federation | Negative | Negative | Negative | | 69 |
| TN | IIA | 39995 | Russian Federation | Negative | Negative | Negative | | 66 |
| TN | IIA | 40001 | Russian Federation | Negative | Negative | Negative | | 69 |
| TN | IIA | 45644 | Russian Federation | Negative | Negative | | 1+ | 45 |
| TN | IIA | 49974 | Russian Federation | Negative | Negative | | 0 | 53 |
| TN | IIA | 52698 | Ukraine | Negative | Negative | | 1+ | 58 |

TABLE 2-continued

Clinical information of breast cancer subjects

| Subtype | AJCC/UICC Stage | Case ID | Country of Collection Site | ER | PR | Allred Her2 | Hercep Test | Age |
|---|---|---|---|---|---|---|---|---|
| TN | IIA | 55103 | Ukraine | Negative | Negative | | 1+ | 56 |
| TN | IIA | 55990 | Ukraine | Negative | Negative | | 0 | 65 |
| TN | IIA | 57120 | Ukraine | Negative | Negative | | 0 | 59 |
| HER | I | 17797 | Russian Federation | Negative | Negative | | 3+ | 62 |
| HER | I | 17886 | Russian Federation | Negative | Negative | Positive | | 52 |
| HER | I | 23207 | Russian Federation | Negative | Negative | Positive | | 54 |
| HER | I | 25069 | Russian Federation | Negative | Negative | Positive | | 39 |
| HER | I | 26561 | Russian Federation | Negative | Negative | Positive | | 40 |
| HER | I | 26562 | Russian Federation | Negative | Negative | Positive | | 65 |
| HER | I | 31111 | Russian Federation | Negative | Negative | Positive | | 42 |
| HER | I | 31206 | Russian Federation | Negative | Negative | Positive | | 49 |
| HER | I | 31262 | Russian Federation | Negative | Negative | Positive | | 31 |
| HER | I | 32628 | Russian Federation | Negative | Negative | Positive | | 58 |
| HER | I | 33266 | Georgia | Negative | Negative | Positive | | 46 |
| HER | I | 34594 | Moldova, Republic of | Negative | Negative | Positive | | 39 |
| HER | I | 36492 | Russian Federation | Negative | Negative | Positive | | 37 |
| HER | I | 36494 | Russian Federation | Negative | Negative | Positive | | 60 |
| HER | I | 36802 | Russian Federation | Negative | Negative | Positive | | 43 |
| HER | I | 43559 | Russian Federation | Negative | Negative | Positive | | 72 |
| HER | I | 22504 | Russian Federation | Negative | Negative | | 3+ | 77 |
| HER | I | 53942 | Ukraine | Negative | Negative | | 3+ | 55 |
| HER | IA | 56593 | Ukraine | Negative | Negative | | 3+ | 57 |
| HER | IA | 57139 | Ukraine | Negative | Negative | | 3+ | 62 |
| HER | IA | 57141 | Ukraine | Negative | Negative | | 2+ | 63 |
| HER | IA | 57190 | Ukraine | Negative | Negative | | 3+ | 51 |
| HER | IA | 58198 | Ukraine | Negative | Negative | | 3+ | 45 |
| HER | IIA | 16820 | Russian Federation | Negative | Negative | Positive | | 61 |
| HER | IIA | 20085 | Russian Federation | Negative | Negative | Positive | | 47 |
| HER | IIA | 20809 | Russian Federation | Negative | Negative | Positive | | 61 |
| HER | IIA | 22615 | Russian Federation | Negative | Negative | | 3+ | 64 |
| HER | IIA | 25064 | Russian Federation | Negative | Negative | | 3+ | 52 |
| HER | IIA | 25122 | Russian Federation | Negative | Negative | Positive | | 51 |
| HER | IIA | 26701 | Russian Federation | Negative | Negative | | 3+ | 61 |
| HER | IIA | 29219 | Russian Federation | Negative | Negative | Positive | | 58 |
| HER | IIA | 31008 | Georgia | Negative | Negative | Positive | | 50 |
| HER | IIA | 31058 | Russian Federation | Negative | Negative | Positive | | 54 |
| HER | IIA | 31273 | Russian Federation | Negative | Negative | Positive | | 45 |
| HER | IIA | 32387 | Russian Federation | Negative | Negative | Positive | | 68 |
| HER | IIA | 32467 | Russian Federation | Negative | Negative | Positive | | 66 |
| HER | IIA | 32633 | Russian Federation | Negative | Negative | Positive | | 67 |
| HER | IIA | 36373 | Russian Federation | Negative | Negative | Positive | | 61 |
| HER | IIA | 36799 | Russian Federation | Negative | Negative | Positive | | 54 |
| HER | IIA | 41366 | Russian Federation | Negative | Negative | Positive | | 57 |
| HER | IIA | 42370 | Russian Federation | Negative | Negative | Positive | | 57 |
| HER | IIA | 52141 | Russian Federation | Negative | Negative | | 2+ | 70 |
| HER | IIA | 52690 | Ukraine | Negative | Negative | | 2+ | 57 |
| HER | IIA | 55096 | Ukraine | Negative | Negative | | 3+ | 69 |
| HER | IIA | 56645 | Ukraine | Negative | Negative | | 3+ | 65 |
| HER | IIA | 57156 | Ukraine | Negative | Negative | | 3+ | 56 |
| HER | IIA | 58185 | Ukraine | Negative | Negative | | 3+ | 37 |
| HER | IIA | 58197 | Ukraine | Negative | Negative | | 3+ | 54 |
| HER | IIA | 58212 | Ukraine | Negative | Negative | | 3+ | 62 |

The clinical information of 160 breast cancer subjects; all subjects were Caucasian and female. All serums were collected before any treatment and stored at −80° C. prior to use. The empty cells indicated those measurements were not carried out. ER—estrogen-receptor, PR—progesterone receptor, her2—human epidermal growth factor receptor 2, LA—luminal A subtype, HER—Her2 subtype, TN—triple negative subtype.

TABLE 3

Clinical information of normal (cancer-free) subjects

| Case ID | Country of Collection Site | Age | Case ID | Country of Collection Site | Age |
|---|---|---|---|---|---|
| 59509 | RUSSIAN FEDERATION | 57 | 59518 | RUSSIAN FEDERATION | 57 |
| 59592 | RUSSIAN FEDERATION | 57 | 61517 | RUSSIAN FEDERATION | 56 |
| 61518 | RUSSIAN FEDERATION | 58 | 61519 | RUSSIAN FEDERATION | 56 |
| 61526 | RUSSIAN FEDERATION | 56 | 63821 | RUSSIAN FEDERATION | 49 |
| 63822 | RUSSIAN FEDERATION | 52 | 63826 | RUSSIAN FEDERATION | 48 |
| 63831 | RUSSIAN FEDERATION | 54 | 63842 | RUSSIAN FEDERATION | 53 |

TABLE 3-continued

Clinical information of normal (cancer-free) subjects

| Case ID | Country of Collection Site | Age | Case ID | Country of Collection Site | Age |
|---|---|---|---|---|---|
| 63845 | RUSSIAN FEDERATION | 53 | 63847 | RUSSIAN FEDERATION | 52 |
| 63851 | RUSSIAN FEDERATION | 58 | 63853 | RUSSIAN FEDERATION | 57 |
| 63855 | RUSSIAN FEDERATION | 48 | 63858 | RUSSIAN FEDERATION | 48 |
| 63869 | RUSSIAN FEDERATION | 52 | 63870 | RUSSIAN FEDERATION | 51 |
| 63872 | RUSSIAN FEDERATION | 53 | 63883 | RUSSIAN FEDERATION | 51 |
| 63891 | RUSSIAN FEDERATION | 51 | 63908 | RUSSIAN FEDERATION | 51 |
| 63917 | RUSSIAN FEDERATION | 47 | 63918 | RUSSIAN FEDERATION | 48 |
| 63922 | RUSSIAN FEDERATION | 49 | 63923 | RUSSIAN FEDERATION | 50 |
| 63929 | RUSSIAN FEDERATION | 50 | 64550 | RUSSIAN FEDERATION | 42 |
| 64581 | RUSSIAN FEDERATION | 46 | 64582 | RUSSIAN FEDERATION | 51 |
| 65881 | RUSSIAN FEDERATION | 44 | 65901 | RUSSIAN FEDERATION | 48 |
| 65915 | RUSSIAN FEDERATION | 50 | 65917 | RUSSIAN FEDERATION | 50 |
| 65938 | RUSSIAN FEDERATION | 51 | 65944 | RUSSIAN FEDERATION | 55 |
| 65946 | RUSSIAN FEDERATION | 58 | 65962 | RUSSIAN FEDERATION | 52 |
| 65964 | RUSSIAN FEDERATION | 56 | 65965 | RUSSIAN FEDERATION | 52 |
| 65968 | RUSSIAN FEDERATION | 57 | 65969 | RUSSIAN FEDERATION | 53 |
| 65972 | RUSSIAN FEDERATION | 52 | 65975 | RUSSIAN FEDERATION | 50 |
| 65979 | RUSSIAN FEDERATION | 50 | 65983 | RUSSIAN FEDERATION | 57 |
| 65985 | RUSSIAN FEDERATION | 51 | 65990 | RUSSIAN FEDERATION | 50 |
| 65993 | RUSSIAN FEDERATION | 58 | 65994 | RUSSIAN FEDERATION | 57 |
| 65997 | RUSSIAN FEDERATION | 57 | 65999 | RUSSIAN FEDERATION | 54 |
| 66001 | RUSSIAN FEDERATION | 50 | 66002 | RUSSIAN FEDERATION | 61 |
| 66005 | RUSSIAN FEDERATION | 53 | 66011 | RUSSIAN FEDERATION | 53 |
| 66013 | RUSSIAN FEDERATION | 53 | 66015 | RUSSIAN FEDERATION | 50 |
| 66019 | RUSSIAN FEDERATION | 51 | 66022 | RUSSIAN FEDERATION | 56 |
| 66023 | RUSSIAN FEDERATION | 54 | 67463 | RUSSIAN FEDERATION | 55 |
| 67464 | RUSSIAN FEDERATION | 52 | 67472 | RUSSIAN FEDERATION | 51 |
| 67484 | RUSSIAN FEDERATION | 59 | 67500 | RUSSIAN FEDERATION | 51 |
| 67508 | RUSSIAN FEDERATION | 58 | 67512 | RUSSIAN FEDERATION | 48 |
| 67520 | RUSSIAN FEDERATION | 53 | 67524 | RUSSIAN FEDERATION | 50 |
| 67527 | RUSSIAN FEDERATION | 48 | 67528 | RUSSIAN FEDERATION | 50 |
| 67529 | RUSSIAN FEDERATION | 53 | 69860 | RUSSIAN FEDERATION | 65 |
| 69866 | RUSSIAN FEDERATION | 63 | 69872 | RUSSIAN FEDERATION | 60 |
| 69894 | RUSSIAN FEDERATION | 61 | 69900 | RUSSIAN FEDERATION | 63 |
| 69904 | RUSSIAN FEDERATION | 64 | 69905 | RUSSIAN FEDERATION | 61 |
| 69906 | RUSSIAN FEDERATION | 61 | 69907 | RUSSIAN FEDERATION | 65 |
| 69910 | RUSSIAN FEDERATION | 61 | 69911 | RUSSIAN FEDERATION | 60 |
| 69921 | RUSSIAN FEDERATION | 65 | 69925 | RUSSIAN FEDERATION | 65 |

The clinical information of 88 normal, cancer-free subjects; all subjects were Caucasian and female. All serums were stored at −80° C. prior to use.

Circulating cell-free miRNAs in the blood originate from different tissue sources. As a result, the change in the levels of a miRNA caused by the presence of solid tumour can be complicated by the presence of the same miRNA from other sources. Thus, determining the differences in the level of expressions of miRNAs found in cancers and the control group will be challenging and predictably less distinct. In addition, because of the dilution effect of the large volume of blood (5 litres in an adult human), most of the cell-free miRNAs are known to be of exceptionally low abundance in blood. Therefore, the accurate measurement of multiple miRNA targets from limited volume of serum/plasma samples is critical and presents a highly significant challenge. To best facilitate the discovery of significantly altered expressions of miRNAs and the identification of multivariate miRNA biomarker panels for the diagnosis of, for example, early stage breast cancer, instead of using low sensitivity or semi-quantitative screening methods, such as, for example, microarray or sequencing, it was chosen to perform qPCR-based assays with an well designed workflow.

All the reactions were performed at least twice in a single-plex manner for miRNA targets and at least four times for synthetic RNA 'spike-in' controls. To ensure the accuracy of the results in such high-throughput quantitative polymerase chain reaction (qPCR) studies, a robust workflow for the discovery of circulating biomarkers (FIG. 2) was designed and established. In this novel workflow, various artificially designed 'spike-in' controls were used to monitor and correct for technical variations in isolation, reverse transcription, augmentation and the quantitative polymerase chain reaction (qPCR) processes. All spike-in controls were non-natural synthetic miRNA mimics, which are small single-stranded RNA with length range from, for example, about 22 to about 24 bases, and which were designed in silico to have exceptionally low similarity in sequence to all known human miRNAs, thereby minimizing possible cross-hybridization to any of the primers used in the assays. In addition, the miRNA assays were deliberately divided into a number of multiplex groups in silico to minimize non-specific amplifications and primer-primer interactions. Synthetic miRNAs were used to construct standard curves for the interpolation of absolute copy numbers in all the measurements, thus further correcting for technical variations. With this highly robust workflow with multiple levels of controls, it was possible to identify low levels of expression of miRNAs in circulation reliably and reproducibly.

II—MiRNA Biomarkers

A step towards identifying biomarkers is to compare the expression levels of each miRNA in a diseased state to that of a normal, cancer-free state. The expression levels of 578 human miRNAs (according to miRBase) in all 248 serum samples, that is breast cancer and non-cancerous, normal samples, were quantitatively measured using the above outlined robust workflow and highly sensitive quantitative real-time polymerase chain reaction (qPCR) assays.

Figure 2:
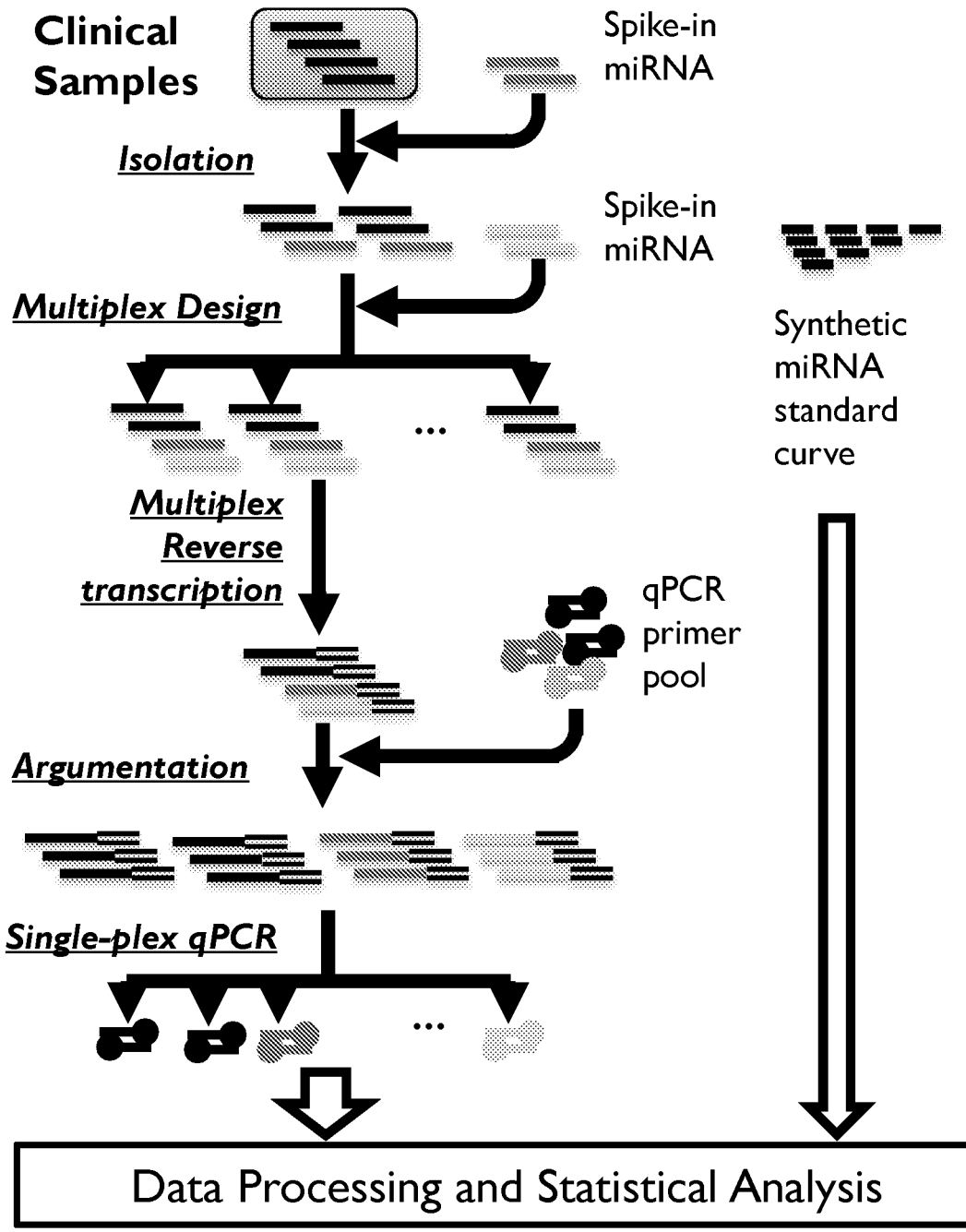
FIG. 2 shows a schematic of the process of high-throughput miRNA RT-qPCR measurement workflow. The steps shown are as follows: Isolation: isolate and purify the miRNA from serum samples; Spike-in miRNA: non-natural synthetic miRNAs mimics (small single-stranded RNA with length range from 22-24 bases) were added into the samples to monitor the efficiencies at various steps including isolation, reverse transcription, augmentation and qPCR; Multiplex Design: the miRNA assays were deliberately divided into a number of multiplex groups (45-65 miRNA per group) in silico to minimize non-specific amplifications and primer-primer interaction during the RT and augmentation processes; Multiplex reverse transcription: various pools of reverse transcription primers were combined and added to different multiplex groups to generate cDNA; Augmentation: a pool of PCR primers were combined and added to the each cDNA pool generated from a certain multiplex group and the optimized touch down PCR was carried out to enhance the amount of all cDNAs in the group simultaneously; Single-plex qPCR: the augmented cDNA pools were distributed in to various wells in the 384 well plates and single-plex qPCR reactions were then carried out; Synthetic miRNA standard curve: Synthetic miRNA stand curves were measured together with the samples for the interpolation of absolute copy numbers in all the measurements.

In the experimental design, 200 μL of serum was extracted and the total RNA was reversed transcribed and augmented by touch-down amplification to increase the amount of cDNA, but without changing the representation of the miRNA expression levels (FIG. 2). The augmented cDNA was then diluted for qPCR measurement. A simple calculation based on the effect of dilution revealed that an miRNA, which is expressed at levels≤500 copies per ml in the serum will be quantified at levels close to the detection limit of the single-plex qPCR assay (≤10 copies per well). At such concentrations, measurements pose a significant challenge due to the technical limitations, for example, errors in pipetting and sensitivity of qPCR measurements. Thus, miRNAs expressed at concentration of ≤500 copies per ml was excluded for analyses and considered undetectable in subsequent studies.

About 42% of the total 578 miRNAs assayed were found to be highly expressed in the serum. Of these, 241 miRNAs were reliably detected in more than 90% of the samples (expression levels≤500 copies per ml; Table 4). This is a higher number of miRNAs than previously reported studies using other technologies, highlighting the importance of the use of the novel experimental design and well-controlled workflow.

TABLE 4

Sequences of the 241 reliably detected mature miRNAs

| SEQ ID | miRNA | Sequence |
|---|---|---|
| SEQ ID NO: 1 | hsa-let-7a-5p | UGAGGUAGUAGGUUGUAUAGUU |
| SEQ ID NO: 2 | hsa-let-7b-3p | CUAUACAACCUACUGCCUUCCC |
| SEQ ID NO: 3 | hsa-let-7b-5p | UGAGGUAGUAGGUUGUGUGGUU |
| SEQ ID NO: 4 | hsa-let-7d-3p | CUAUACGACCUGCUGCCUUUCU |
| SEQ ID NO: 5 | hsa-let-7d-5p | AGAGGUAGUAGGUUGCAUAGUU |
| SEQ ID NO: 6 | hsa-let-7e-3p | CUAUACGGCCUCCUAGCUUUCC |
| SEQ ID NO: 7 | hsa-let-7f-1-3p | CUAUACAAUCUAUUGCCUUCCC |
| SEQ ID NO: 8 | hsa-let-7f-5p | UGAGGUAGUAGAUUGUAUAGUU |
| SEQ ID NO: 9 | hsa-let-7g-3p | CUGUACAGGCCACUGCCUUGC |
| SEQ ID NO: 10 | hsa-let-7g-5p | UGAGGUAGUAGUUUGUACAGUU |
| SEQ ID NO: 11 | hsa-let-7i-5p | UGAGGUAGUAGUUUGUGCUGUU |
| SEQ ID NO: 12 | hsa-miR-1 | UGGAAUGUAAAGAAGUAUGUAU |
| SEQ ID NO: 13 | hsa-miR-101-3p | UACAGUACUGUGAUAACUGAA |
| SEQ ID NO: 14 | hsa-miR-101-5p | CAGUUAUCACAGUGCUGAUGCU |
| SEQ ID NO: 15 | hsa-miR-103a-3p | AGCAGCAUUGUACAGGGCUAUGA |
| SEQ ID NO: 16 | hsa-miR-106b-3p | CCGCACUGUGGGUACUUGCUGC |
| SEQ ID NO: 17 | hsa-miR-106b-5p | UAAAGUGCUGACAGUGCAGAU |
| SEQ ID NO: 18 | hsa-miR-107 | AGCAGCAUUGUACAGGGCUAUCA |
| SEQ ID NO: 19 | hsa-miR-10a-3p | CAAAUUCGUAUCUAGGGGAAUA |
| SEQ ID NO: 20 | hsa-miR-10a-5p | UACCCUGUAGAUCCGAAUUUGUG |
| SEQ ID NO: 21 | hsa-miR-10b-5p | UACCCUGUAGAACCGAAUUUGUG |
| SEQ ID NO: 22 | hsa-miR-122-5p | UGGAGUGUGACAAUGGUGUUUG |
| SEQ ID NO: 23 | hsa-miR-1226-3p | UCACCAGCCCUGUGUUCCCUAG |
| SEQ ID NO: 24 | hsa-miR-124-5p | CGUGUUCACAGCGGACCUUGAU |
| SEQ ID NO: 25 | hsa-miR-125a-3p | ACAGGUGAGGUUCUUGGGAGCC |
| SEQ ID NO: 26 | hsa-miR-125b-5p | UCCCUGAGACCCUAACUUGUGA |
| SEQ ID NO: 27 | hsa-miR-126-3p | UCGUACCGUGAGUAAUAAUGCG |
| SEQ ID NO: 28 | hsa-miR-126-5p | CAUUAUUACUUUUGGUACGCG |
| SEQ ID NO: 29 | hsa-miR-127-3p | UCGGAUCCGUCUGAGCUUGGCU |

TABLE 4-continued

Sequences of the 241 reliably detected mature miRNAs

| SEQ ID | miRNA | Sequence |
|---|---|---|
| SEQ ID NO: 30 | hsa-miR-128 | UCACAGUGAACCGGUCUCUUU |
| SEQ ID NO: 31 | hsa-miR-1280 | UCCCACCGCUGCCACCC |
| SEQ ID NO: 32 | hsa-miR-1285-3p | UCUGGGCAACAAAGUGAGACCU |
| SEQ ID NO: 33 | hsa-miR-1291 | UGGCCCUGACUGAAGACCAGCAGU |
| SEQ ID NO: 34 | hsa-miR-1299 | UUCUGGAAUUCUGUGUGAGGGA |
| SEQ ID NO: 35 | hsa-miR-130a-3p | CAGUGCAAUGUUAAAGGGCAU |
| SEQ ID NO: 36 | hsa-miR-130b-3p | CAGUGCAAUGAUGAAAGGGCAU |
| SEQ ID NO: 37 | hsa-miR-130b-5p | ACUCUUUCCCUGUUGCACUAC |
| SEQ ID NO: 38 | hsa-miR-133a | UUUGGUCCCCUUCAACCAGCUG |
| SEQ ID NO: 39 | hsa-miR-135a-5p | UAUGGCUUUUUAUUCCUAUGUGA |
| SEQ ID NO: 40 | hsa-miR-136-3p | CAUCAUCGUCUCAAAUGAGUCU |
| SEQ ID NO: 41 | hsa-miR-136-5p | ACUCCAUUUGGAUGAUGGA |
| SEQ ID NO: 42 | hsa-miR-139-5p | UCUACAGUGCACGUGUCUCCAG |
| SEQ ID NO: 43 | hsa-miR-140-3p | UACCACAGGGUAGAACCACGG |
| SEQ ID NO: 44 | hsa-miR-140-5p | CAGUGGUUUUACCCUAUGGUAG |
| SEQ ID NO: 45 | hsa-miR-141-3p | UAACACUGUCUGGUAAAGAUGG |
| SEQ ID NO: 46 | hsa-miR-142-5p | CAUAAAGUAGAAAGCACUACU |
| SEQ ID NO: 47 | hsa-miR-143-3p | UGAGAUGAAGCACUGUAGCUC |
| SEQ ID NO: 48 | hsa-miR-144-3p | UACAGUAUAGAUGAUGUACU |
| SEQ ID NO: 49 | hsa-miR-144-5p | GGAUAUCAUCAUAUACUGUAAG |
| SEQ ID NO: 50 | hsa-miR-145-5p | GUCCAGUUUUCCCAGGAAUCCCU |
| SEQ ID NO: 51 | hsa-miR446a-5p | UGAGAACUGAAUUCCAUGGGUU |
| SEQ ID NO: 52 | hsa-miR-146b-5p | UGAGAACUGAAUUCCAUAGGCU |
| SEQ ID NO: 53 | hsa-miR-148a-3p | UCAGUGCACUACAGAACUUUGU |
| SEQ ID NO: 54 | hsa-miR-148a-5p | AAAGUUCUGAGACACUCCGACU |
| SEQ ID NO: 55 | hsa-miR-148b-3p | UCAGUGCAUCACAGAACUUUGU |
| SEQ ID NO: 56 | hsa-miR-148b-5p | AAGUUCUGUUAUACACUCAGGC |
| SEQ ID NO: 57 | hsa-miR-150-3p | CUGGUACAGGCCUGGGGGACAG |
| SEQ ID NO: 58 | hsa-miR-150-5p | UCUCCCAACCCUUGUACCAGUG |
| SEQ ID NO: 59 | hsa-miR-151a-3p | CUAGACUGAAGCUCCUUGAGG |
| SEQ ID NO: 60 | hsa-miR-151a-5p | UCGAGGAGCUCACAGUCUAGU |
| SEQ ID NO: 61 | hsa-miR-152 | UCAGUGCAUGACAGAACUUGG |
| SEQ ID NO: 62 | hsa-miR-154-5p | UAGGUUAUCCGUGUUGCCUUCG |
| SEQ ID NO: 63 | hsa-miR-15a-3p | CAGGCCAUAUUGUGCUGCCUCA |
| SEQ ID NO: 64 | hsa-miR-15a-5p | UAGCAGCACAUAAUGGUUUGUG |
| SEQ ID NO: 65 | hsa-miR-15b-3p | CGAAUCAUUAUUUGCUGCUCUA |
| SEQ ID NO: 66 | hsa-miR-15b-5p | UAGCAGCACAUCAUGGUUUACA |
| SEQ ID NO: 67 | hsa-miR-16-5p | UAGCAGCACGUAAAUAUUGGCG |

TABLE 4-continued

Sequences of the 241 reliably detected mature miRNAs

| SEQ ID | miRNA | Sequence |
| --- | --- | --- |
| SEQ ID NO: 68 | hsa-miR-17-3p | ACUGCAGUGAAGGCACUUGUAG |
| SEQ ID NO: 69 | hsa-miR-17-5p | CAAAGUGCUUACAGUGCAGGUAG |
| SEQ ID NO: 70 | hsa-miR-181a-2-3p | ACCACUGACCGUUGACUGUACC |
| SEQ ID NO: 71 | hsa-miR-181a-5p | AACAUUCAACGCUGUCGGUGAGU |
| SEQ ID NO: 72 | hsa-miR-181b-5p | AACAUUCAUUGCUGUCGGUGGGU |
| SEQ ID NO: 73 | hsa-miR-181d | AACAUUCAUUGUUGUCGGUGGGU |
| SEQ ID NO: 74 | hsa-miR-1825 | UCCAGUGCCCUCCUCUCC |
| SEQ ID NO: 75 | hsa-miR-183-5p | UAUGGCACUGGUAGAAUUCACU |
| SEQ ID NO: 76 | hsa-miR-185-5p | UGGAGAGAAAGGCAGUUCCUGA |
| SEQ ID NO: 77 | hsa-miR-186-5p | CAAAGAAUUCUCCUUUUGGGCU |
| SEQ ID NO: 78 | hsa-miR-18a-3p | ACUGCCCUAAGUGCUCCUUCUGG |
| SEQ ID NO: 79 | hsa-miR-18a-5p | UAAGGUGCAUCUAGUGCAGAUAG |
| SEQ ID NO: 80 | hsa-miR-18b-5p | UAAGGUGCAUCUAGUGCAGUUAG |
| SEQ ID NO: 81 | hsa-miR-191-5p | CAACGGAAUCCCAAAAGCAGCUG |
| SEQ ID NO: 82 | hsa-miR-192-5p | CUGACCUAUGAAUUGACAGCC |
| SEQ ID NO: 83 | hsa-miR-193a-5p | UGGGUCUUUGCGGGCGAGAUGA |
| SEQ ID NO: 84 | hsa-miR-193b-3p | AACUGGCCCUCAAAGUCCCGCU |
| SEQ ID NO: 85 | hsa-miR-194-5p | UGUAACAGCAACUCCAUGUGGA |
| SEQ ID NO: 86 | hsa-miR-195-5p | UAGCAGCACAGAAAUAUUGGC |
| SEQ ID NO: 87 | hsa-miR-196a-5p | UAGGUAGUUUCAUGUUGUUGGG |
| SEQ ID NO: 88 | hsa-miR-196b-5p | UAGGUAGUUUCCUGUUGUUGGG |
| SEQ ID NO: 89 | hsa-miR-197-3p | UUCACCACCUUCUCCACCCAGC |
| SEQ ID NO: 90 | hsa-miR-199a-3p | ACAGUAGUCUGCACAUUGGUUA |
| SEQ ID NO: 91 | hsa-miR-199a-5p | CCCAGUGUUCAGACUACCUGUUC |
| SEQ ID NO: 92 | hsa-miR-199b-3p | ACAGUAGUCUGCACAUUGGUUA |
| SEQ ID NO: 93 | hsa-miR-19a-3p | UGUGCAAAUCUAUGCAAAACUGA |
| SEQ ID NO: 94 | hsa-miR-19b-3p | UGUGCAAAUCCAUGCAAAACUGA |
| SEQ ID NO: 95 | hsa-miR-200b-3p | UAAUACUGCCUGGUAAUGAUGA |
| SEQ ID NO: 96 | hsa-miR-200c-3p | UAAUACUGCCGGGUAAUGAUGGA |
| SEQ ID NO: 97 | hsa-miR-205-5p | UCCUUCAUUCCACCGGAGUCUG |
| SEQ ID NO: 98 | hsa-miR-206 | UGGAAUGUAAGGAAGUGUGUGG |
| SEQ ID NO: 99 | hsa-miR-20a-5p | UAAAGUGCUUAUAGUGCAGGUAG |
| SEQ ID NO: 100 | hsa-miR-20b-5p | CAAAGUGCUCAUAGUGCAGGUAG |
| SEQ ID NO: 101 | hsa-miR-21-3p | CAACACCAGUCGAUGGGCUGU |
| SEQ ID NO: 102 | hsa-miR-214-3p | ACAGCAGGCACAGACAGGCAGU |
| SEQ ID NO: 103 | hsa-miR-21-5p | UAGCUUAUCAGACUGAUGUUGA |
| SEQ ID NO: 104 | hsa-miR-219-5p | UGAUUGUCCAAACGCAAUUCU |
| SEQ ID NO: 105 | hsa-miR-221-3p | AGCUACAUUGUCUGCUGGGUUUC |

TABLE 4-continued

Sequences of the 241 reliably detected mature miRNAs

| SEQ ID | miRNA | Sequence |
|---|---|---|
| SEQ ID NO: 106 | hsa-miR-221-5p | ACCUGGCAUACAAUGUAGAUUU |
| SEQ ID NO: 107 | hsa-miR-222-3p | AGCUACAUCUGGCUACUGGGU |
| SEQ ID NO: 108 | hsa-miR-223-3p | UGUCAGUUUGUCAAAUACCCCA |
| SEQ ID NO: 109 | hsa-miR-22-3p | AAGCUGCCAGUUGAAGAACUGU |
| SEQ ID NO: 110 | hsa-miR-224-5p | CAAGUCACUAGUGGUUCCGUU |
| SEQ ID NO: 111 | hsa-miR-2355-3p | AUUGUCCUUGCUGUUUGGAGAU |
| SEQ ID NO: 112 | hsa-miR-23a-3p | AUCACAUUGCCAGGGAUUUCC |
| SEQ ID NO: 113 | hsa-miR-23a-5p | GGGGUUCCUGGGGAUGGGAUUU |
| SEQ ID NO: 114 | hsa-miR-23b-3p | AUCACAUUGCCAGGGAUUACC |
| SEQ ID NO: 115 | hsa-miR-23c | AUCACAUUGCCAGUGAUUACCC |
| SEQ ID NO: 116 | hsa-miR-24-3p | UGGCUCAGUUCAGCAGGAACAG |
| SEQ ID NO: 117 | hsa-miR-25-3p | CAUUGCACUUGUCUCGGUCUGA |
| SEQ ID NO: 118 | hsa-miR-26a-5p | UUCAAGUAAUCCAGGAUAGGCU |
| SEQ ID NO: 119 | hsa-miR-26b-3p | CCUGUUCUCCAUUACUUGGCUC |
| SEQ ID NO: 120 | hsa-miR-26b-5p | UUCAAGUAAUUCAGGAUAGGU |
| SEQ ID NO: 121 | hsa-miR-27a-3p | UUCACAGUGGCUAAGUUCCGC |
| SEQ ID NO: 122 | hsa-miR-27a-5p | AGGGCUUAGCUGCUUGUGAGCA |
| SEQ ID NO: 123 | hsa-miR-27b-3p | UUCACAGUGGCUAAGUUCUGC |
| SEQ ID NO: 124 | hsa-miR-28-3p | CACUAGAUUGUGAGCUCCUGGA |
| SEQ ID NO: 125 | hsa-miR-28-5p | AAGGAGCUCACAGUCUAUUGAG |
| SEQ ID NO: 126 | hsa-miR-299-3p | UAUGUGGGAUGGUAAACCGCUU |
| SEQ ID NO: 127 | hsa-miR-29a-3p | UAGCACCAUCUGAAAUCGGUUA |
| SEQ ID NO: 128 | hsa-miR-29b-2-5p | CUGGUUUCACAUGGUGGCUUAG |
| SEQ ID NO: 129 | hsa-miR-29b-3p | UAGCACCAUUUGAAAUCAGUGUU |
| SEQ ID NO: 130 | hsa-miR-29c-3p | UAGCACCAUUUGAAAUCGGUUA |
| SEQ ID NO: 131 | hsa-miR-29c-5p | UGACCGAUUUCUCCUGGUGUUC |
| SEQ ID NO: 132 | hsa-miR-301a-3p | CAGUGCAAUAGUAUUGUCAAAGC |
| SEQ ID NO: 133 | hsa-miR-30a-5p | UGUAAACAUCCUCGACUGGAAG |
| SEQ ID NO: 134 | hsa-miR-30b-5p | UGUAAACAUCCUACACUCAGCU |
| SEQ ID NO: 135 | hsa-miR-30c-5p | UGUAAACAUCCUACACUCUCAGC |
| SEQ ID NO: 136 | hsa-miR-30d-3p | CUUUCAGUCAGAUGUUUGCUGC |
| SEQ ID NO: 137 | hsa-miR-30d-5p | UGUAAACAUCCCCGACUGGAAG |
| SEQ ID NO: 138 | hsa-miR-30e-3p | CUUUCAGUCGGAUGUUUACAGC |
| SEQ ID NO: 139 | hsa-miR-30e-5p | UGUAAACAUCCUUGACUGGAAG |
| SEQ ID NO: 140 | hsa-miR-320a | AAAAGCUGGGUUGAGAGGGCGA |
| SEQ ID NO: 141 | hsa-miR-320b | AAAAGCUGGGUUGAGAGGGCAA |
| SEQ ID NO: 142 | hsa-miR-320c | AAAAGCUGGGUUGAGAGGGU |
| SEQ ID NO: 143 | hsa-miR-320d | AAAAGCUGGGUUGAGAGGA |

TABLE 4-continued

Sequences of the 241 reliably detected mature miRNAs

| SEQ ID | miRNA | Sequence |
|---|---|---|
| SEQ ID NO: 144 | hsa-miR-320e | AAAGCUGGGUUGAGAAGG |
| SEQ ID NO: 145 | hsa-miR-324-3p | ACUGCCCCAGGUGCUGCUGG |
| SEQ ID NO: 146 | hsa-miR-324-5p | CGCAUCCCCUAGGGCAUUGGUGU |
| SEQ ID NO: 147 | hsa-miR-32-5p | UAUUGCACAUUACUAAGUUGCA |
| SEQ ID NO: 148 | hsa-miR-326 | CCUCUGGGCCCUUCCUCCAG |
| SEQ ID NO: 149 | hsa-miR-328 | CUGGCCCUCUCUGCCCUUCCGU |
| SEQ ID NO: 150 | hsa-miR-330-3p | GCAAAGCACACGGCCUGCAGAGA |
| SEQ ID NO: 151 | hsa-miR-331-5p | CUAGGUAUGGUCCCAGGGAUCC |
| SEQ ID NO: 152 | hsa-miR-335-3p | UUUUUCAUUAUUGCUCCUGACC |
| SEQ ID NO: 153 | hsa-miR-335-5p | UCAAGAGCAAUAACGAAAAAUGU |
| SEQ ID NO: 154 | hsa-miR-337-3p | CUCCUAUAUGAUGCCUUUCUUC |
| SEQ ID NO: 155 | hsa-miR-337-5p | GAACGGCUUCAUACAGGAGUU |
| SEQ ID NO: 156 | hsa-miR-338-5p | AACAAUAUCCUGGUGCUGAGUG |
| SEQ ID NO: 157 | hsa-miR-339-3p | UGAGCGCCUCGACGACAGAGCCG |
| SEQ ID NO: 158 | hsa-miR-339-5p | UCCCUGUCCUCCAGGAGCUCACG |
| SEQ ID NO: 159 | hsa-miR-340-5p | UUAUAAAGCAAUGAGACUGAUU |
| SEQ ID NO: 160 | hsa-miR-342-5p | AGGGGUGCUAUCUGUGAUUGA |
| SEQ ID NO: 161 | hsa-miR-34a-5p | UGGCAGUGUCUUAGCUGGUUGU |
| SEQ ID NO: 162 | hsa-miR-34b-5p | UAGGCAGUGUCAUUAGCUGAUUG |
| SEQ ID NO: 163 | hsa-miR-361-5p | UUAUCAGAAUCUCCAGGGGUAC |
| SEQ ID NO: 164 | hsa-miR-362-3p | AACACACCUAUUCAAGGAUUCA |
| SEQ ID NO: 165 | hsa-miR-362-5p | AAUCCUUGGAACCUAGGUGUGAGU |
| SEQ ID NO: 166 | hsa-miR-363-3p | AAUUGCACGGUAUCCAUCUGUA |
| SEQ ID NO: 167 | hsa-miR-365a-3p | UAAUGCCCCUAAAAAUCCUUAU |
| SEQ ID NO: 168 | hsa-miR-369-5p | AGAUCGACCGUGUUAUAUUCGC |
| SEQ ID NO: 169 | hsa-miR-370 | GCCUGCUGGGGUGGAACCUGGU |
| SEQ ID NO: 170 | hsa-miR-374a-3p | CUUAUCAGAUUGUAUUGUAAUU |
| SEQ ID NO: 171 | hsa-miR-374a-5p | UUAUAAUACAACCUGAUAAGUG |
| SEQ ID NO: 172 | hsa-miR-374b-5p | AUAUAAUACAACCUGCUAAGUG |
| SEQ ID NO: 173 | hsa-miR-375 | UUUGUUCGUUCGGCUCGCGUGA |
| SEQ ID NO: 174 | hsa-miR-376a-5p | GUAGAUUCUCCUUCUAUGAGUA |
| SEQ ID NO: 175 | hsa-miR-378a-3p | ACUGGACUUGGAGUCAGAAGG |
| SEQ ID NO: 176 | hsa-miR-378a-5p | CUCCUGACUCCAGGUCCUGUGU |
| SEQ ID NO: 177 | hsa-miR-382-5p | GAAGUUGUUCGUGGUGGAUUCG |
| SEQ ID NO: 178 | hsa-miR-409-3p | GAAUGUUGCUCGGUGAACCCCU |
| SEQ ID NO: 179 | hsa-miR-411-3p | UAUGUAACACGGUCCACUAACC |
| SEQ ID NO: 180 | hsa-miR-411-5p | UAGUAGACCGUAUAGCGUACG |
| SEQ ID NO: 181 | hsa-miR-423-5p | UGAGGGGCAGAGAGCGAGACUUU |

TABLE 4-continued

Sequences of the 241 reliably detected mature miRNAs

| SEQ ID | miRNA | Sequence |
|---|---|---|
| SEQ ID NO: 182 | hsa-miR-424-5p | CAGCAGCAAUUCAUGUUUUGAA |
| SEQ ID NO: 183 | hsa-miR-425-3p | AUCGGGAAUGUCGUGUCCGCCC |
| SEQ ID NO: 184 | hsa-miR-425-5p | AAUGACACGAUCACUCCCGUUGA |
| SEQ ID NO: 185 | hsa-miR-429 | UAAUACUGUCUGGUAAAACCGU |
| SEQ ID NO: 186 | hsa-miR-4306 | UGGAGAGAAAGGCAGUA |
| SEQ ID NO: 187 | hsa-miR-431-5p | UGUCUUGCAGGCCGUCAUGCA |
| SEQ ID NO: 188 | hsa-miR-432-5p | UCUUGGAGUAGGUCAUUGGGUGG |
| SEQ ID NO: 189 | hsa-miR-450a-5p | UUUUGCGAUGUGUUCCUAAUAU |
| SEQ ID NO: 190 | hsa-miR-451a | AAACCGUUACCAUUACUGAGUU |
| SEQ ID NO: 191 | hsa-miR-452-5p | AACUGUUUGCAGAGGAAACUGA |
| SEQ ID NO: 192 | hsa-miR-454-3p | UAGUGCAAUAUUGCUUAUAGGGU |
| SEQ ID NO: 193 | hsa-miR-454-5p | ACCCUAUCAAUAUUGUCUCUGC |
| SEQ ID NO: 194 | hsa-miR-4732-3p | GCCCUGACCUGUCCUGUUCUG |
| SEQ ID NO: 195 | hsa-miR-483-3p | UCACUCCUCUCCUCCCGUCUU |
| SEQ ID NO: 196 | hsa-miR-483-5p | AAGACGGGAGGAAAGAAGGGAG |
| SEQ ID NO: 197 | hsa-miR-484 | UCAGGCUCAGUCCCCUCCCGAU |
| SEQ ID NO: 198 | hsa-miR-485-3p | GUCAUACACGGCUCUCCUCUCU |
| SEQ ID NO: 199 | hsa-miR-485-5p | AGAGGCUGGCCGUGAUGAAUUC |
| SEQ ID NO: 200 | hsa-miR-486-5p | UCCUGUACUGAGCUGCCCCGAG |
| SEQ ID NO: 201 | hsa-miR-487b | AAUCGUACAGGGUCAUCCACUU |
| SEQ ID NO: 202 | hsa-miR-491-5p | AGUGGGGAACCCUUCCAUGAGG |
| SEQ ID NO: 203 | hsa-miR-493-5p | UUGUACAUGGUAGGCUUUCAUU |
| SEQ ID NO: 204 | hsa-miR-497-5p | CAGCAGCACACUGUGGUUUGU |
| SEQ ID NO: 205 | hsa-miR-499a-5p | UUAAGACUUGCAGUGAUGUUU |
| SEQ ID NO: 206 | hsa-miR-500a-3p | AUGCACCUGGGCAAGGAUUCUG |
| SEQ ID NO: 207 | hsa-miR-500a-5p | UAAUCCUUGCUACCUGGGUGAGA |
| SEQ ID NO: 208 | hsa-miR-501-5p | AAUCCUUUGUCCCUGGGUGAGA |
| SEQ ID NO: 209 | hsa-miR-502-3p | AAUGCACCUGGGCAAGGAUUCA |
| SEQ ID NO: 210 | hsa-miR-505-3p | CGUCAACACUUGCUGGUUUCCU |
| SEQ ID NO: 211 | hsa-miR-532-3p | CCUCCCACACCCAAGGCUUGCA |
| SEQ ID NO: 212 | hsa-miR-532-5p | CAUGCCUUGAGUGUAGGACCGU |
| SEQ ID NO: 213 | hsa-miR-551b-3p | GCGACCCAUACUUGGUUUCAG |
| SEQ ID NO: 214 | hsa-miR-573 | CUGAAGUGAUGUGUAACUGAUCAG |
| SEQ ID NO: 215 | hsa-miR-576-5p | AUUCUAAUUUCUCCACGUCUUU |
| SEQ ID NO: 216 | hsa-miR-584-5p | UUAUGGUUUGCCUGGGACUGAG |
| SEQ ID NO: 217 | hsa-miR-589-5p | UGAGAACCACGUCUGCUCUGAG |
| SEQ ID NO: 218 | hsa-miR-596 | AAGCCUGCCCGGCUCCUCGGG |
| SEQ ID NO: 219 | hsa-miR-616-3p | AGUCAUUGGAGGGUUUGAGCAG |

TABLE 4-continued

Sequences of the 241 reliably detected mature miRNAs

| SEQ ID | miRNA | Sequence |
| --- | --- | --- |
| SEQ ID NO: 220 | hsa-miR-616-5p | ACUCAAAACCCUUCAGUGACUU |
| SEQ ID NO: 221 | hsa-miR-618 | AAACUCUACUUGUCCUUCUGAGU |
| SEQ ID NO: 222 | hsa-miR-627 | GUGAGUCUCUAAGAAAAGAGGA |
| SEQ ID NO: 223 | hsa-miR-629-3p | GUUCUCCCAACGUAAGCCCAGC |
| SEQ ID NO: 224 | hsa-miR-629-5p | UGGGUUUACGUUGGGAGAACU |
| SEQ ID NO: 225 | hsa-miR-650 | AGGAGGCAGCGCUCUCAGGAC |
| SEQ ID NO: 226 | hsa-miR-651 | UUUAGGAUAAGCUUGACUUUUG |
| SEQ ID NO: 227 | hsa-miR-652-3p | AAUGGCGCCACUAGGGUUGUG |
| SEQ ID NO: 228 | hsa-miR-660-5p | UACCCAUUGCAUAUCGGAGUUG |
| SEQ ID NO: 229 | hsa-miR-668 | UGUCACUCGGCUCGGCCCACUAC |
| SEQ ID NO: 230 | hsa-miR-720 | UCUCGCUGGGGCCUCCA |
| SEQ ID NO: 231 | hsa-miR-874 | CUGCCCUGGCCCGAGGGACCGA |
| SEQ ID NO: 232 | hsa-miR-885-5p | UCCAUUACACUACCCUGCCUCU |
| SEQ ID NO: 233 | hsa-miR-92a-3p | UAUUGCACUUGUCCCGGCCUGU |
| SEQ ID NO: 234 | hsa-miR-92b-3p | UAUUGCACUCGUCCCGGCCUCC |
| SEQ ID NO: 235 | hsa-miR-93-3p | ACUGCUGAGCUAGCACUUCCCG |
| SEQ ID NO: 236 | hsa-miR-93-5p | CAAAGUGCUGUUCGUGCAGGUAG |
| SEQ ID NO: 237 | hsa-miR-96-5p | UUUGGCACUAGCACAGCU |
| SEQ ID NO: 238 | hsa-miR-98 | UGAGGUAGUAAGUUGUAUUGUU |
| SEQ ID NO: 239 | hsa-miR-99a-5p | AACCCGUAGAUCCGAUCUUGUG |
| SEQ ID NO: 240 | hsa-miR-99b-3p | CAAGCUCGUGUCUGUGGGUCCG |
| SEQ ID NO: 241 | hsa-miR-99b-5p | CACCCGUAGAACCGACCUUGCG |

Table 4 lists the 241 mature miRNAs which had been reliable detected in the serum samples. The definition of "reliably detected" is that at least 90% of the serum samples had a concentration higher than 500 copies per ml of a particular miRNA. The miRNAs were named according to the miRBase V18 release.

Figure 3:
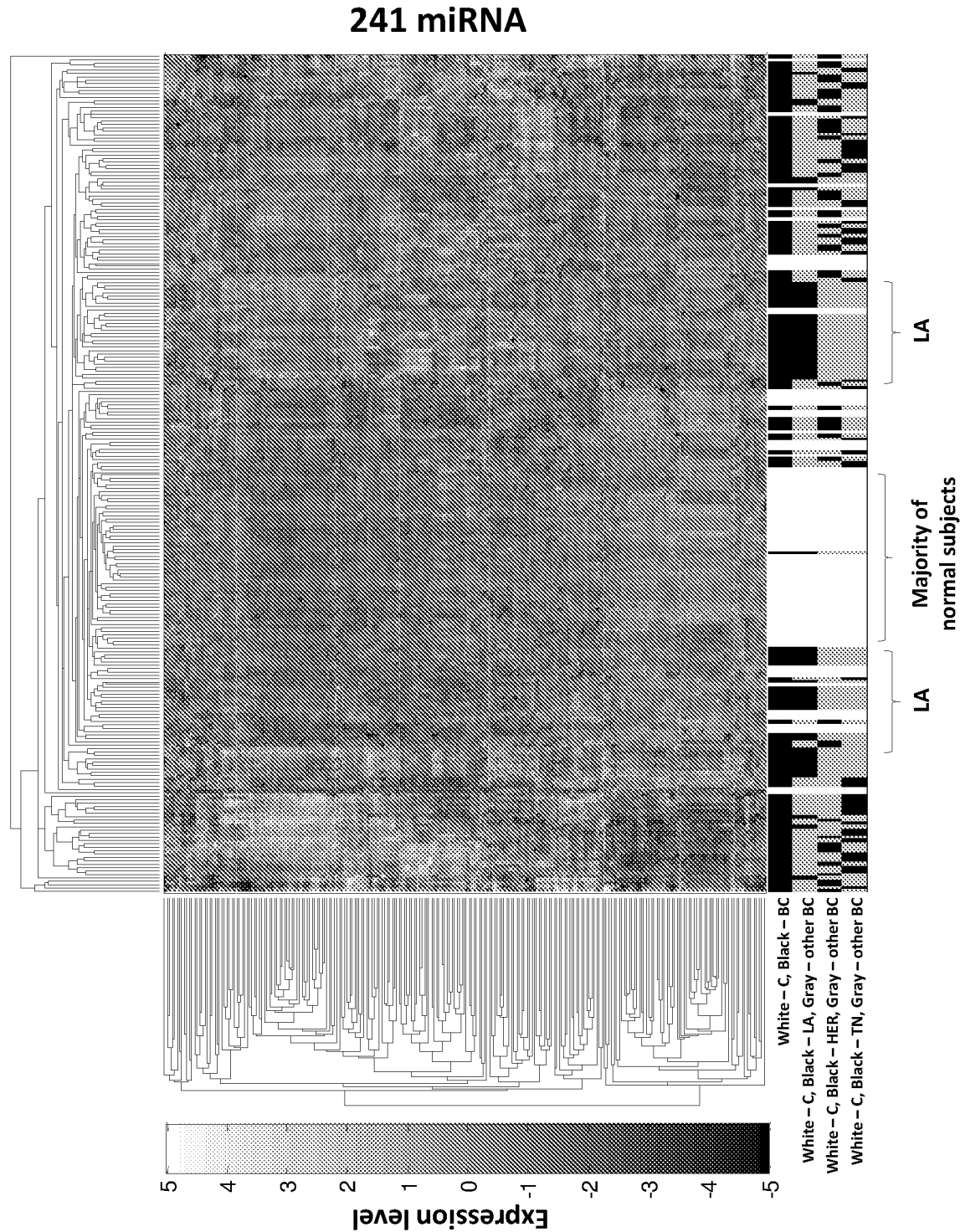
FIG. 3 shows an expression level heat-map of all reliable detected miRNAs. The heat-map representation of all reliably detected miRNAs (Table 4); the expression levels (copy/ml) of miRNAs were presented in log2 scale and standardized to zero mean. The colour of the points represented the concentrations. Hierarchical clustering was carried out for both dimensions (the miRNAs and the samples) based on the Euclidean distance. For the horizon dimension, various colours were used to represent the various types of subjects. C—control (cancer free (normal) subjects), BC—all breast cancer subjects, LA—luminal A subtype, HER—Her2 subtype, TN—triple negative subtype.

A heat-map was then constructed to represent the expression levels of all 241 detected serum miRNAs (FIG. 3). Based on the unsupervised hierarchical clustering, most of the control subjects were grouped together, indicating that the miRNA profile in the serum of breast cancer subjects were different from those in the serum of normal, cancer-free subjects. Closer examining the revealing that the luminal A (LA) subtype were also grouped together among all the breast cancer subjects (FIG. 3, the second row of horizon indicator).

Figure 4:
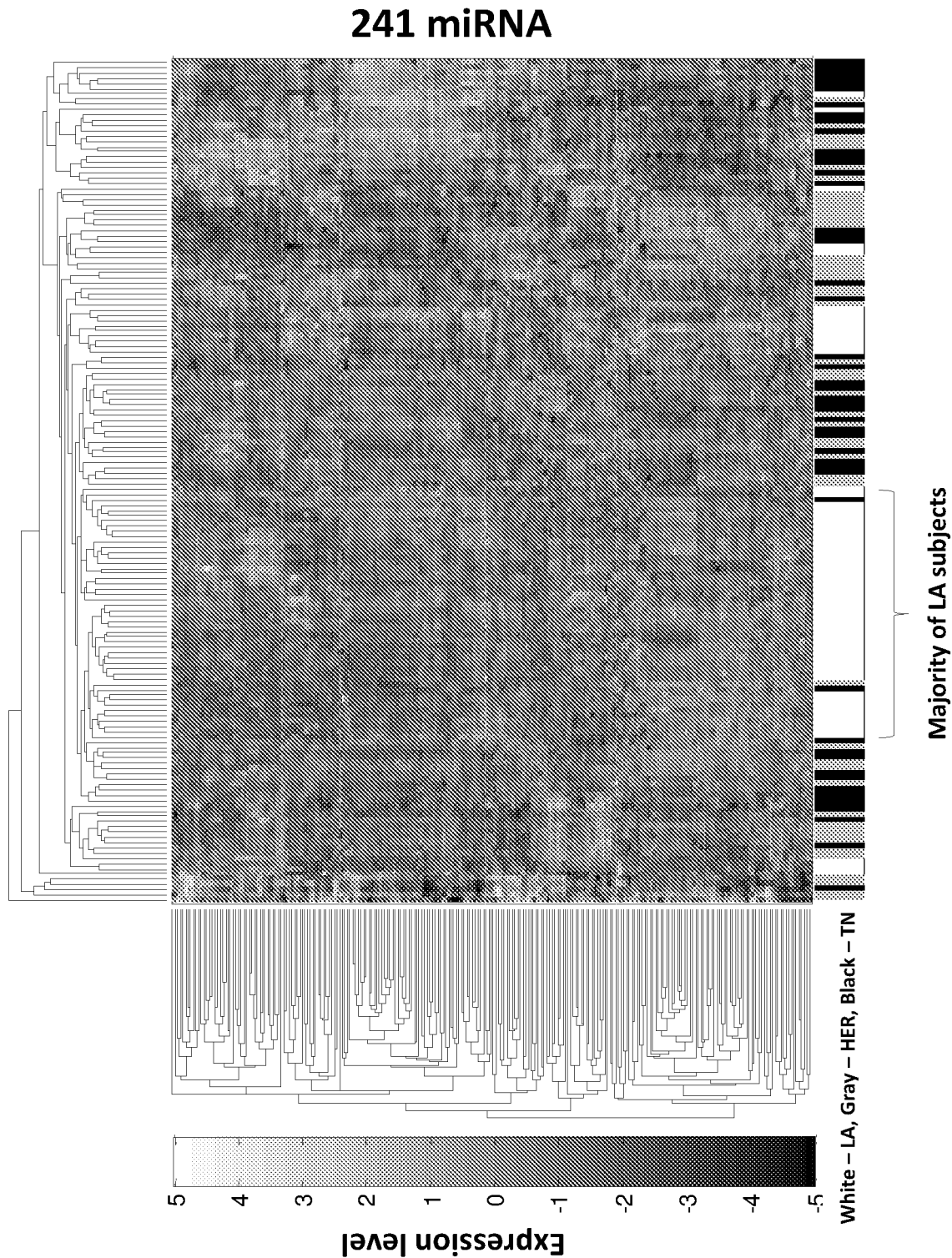
FIG. 4 shows an expression level heat-map of all miRNAs between three subtypes of breast cancer subjects. The heat-map representation of all reliable detectable miRNAs (Table 4) in three subtypes of breast cancer subjects; the expression levels (copy/ml) of miRNAs were presented in log2 scale and standardized to zero mean. The gray-scale represented the concentrations of miRNA. Hierarchical clustering was carried out for both dimensions (the miRNAs and the samples) based on the Euclidean distance. For the horizon dimension, various colours were used to represent the various types of subjects. LA—luminal A subtype, HER—Her2 subtype, TN—triple negative subtype.

Excluding all the control subjects, the heat-map for three subtypes of breast cancer were constructed based on all 241 detected serum miRNAs (FIG. 4) to examine the difference between various subtypes of breast cancer. Most of the luminal A (LA) subtype subjects were clearly clustered together in a focused region based on the unsupervised hierarchical clustering while the other two subtypes were mixed together in the other regions. Those results showed that there is some distinction between the luminal A (LA) subtype and the other two remaining subtypes (TN and HER) in terms of serum miRNA profile.

The expression levels of the 241 serum miRNAs were then compared between normal (cancer-free) and breast cancer groups, whereby individual subtypes or all subtypes were grouped together. Significance in differential expressions between two groups was calculated based on the t-test (p-value<0.01), further corrected for false discovery rate (FDR) estimation using Bonferroni-type multiple comparison procedures.

Sera from patients clinically confirmed to have either one of the breast cancers subtypes (LA, HER or TN subtype) were grouped together and compared to sera from normal (cancer-free) donors. Noticing the difference between various subtypes, a comparison was also made between each subtype of breast cancer and normal, meaning that, for example, first, the breast cancer subtypes (LA+HER+TN) were compared to normal, cancer-free samples. Next, each of the subtypes were individually compared to normal cancer free samples, that is LA vs normal, cancer-free; HER vs normal, cancer-free; and TN vs normal, cancer-free. The number of significant miRNAs for various comparisons is summarized in Table 5.

TABLE 5

Number of differentially expressed microRNAs

| | All | | | Upregulated | | | Downregulated | | |
|---|---|---|---|---|---|---|---|---|---|
| | p < 0.01 | p < 0.001 | p < 0.0001 | p < 0.01 | p < 0.001 | p < 0.0001 | p < 0.01 | p < 0.001 | p < 0.0001 |
| C vs. BC | 161 | 139 | 118 | 101 | 89 | 74 | 60 | 50 | 44 |
| C vs. LA | 132 | 106 | 83 | 89 | 72 | 60 | 43 | 34 | 23 |
| C vs. HER | 141 | 112 | 82 | 92 | 75 | 58 | 49 | 37 | 24 |
| C vs. TN | 143 | 121 | 106 | 86 | 72 | 62 | 57 | 49 | 44 |

The number of differentially expressed microRNAs for various forms of comparisons; C—control, LA—luminal A subtype, HER—Her2 subtype, TN—triple negative subtype. The p-values were adjusted for false discovery rate correction using Bonferroni method.

A pool of 161 miRNAs that showed significant differential expression between control and all cancers was identified (p-value <0.01; Table 6, C v.s BC). Consistent with other reports (Table 1), the present study demonstrated that more miRNAs were upregulated (total number of upregulated miRNAs: 101) in cancer subjects compared to 60 downregulated miRNAs (Table 5). However, the number of differentially expressed miRNAs validated by qPCR in the study, which is 161 miRNAs was significantly higher than previously reported (in Table 6, C v.s BC total 63). Thus, the experimental design outlined herein enabled the identification of more regulated biomarkers.

TABLE 6

Differentially expressed microRNAs between control and breast cancer subjects.

| SEQ ID NO: | Name | C vs. LA Regulation | FC | C vs. HER Regulation | FC | C vs. TN Regulation | FC | C vs. All BC Regulation | FC |
|---|---|---|---|---|---|---|---|---|---|
| 221 | hsa-miR-618 | Up | 1.8 | Up | 2.3 | Up | 2.4 | Up | 2.1 |
| 219 | hsa-miR-616-3p | Up | 1.3 | Up | 1.6 | Up | 1.4 | Up | 1.4 |
| 222 | hsa-miR-627 | Up | 1.6 | Up | 1.5 | Up | 1.6 | Up | 1.6 |
| 179 | hsa-miR-411-3p | Down | 0.7 | Down | 0.6 | Down | 0.5 | Down | 0.6 |
| 217 | hsa-miR-589-5p | Up | 1.3 | Up | 1.2 | Up | 1.2 | Up | 1.2 |
| 194 | hsa-miR-4732-3p | Up | 1.5 | Up | 1.9 | Up | 1.9 | Up | 1.7 |
| 201 | hsa-miR-487b | Down | 0.5 | Down | 0.6 | Down | 0.4 | Down | 0.5 |
| 157 | hsa-miR-339-3p | Down | 0.7 | Down | 0.7 | Down | 0.6 | Down | 0.7 |
| 169 | hsa-miR-370 | Down | 0.6 | Down | 0.6 | Down | 0.4 | Down | 0.5 |
| 102 | hsa-miR-214-3p | Up | 1.4 | Up | 1.9 | Up | 1.5 | Up | 1.5 |
| 208 | hsa-miR-501-5p | Up | 1.7 | Up | 1.8 | Up | 2.2 | Up | 1.9 |
| 176 | hsa-miR-378a-5p | Up | 1.7 | Up | 1.6 | Up | 2.0 | Up | 1.8 |
| 75 | hsa-miR-183-5p | Up | 1.6 | Up | 1.8 | Up | 2.5 | Up | 1.9 |
| 73 | hsa-miR-181d | Down | 0.6 | Down | 0.8 | Down | 0.6 | Down | 0.7 |
| 62 | hsa-miR-154-5p | Down | 0.6 | Down | 0.5 | Down | 0.3 | Down | 0.5 |
| 33 | hsa-miR-1291 | Up | 1.5 | Up | 2.0 | Up | 2.0 | Up | 1.8 |
| 82 | hsa-miR-192-5p | Up | 1.4 | Up | 1.6 | Up | 1.9 | Up | 1.6 |
| 128 | hsa-miR-29b-2-5p | Up | 1.3 | Up | 1.1 | Up | 1.3 | Up | 1.3 |
| 32 | hsa-miR-1285-3p | Up | 1.4 | Up | 1.5 | Up | 1.7 | Up | 1.5 |
| 110 | hsa-miR-224-5p | Down | 0.7 | Down | 0.7 | Down | 0.7 | Down | 0.7 |
| 215 | hsa-miR-576-5p | Up | 1.3 | Up | 1.6 | Up | 2.2 | Up | 1.6 |
| 173 | hsa-miR-375 | Down | 0.5 | Down | 0.5 | Down | 0.5 | Down | 0.5 |
| 131 | hsa-miR-29c-5p | Up | 1.2 | Up | 1.4 | Up | 1.4 | Up | 1.3 |
| 2 | hsa-let-7b-3p | Up | 1.3 | Up | 1.3 | Up | 1.3 | Up | 1.3 |
| 203 | hsa-miR-493-5p | Down | 0.7 | Down | 0.5 | Down | 0.5 | Down | 0.6 |
| 235 | hsa-miR-93-3p | Up | 1.5 | Up | 1.3 | Up | 1.5 | Up | 1.4 |
| 113 | hsa-miR-23a-5p | Up | 1.4 | Up | 1.3 | Up | 1.4 | Up | 1.4 |
| 164 | hsa-miR-362-3p | Up | 1.5 | Up | 1.4 | Up | 1.6 | Up | 1.5 |
| 84 | hsa-miR-193b-3p | Up | 1.6 | Up | 1.7 | Up | 1.5 | Up | 1.6 |
| 98 | hsa-miR-206 | Up | 2.9 | Up | 4.0 | Up | 4.0 | Up | 3.5 |
| 237 | hsa-miR-96-5p | Up | 1.5 | Up | 2.0 | Up | 2.3 | Up | 1.9 |
| 29 | hsa-miR-127-3p | Down | 0.7 | Down | 0.5 | Down | 0.4 | Down | 0.5 |
| 178 | hsa-miR-409-3p | Down | 0.2 | Down | 0.6 | Down | 0.4 | Down | 0.4 |
| 155 | hsa-miR-337-5p | Down | 0.6 | Down | 0.6 | Down | 0.4 | Down | 0.5 |
| 146 | hsa-miR-324-5p | Down | 0.7 | Down | 0.7 | Down | 0.7 | Down | 0.7 |
| 148 | hsa-miR-326 | Down | 0.6 | Down | 0.7 | Down | 0.5 | Down | 0.6 |
| 47 | hsa-miR-143-3p | Up | 1.9 | Up | 2.1 | Up | 2.5 | Up | 2.1 |
| 145 | hsa-miR-324-3p | Up | 1.3 | Up | 1.4 | Up | 1.4 | Up | 1.3 |
| 65 | hsa-miR-15b-3p | Up | 1.3 | Up | 1.5 | Up | 1.9 | Up | 1.5 |
| 212 | hsa-miR-532-5p | Up | 1.3 | Up | 1.7 | Up | 1.8 | Up | 1.6 |
| 166 | hsa-miR-363-3p | Up | 1.8 | Up | 1.6 | Up | 2.1 | Up | 1.8 |
| 150 | hsa-miR-330-3p | Down | 0.8 | Down | 0.8 | Down | 0.6 | Down | 0.7 |
| 20 | hsa-miR-10a-5p | Up | 1.2 | Up | 1.4 | Up | 1.2 | Up | 1.3 |
| 209 | hsa-miR-502-3p | Up | 1.9 | Up | 1.4 | Up | 1.6 | Up | 1.7 |
| 130 | hsa-miR-29c-3p | Up | 1.4 | Up | 1.7 | Up | 1.9 | Up | 1.7 |

TABLE 6-continued

Differentially expressed microRNAs between control and breast cancer subjects.

| SEQ ID NO: | Name | C vs. LA Regulation | FC | C vs. HER Regulation | FC | C vs. TN Regulation | FC | C vs. All BC Regulation | FC |
|---|---|---|---|---|---|---|---|---|---|
| 158 | hsa-miR-339-5p | Down | 0.8 | Down | 0.6 | Down | 0.5 | Down | 0.6 |
| 175 | hsa-miR-378a-3p | Up | 1.5 | Up | 1.7 | Up | 1.6 | Up | 1.6 |
| 186 | hsa-miR-4306 | Up | 1.5 | Up | 1.4 | Up | 1.5 | Up | 1.5 |
| 12 | hsa-miR-1 | Up | 2.4 | Up | 2.7 | Up | 2.2 | Up | 2.4 |
| 59 | hsa-miR-151a-3p | Down | 0.8 | Down | 0.7 | Down | 0.7 | Down | 0.7 |
| 129 | hsa-miR-29b-3p | Up | 1.3 | Up | 1.3 | Up | 1.4 | Up | 1.3 |
| 100 | hsa-miR-20b-5p | Up | 1.8 | Up | 1.9 | Up | 2.5 | Up | 2.0 |
| 68 | hsa-miR-17-3p | Up | 1.6 | Up | 1.3 | Up | 1.4 | Up | 1.5 |
| 216 | hsa-miR-584-5p | Down | 0.8 | Down | 0.8 | Down | 0.7 | Down | 0.8 |
| 224 | hsa-miR-629-5p | Up | 1.4 | Up | 1.7 | Up | 1.5 | Up | 1.5 |
| 26 | hsa-miR-125b-5p | Up | 2.3 | Up | 1.9 | Up | 2.5 | Up | 2.2 |
| 171 | hsa-miR-374a-5p | Down | 0.7 | Up | 2.1 | Up | 2.3 | Up | 1.4 |
| 38 | hsa-miR-133a | Up | 3.1 | Up | 2.1 | Up | 2.1 | Up | 2.4 |
| 60 | hsa-miR-151a-5p | Down | 0.7 | Down | 0.6 | Down | 0.6 | Down | 0.7 |
| 228 | hsa-miR-660-5p | Up | 1.6 | Up | 1.7 | Up | 1.8 | Up | 1.7 |
| 123 | hsa-miR-27b-3p | Down | 0.8 | Down | 0.8 | Down | 0.8 | Down | 0.8 |
| 92 | hsa-miR-199b-3p | Down | 0.8 | Down | 0.8 | Down | 0.8 | Down | 0.8 |
| 77 | hsa-miR-186-5p | Up | 1.5 | Up | 1.4 | Up | 1.3 | Up | 1.4 |
| 21 | hsa-miR-10b-5p | Up | 1.3 | Up | 1.8 | Up | 1.5 | Up | 1.5 |
| 91 | hsa-miR-199a-5p | Down | 0.8 | Down | 0.6 | Down | 0.6 | Down | 0.7 |
| 13 | hsa-miR-101-3p | Up | 2.7 | Up | 1.8 | Up | 2.0 | Up | 2.2 |
| 117 | hsa-miR-25-3p | Up | 1.9 | Up | 1.9 | Up | 2.2 | Up | 2.0 |
| 236 | hsa-miR-93-5p | Up | 1.2 | Up | 1.3 | Up | 1.3 | Up | 1.3 |
| 76 | hsa-miR-185-5p | Up | 1.4 | Up | 1.3 | Up | 1.2 | Up | 1.3 |
| 93 | hsa-miR-19a-3p | Up | 1.3 | Up | 1.9 | Up | 2.1 | Up | 1.7 |
| 140 | hsa-miR-320a | Up | 1.4 | Up | 1.3 | Up | 1.3 | Up | 1.3 |
| 1 | hsa-let-7a-5p | Down | 0.8 | Down | 0.5 | Down | 0.5 | Down | 0.6 |
| 64 | hsa-miR-15a-5p | Up | 1.4 | Up | 1.2 | Up | 1.4 | Up | 1.3 |
| 94 | hsa-miR-19b-3p | Up | 1.4 | Up | 1.9 | Up | 2.3 | Up | 1.8 |
| 143 | hsa-miR-320d | Up | 1.2 | Up | 1.3 | Up | 1.3 | Up | 1.3 |
| 99 | hsa-miR-20a-5p | Up | 1.3 | Up | 1.4 | Up | 1.8 | Up | 1.5 |
| 233 | hsa-miR-92a-3p | Up | 1.4 | Up | 1.3 | Up | 1.4 | Up | 1.4 |
| 200 | hsa-miR-486-5p | Up | 1.8 | Up | 1.9 | Up | 2.0 | Up | 1.9 |
| 67 | hsa-miR-16-5p | Up | 1.4 | Up | 1.8 | Up | 2.3 | Up | 1.8 |
| 190 | hsa-miR-451a | Up | 2.1 | Up | 1.9 | Up | 2.9 | Up | 2.2 |
| 24 | hsa-miR-124-5p | Down | 0.6 | No change | | Down | 0.8 | Down | 0.8 |
| 162 | hsa-miR-34b-5p | No change | | Up | 1.7 | Up | 1.8 | Up | 1.5 |
| 220 | hsa-miR-616-5p | Up | 1.4 | No change | | Up | 1.7 | Up | 1.4 |
| 87 | hsa-miR-196a-5p | No change | | Up | 1.7 | Up | 2.1 | Up | 1.6 |
| 223 | hsa-miR-629-3p | No change | | Up | 1.4 | Up | 1.4 | Up | 1.3 |
| 229 | hsa-miR-668 | Down | 0.6 | No change | | Down | 0.5 | Down | 0.6 |
| 218 | hsa-miR-596 | No change | | Up | 2.3 | Up | 1.5 | Up | 1.6 |
| 198 | hsa-miR-485-3p | Down | 0.6 | No change | | Down | 0.5 | Down | 0.6 |
| 206 | hsa-miR-500a-3p | Up | 2.2 | No change | | Up | 1.4 | Up | 1.6 |
| 168 | hsa-miR-369-5p | No change | | Down | 0.5 | Down | 0.5 | Down | 0.6 |
| 115 | hsa-miR-23c | No change | | Down | 0.7 | Down | 0.7 | Down | 0.8 |
| 225 | hsa-miR-650 | Up | 1.6 | Up | 2.0 | No change | | Up | 1.6 |
| 180 | hsa-miR-411-5p | No change | | Down | 0.6 | Down | 0.5 | Down | 0.7 |
| 126 | hsa-miR-299-3p | No change | | Down | 0.7 | Down | 0.5 | Down | 0.7 |
| 40 | hsa-miR-136-3p | Down | 0.6 | No change | | Down | 0.6 | Down | 0.6 |
| 34 | hsa-miR-1299 | Up | 1.6 | Up | 1.8 | No change | | Up | 1.6 |
| 188 | hsa-miR-432-5p | No change | | Down | 0.5 | Down | 0.4 | Down | 0.6 |
| 16 | hsa-miR-106b-3p | Up | 1.2 | Up | 1.2 | No change | | Up | 1.1 |
| 213 | hsa-miR-551b-3p | No change | | Down | 0.6 | Down | 0.5 | Down | 0.6 |
| 207 | hsa-miR-500a-5p | No change | | Up | 1.8 | Up | 2.2 | Up | 1.7 |
| 211 | hsa-miR-532-3p | Up | 1.2 | Up | 1.2 | No change | | Up | 1.2 |
| 74 | hsa-miR-1825 | Up | 1.7 | Up | 1.6 | No change | | Up | 1.5 |
| 174 | hsa-miR-376a-5p | No change | | Down | 0.6 | Down | 0.5 | Down | 0.7 |
| 189 | hsa-miR-450a-5p | No change | | Up | 1.6 | Up | 1.6 | Up | 1.5 |
| 14 | hsa-miR-101-5p | No change | | Up | 2.2 | Up | 1.8 | Up | 1.5 |
| 138 | hsa-miR-30e-3p | No change | | Down | 0.8 | Down | 0.8 | Down | 0.9 |
| 86 | hsa-miR-195-5p | No change | | Up | 1.8 | Up | 1.8 | Up | 1.5 |
| 154 | hsa-miR-337-3p | No change | | Down | 0.6 | Down | 0.5 | Down | 0.6 |
| 136 | hsa-miR-30d-3p | Down | 0.6 | No change | | Down | 0.8 | Down | 0.8 |
| 125 | hsa-miR-28-5p | No change | | Down | 0.6 | Down | 0.6 | Down | 0.7 |
| 167 | hsa-miR-365a-3p | No change | | Up | 1.9 | Up | 2.1 | Up | 1.6 |
| 205 | hsa-miR-499a-5p | No change | | Up | 2.2 | Up | 1.6 | Up | 1.6 |
| 187 | hsa-miR-431-5p | No change | | Down | 0.6 | Down | 0.4 | Down | 0.6 |
| 49 | hsa-miR-144-5p | Up | 1.4 | No change | | Up | 1.8 | Up | 1.4 |
| 41 | hsa-miR-136-5p | No change | | Down | 0.5 | Down | 0.4 | Down | 0.5 |
| 80 | hsa-miR-18b-5p | No change | | Up | 1.3 | Up | 1.4 | Up | 1.2 |
| 43 | hsa-miR-140-3p | No change | | Up | 1.9 | Up | 2.2 | Up | 1.6 |
| 238 | hsa-miR-98 | No change | | Down | 0.6 | Down | 0.5 | Down | 0.7 |

TABLE 6-continued

Differentially expressed microRNAs between control and breast cancer subjects.

| SEQ ID NO: | Name | C vs. LA Regulation | FC | C vs. HER Regulation | FC | C vs. TN Regulation | FC | C vs. All BC Regulation | FC |
|---|---|---|---|---|---|---|---|---|---|
| 18 | hsa-miR-107 | No change | | Down | 0.7 | Down | 0.8 | Down | 0.8 |
| 89 | hsa-miR-197-3p | Up | 1.4 | Up | 1.2 | No change | | Up | 1.2 |
| 184 | hsa-miR-425-5p | Up | 1.3 | No change | | Up | 1.2 | Up | 1.2 |
| 5 | hsa-let-7d-5p | No change | | Down | 0.6 | Down | 0.5 | Down | 0.7 |
| 127 | hsa-miR-29a-3p | Up | 1.5 | No change | | Up | 1.5 | Up | 1.4 |
| 51 | hsa-miR-146a-5p | No change | | Down | 0.8 | Down | 0.7 | Down | 0.8 |
| 52 | hsa-miR-146b-5p | No change | | Down | 0.7 | Down | 0.6 | Down | 0.8 |
| 112 | hsa-miR-23a-3p | No change | | Down | 0.6 | Down | 0.6 | Down | 0.8 |
| 181 | hsa-miR-423-5p | No change | | Up | 1.4 | Up | 1.2 | Up | 1.2 |
| 17 | hsa-miR-106b-5p | No change | | Up | 1.6 | Up | 1.9 | Up | 1.4 |
| 121 | hsa-miR-27a-3p | No change | | Down | 0.8 | Down | 0.7 | Down | 0.8 |
| 109 | hsa-miR-22-3p | Up | 1.2 | No change | | Up | 1.4 | Up | 1.2 |
| 48 | hsa-miR-144-3p | No change | | Up | 2.6 | Up | 2.9 | Up | 2.1 |
| 105 | hsa-miR-221-3p | Down | 0.8 | No change | | Down | 0.8 | Down | 0.9 |
| 3 | hsa-let-7b-5p | Up | 1.5 | No change | | Up | 1.6 | Up | 1.3 |
| 15 | hsa-miR-103a-3p | No change | | Down | 0.8 | Down | 0.8 | Down | 0.9 |
| 141 | hsa-miR-320b | No change | | Up | 1.4 | Up | 1.2 | Up | 1.2 |
| 69 | hsa-miR-17-5p | Up | 1.4 | No change | | Up | 1.7 | Up | 1.4 |
| 8 | hsa-let-7f-5p | No change | | Down | 0.6 | Down | 0.5 | Down | 0.7 |
| 214 | hsa-miR-573 | Up | 2.2 | No change | | No change | | Up | 1.6 |
| 23 | hsa-miR-1226-3p | Down | 0.6 | No change | | No change | | Down | 0.7 |
| 199 | hsa-miR-485-5p | No change | | No change | | Down | 0.5 | Down | 0.6 |
| 106 | hsa-miR-221-5p | No change | | Down | 0.7 | Down | 0.8 | No change | |
| 226 | hsa-miR-651 | Down | 0.5 | Up | 1.7 | No change | | No change | |
| 177 | hsa-miR-382-5p | No change | | No change | | Down | 0.4 | Down | 0.6 |
| 160 | hsa-miR-342-5p | Down | 0.5 | No change | | No change | | Down | 0.8 |
| 165 | hsa-miR-362-5p | Up | 1.3 | No change | | No change | | Up | 1.2 |
| 96 | hsa-miR-200c-3p | Down | 0.7 | No change | | No change | | Down | 0.8 |
| 149 | hsa-miR-328 | No change | | No change | | Down | 0.8 | Down | 0.9 |
| 195 | hsa-miR-483-3p | No change | | Up | 1.6 | No change | | Up | 1.3 |
| 124 | hsa-miR-28-3p | Down | 0.8 | No change | | No change | | Down | 0.9 |
| 147 | hsa-miR-32-5p | No change | | Up | 1.5 | No change | | Up | 1.4 |
| 182 | hsa-miR-424-5p | Up | 1.6 | No change | | No change | | Up | 1.3 |
| 172 | hsa-miR-374b-5p | Up | 2.0 | No change | | No change | | Up | 1.3 |
| 183 | hsa-miR-425-3p | Down | 0.9 | No change | | No change | | Down | 0.9 |
| 241 | hsa-miR-99b-5p | No change | | No change | | Down | 0.7 | Down | 0.8 |
| 163 | hsa-miR-361-5p | Up | 1.3 | No change | | No change | | Up | 1.1 |
| 90 | hsa-miR-199a-3p | Down | 0.8 | No change | | No change | | Down | 0.8 |
| 53 | hsa-miR-148a-3p | Up | 1.4 | No change | | No change | | Up | 1.3 |
| 83 | hsa-miR-193a-5p | No change | | Up | 1.5 | No change | | Up | 1.2 |
| 50 | hsa-miR-145-5p | Up | 1.4 | No change | | No change | | Up | 1.3 |
| 36 | hsa-miR-130b-3p | Up | 1.1 | No change | | No change | | Up | 1.1 |
| 230 | hsa-miR-720 | No change | | Up | 2.0 | No change | | Up | 1.3 |
| 66 | hsa-miR-15b-5p | Up | 1.3 | Down | 0.8 | No change | | No change | |
| 103 | hsa-miR-21-5p | Up | 1.4 | No change | | No change | | Up | 1.2 |
| 193 | hsa-miR-454-5p | No change | | No change | | Up | 1.5 | No change | |
| 54 | hsa-miR-148a-5p | No change | | Up | 1.2 | No change | | No change | |
| 240 | hsa-miR-99b-3p | No change | | No change | | Down | 0.8 | No change | |
| 151 | hsa-miR-331-5p | Up | 1.3 | No change | | No change | | No change | |
| 70 | hsa-miR-181a-2-3p | Up | 1.2 | No change | | No change | | No change | |
| 19 | hsa-miR-10a-3p | Up | 1.3 | No change | | No change | | No change | |
| 156 | hsa-miR-338-5p | Up | 1.6 | No change | | No change | | No change | |
| 152 | hsa-miR-335-3p | Down | 0.7 | No change | | No change | | No change | |
| 37 | hsa-miR-130b-5p | Down | 0.9 | No change | | No change | | No change | |
| 191 | hsa-miR-452-5p | No change | | Up | 1.3 | No change | | No change | |
| 7 | hsa-let-7f-1-3p | No change | | Up | 1.3 | No change | | No change | |
| 231 | hsa-miR-874 | No change | | No change | | Up | 1.5 | No change | |
| 104 | hsa-miR-219-5p | Down | 0.8 | No change | | No change | | No change | |
| 31 | hsa-miR-1280 | Up | 1.2 | No change | | No change | | No change | |
| 161 | hsa-miR-34a-5p | No change | | Up | 1.3 | No change | | No change | |
| 232 | hsa-miR-885-5p | Down | 0.6 | No change | | No change | | No change | |
| 45 | hsa-miR-141-3p | No change | | Up | 1.4 | No change | | No change | |
| 239 | hsa-miR-99a-5p | Up | 1.2 | No change | | No change | | No change | |
| 134 | hsa-miR-30b-5p | Up | 1.2 | No change | | No change | | No change | |
| 44 | hsa-miR-140-5p | No change | | No change | | Up | 1.2 | No change | |
| 192 | hsa-miR-454-3p | No change | | No change | | Up | 1.3 | No change | |
| 81 | hsa-miR-191-5p | No change | | No change | | Down | 0.9 | No change | |
| 159 | hsa-miR-340-5p | No change | | No change | | No change | | Up | 1.2 |
| 144 | hsa-miR-320e | No change | | Up | 1.5 | No change | | No change | |
| 79 | hsa-miR-18a-5p | Up | 1.6 | No change | | No change | | No change | |
| 139 | hsa-miR-30e-5p | No change | | No change | | Up | 1.3 | No change | |
| 107 | hsa-miR-222-3p | No change | | Down | 0.8 | No change | | No change | |

TABLE 6-continued

Differentially expressed microRNAs between control and breast cancer subjects.

| SEQ ID NO: | Name | C vs. LA Regulation | FC | C vs. HER Regulation | FC | C vs. TN Regulation | FC | C vs. All BC Regulation | FC |
|---|---|---|---|---|---|---|---|---|---|
| 137 | hsa-miR-30d-5p | Down | 0.9 | No change | | No change | | No change | |
| 120 | hsa-miR-26b-5p | Up | 1.3 | No change | | No change | | No change | |
| 11 | hsa-let-7i-5p | No change | | Down | 0.8 | No change | | No change | |
| 35 | hsa-miR-130a-3p | Down | 0.8 | No change | | No change | | No change | |
| 118 | hsa-miR-26a-5p | No change | | Down | 0.8 | No change | | No change | |
| 142 | hsa-miR-320c | No change | | Up | 1.4 | No change | | No change | |
| 116 | hsa-miR-24-3p | No change | | Up | 1.2 | No change | | No change | |

For the comparison between normal (cancer-free) and all breast cancer subjects (C vs. All BC), noinial (cancer-free) and luminal A subtype of breast subjects (C vs. LA), normal (cancer-free) and her2 subtype of breast subjects (C vs. HER), normal (cancer-free) and triple negative subtype of breast subjects (C vs. TN), those miRNAs had p-values lower than 0.01 after false discovery rate correction (Bonferroni method) were shown. FC (fold change)—the mean expression level (copy/ml) of miRNA in the cancer population divided by that in the normal, cancer-free population. BC—breast cancer, LA—luminal A subtype, HER—Her2 subtype, TN—triple negative subtype. Regulation—the direction of change in the latter group compared to former group in all comparisons. MiRNAs with p-value higher than 0.01 were considered not changed (no change).

Of the total 63 miRNAs had been previously reported (Table 1), three of them had been removed from the later version of miRBase, another miRNA was not found in any version of miRBase and another three miRNAs showed contradictory observations on the direction of change in the cancer subjects (hsa-miR-145-5p, hsa-miR-133a, hsa-miR-92a-3p) (Table 7). Comparing the previous results in Table 6, C v.s BC, with the remaining 56 miRNAs, only 16 miRNAs (hsa-miR-21-5p, hsa-miR-10b-5p, hsa-miR-16-5p, hsa-miR-195-5p, hsa-miR-1, hsa-miR-125b-5p, hsa-miR-15a-5p, hsa-miR-214-3p, hsa-miR-25-3p, hsa-miR-29a-3p, hsa-miR-324-3p, hsa-miR-423-5p, hsa-miR-425-5p, hsa-miR-451a, hsa-miR-589-5p, hsa-miR-93-5p) were found to be commonly upregulated and two miRNAs (hsa-miR-199a-5p and hsa-miR-411-5p) were found to be commonly downregulated (Table 7). The rests of the reported miRNAs were either found to be unchanged or changed in a different direction. Thus, the majority of the purported differentially regulated miRNAs in the literature were not confirmed in the present study. Interestingly, identified 143 novel miRNAs have been identified as potential biomarkers for breast cancers.

TABLE 7

Comparison between the current study and other literature reports

| SEQ ID NO: | Name in literature | Name in miRBase v18 | No. of literature | Regulation in literature | Regulation in this study |
|---|---|---|---|---|---|
| 103 | miR-21 | hsa-miR-21-5p | 7 | Upregulated | Upregulated |
| — | miR-155 | hsa-miR-155-5p | 5 | Upregulated | N.D. |
| 21 | miR-10b | hsa-miR-10b-5p | 2 | Upregulated | Upregulated |
| 51 | miR-146a | hsa-miR-146a-5p | 2 | Upregulated | Downregulated |
| 55 | miR-148b | hsa-miR-148b-3p | 2 | Upregulated | No change |
| 67 | miR-16 | hsa-miR-16-5p | 2 | Upregulated | Upregulated |
| 86 | miR-195 | hsa-miR-195-5p | 2 | Upregulated | Upregulated |
| 107 | miR-222 | hsa-miR-222-3p | 2 | Upregulated | No change |
| 161 | miR-34a | hsa-miR-34a-5p | 2 | Upregulated | No change |
| — | miR-376c | hsa-miR-376c | 2 | Upregulated | N.D. |
| 178 | miR-409-3p | hsa-miR-409-3p | 2 | Upregulated | Downregulated |
| 1 | let-7a | hsa-let-7a-5p | 1 | Upregulated | Downregulated |
| 12 | miR-1 | hsa-miR-1 | 1 | Upregulated | Upregulated |
| — | miR-106a | hsa-miR-106a-5p | 1 | Upregulated | N.D. |
| 18 | miR-107 | hsa-miR-107 | 1 | Upregulated | Downregulated |
| 26 | miR-125b | hsa-miR-125b-5p | 1 | Upregulated | Upregulated |
| 29 | miR-127-3p | hsa-miR-127-3p | 1 | Upregulated | Downregulated |
| — | miR-133b | hsa-miR-133b | 1 | Upregulated | N.D. |
| — | miR-138 | hsa-miR-138-5p | 1 | Upregulated | N.D. |
| — | miR-142-3p | hsa-miR-142-3p | 1 | Upregulated | N.D. |
| 64 | miR-15a | hsa-miR-15a-5p | 1 | Upregulated | Upregulated |
| — | miR-182 | hsa-miR-182-5p | 1 | Upregulated | N.D. |
| 79 | miR-18a | hsa-miR-18a-5p | 1 | Upregulated | No change |
| 81 | miR-191 | hsa-miR-191-5p | 1 | Upregulated | No change |
| — | miR-202 | hsa-miR-202-3p | 1 | Upregulated | N.D. |
| 102 | miR-214 | hsa-miR-214-3p | 1 | Upregulated | Upregulated |
| 117 | miR-25 | hsa-miR-25-3p | 1 | Upregulated | Upregulated |
| 127 | miR-29a | hsa-miR-29a-3p | 1 | Upregulated | Upregulated |
| 145 | miR-324-3p | hsa-miR-324-3p | 1 | Upregulated | Upregulated |
| — | miR-373 | hsa-miR-373-3p | 1 | Upregulated | N.D. |

TABLE 7-continued

Comparison between the current study and other literature reports

| SEQ ID NO: | Name in literature | Name in miRBase v18 | No. of literature | Regulation in literature | Regulation in this study |
|---|---|---|---|---|---|
| — | miR-376a | hsa-miR-376a-3p | 1 | Upregulated | N.D. |
| 177 | miR-382 | hsa-miR-382-5p | 1 | Upregulated | Downregulated |
| 181 | miR-423-5p | hsa-miR-423-5p | 1 | Upregulated | Upregulated |
| 183 | miR-425* | hsa-miR-425-3p | 1 | Upregulated | Downregulated |
| 184 | miR-425 | hsa-miR-425-5p | 1 | Upregulated | Upregulated |
| 190 | miR-451 | hsa-miR-451a | 1 | Upregulated | Upregulated |
| 191 | miR-452 | hsa-miR-452-5p | 1 | Upregulated | No change |
| 217 | miR-589 | hsa-miR-589-5p | 1 | Upregulated | Upregulated |
| 227 | miR-652 | hsa-miR-652-3p | 1 | Upregulated | No change |
| 236 | miR-93 | hsa-miR-93-5p | 1 | Upregulated | Upregulated |
| 3 | let-7b | hsa-let-7b-5p | 1 | Downregulated | Upregulated |
| — | let-7c | hsa-let-7c | 1 | Downregulated | N.D. |
| 27 | miR-126 | hsa-miR-126-3p | 1 | Downregulated | No change |
| 42 | miR-139-5p | hsa-miR-139-5p | 1 | Downregulated | No change |
| 47 | miR-143 | hsa-miR-143-3p | 1 | Downregulated | Upregulated |
| 71 | miR-181a | hsa-miR-181a-5p | 1 | Downregulated | No change |
| 91 | miR-199a | hsa-miR-199a-5p | 1 | Downregulated | Downregulated |
| 97 | miR-205 | hsa-miR-205-5p | 1 | Downregulated | No change |
| — | miR-215 | hsa-miR-215 | 1 | Downregulated | N.D. |
| — | miR-299-5p | hsa-miR-299-5p | 1 | Downregulated | N.D. |
| 133 | miR-30a | hsa-miR-30a-5p | 1 | Downregulated | No change |
| 153 | miR-335 | hsa-miR-335-5p | 1 | Downregulated | No change |
| 167 | miR-365 | hsa-miR-365a-3p | 1 | Downregulated | Upregulated |
| 175 | miR-378 | hsa-miR-378a-3p | 1 | Downregulated | Upregulated |
| — | miR-379 | hsa-miR-379-5p | 1 | Downregulated | N.D. |
| 180 | miR-411 | hsa-miR-411-5p | 1 | Downregulated | Downregulated |
| 50 | miR-145 | hsa-miR-145-5p | 3 | contradiction | Upregulated |
| 38 | miR-133a | hsa-miR-133a | 2 | contradiction | Upregulated |
| 233 | miR-92a | hsa-miR-92a-3p | 2 | contradiction | Upregulated |
| — | let-7c* | removed | 1 | Downregulated | |
| — | miR-499 | removed | 1 | Upregulated | |
| — | miR-801 | removed | 2 | Upregulated | |
| — | miR-196a2 | unclear | 1 | Upregulated | |

The miRNAs not listed in Table 4 (expression levels ≥500 copies/ml) were considered to be below detection limit of the present study (N.D.). Some of the miRNAs were removed in the latter version of miRBase (indicated removed) and one of the miRNAs (miR-196a2) was not found in the miRBase (mature miRNA list). For certain miRNAs, there were contradictions for the direction of changes in breast cancer subjects from various literature reports (contradiction indicated in the able accordingly).

Similarly, when comparing the control and various subtypes of breast cancer, 132 miRNAs were found to be differently expressed in the luminal A (LA) subtype, 141 were found to be differently expressed in HER subtype and 143 were found differently expressed in the triple negative (TN) subtype (Table 5). Again, more miRNAs were found to be upregulated that previously shown.

Figure 5:
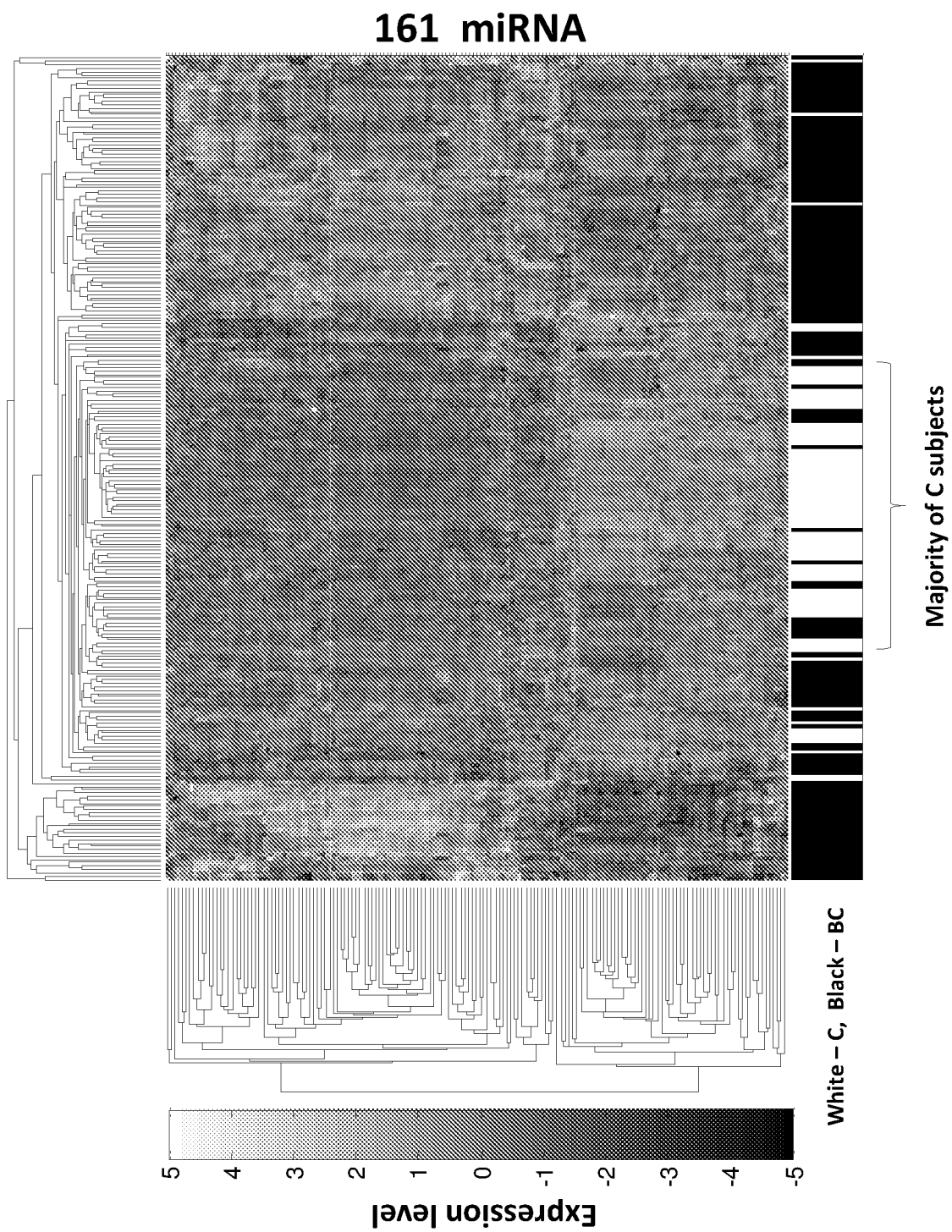
FIG. 5 shows an expression level heat-map of regulated miRNAs in breast cancer subjects. The heat-map representation of all regulated miRNAs in all breast cancer subjects (Table 5, C vs. BC, p-value <0.01); the expression levels (copy/nil) of miRNAs were presented in log2 scale and standardized to zero mean. The gray-scale represented the concentrations of miRNA. Hierarchical clustering was carried out for both dimensions (the miRNAs and the samples) based on the Euclidean distance. For the horizon dimension: black—breast cancer (BC) subjects, white—control (cancer free (normal) subjects).
Figure 6:
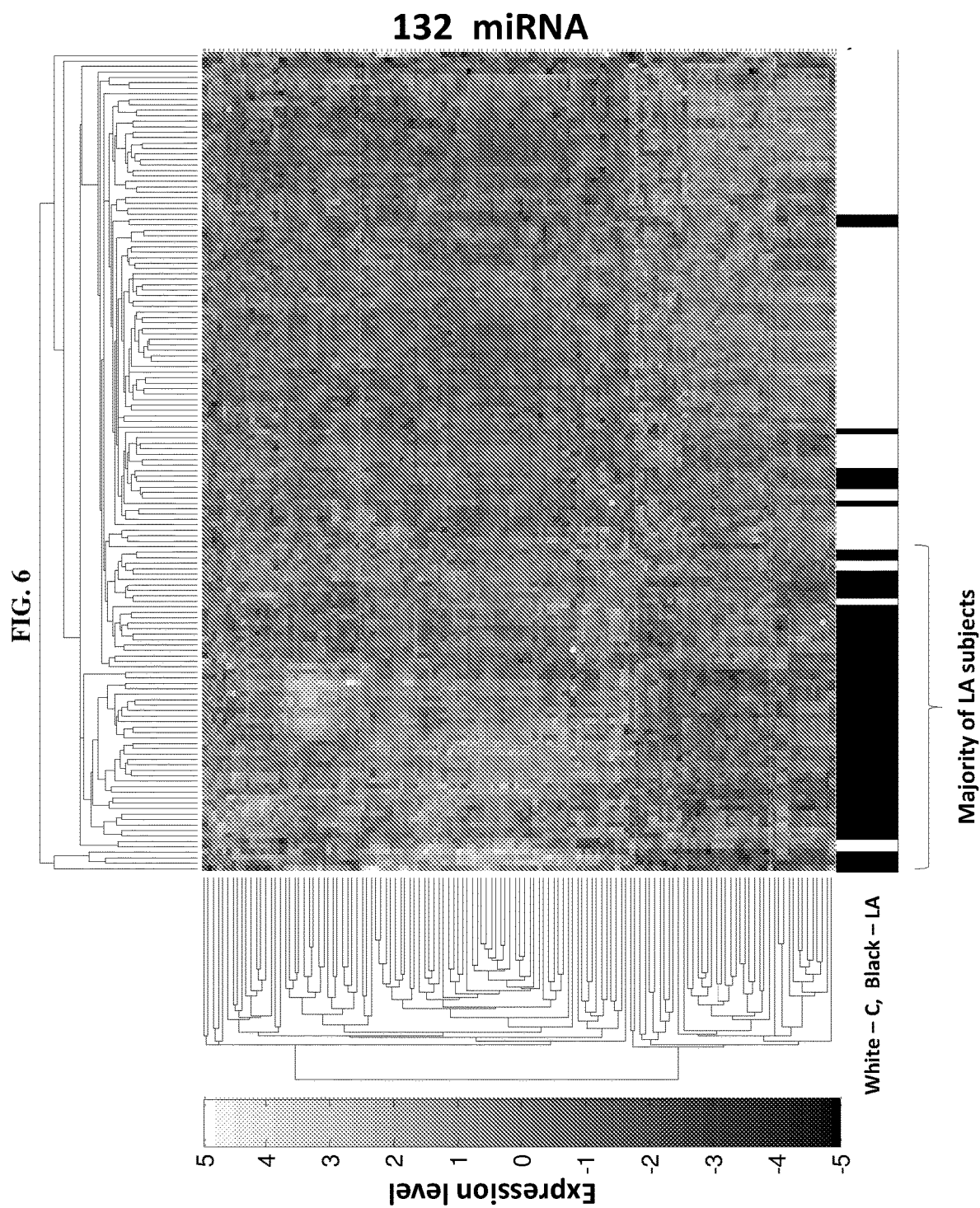
FIG. 6 shows an expression level heat-map of regulated miRNAs in luminal A subtype breast cancer subjects. The heat-map representation of all regulated miRNAs in luminal A subtype breast cancer subjects (Table 5, C vs. LA, p-value <0.01); the expression levels (copy/ml) of miRNAs were presented in log2 scale and standardized to zero mean. The gray-scale represented the concentrations of miRNA. Hierarchical clustering was carried out for both dimensions (the miRNAs and the samples) based on the Euclidean distance. For the horizon dimension: black—luminal A subtype breast cancer subjects, white—control (cancer free (noonal) subjects).
Figure 7:
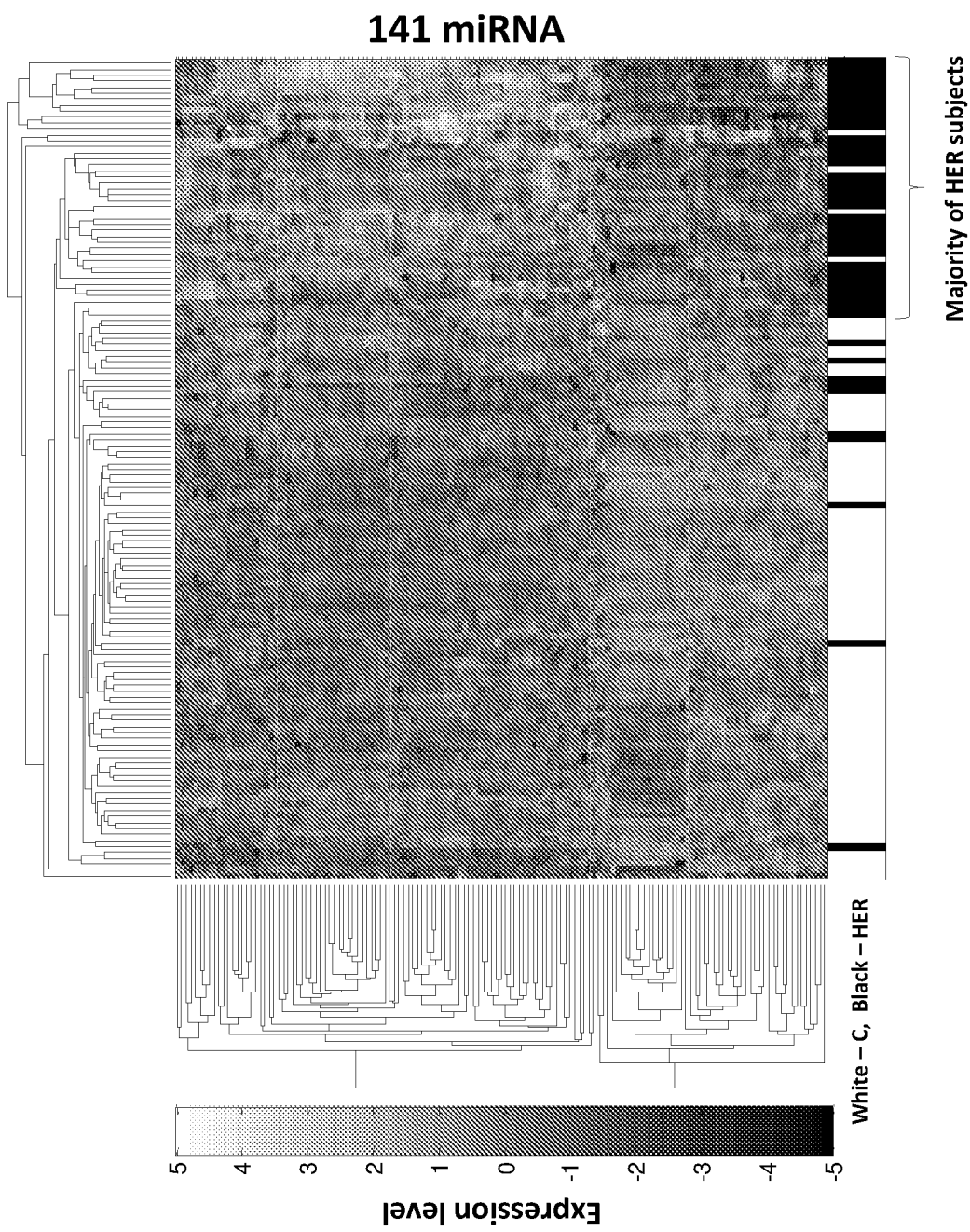
FIG. 7 shows an expression level heat-map of regulated miRNAs in Her2 subtype breast cancer subjects. The heat-map representation of all regulated miRNAs in Her2 subtype breast cancer subjects (Table 5, C vs. HER, p-value<0.01); the expression levels (copy/ml) of miRNAs were presented in log2 scale and standardized to zero mean. The gray-scale represented the concentrations of miRNA. Hierarchical clustering was carried out for both dimensions (the miRNAs and the samples) based on the Euclidean distance. For the horizon dimension: black—Her2 subtype breast cancer subjects, white—control (cancer free (normal) subjects).
Figure 8:
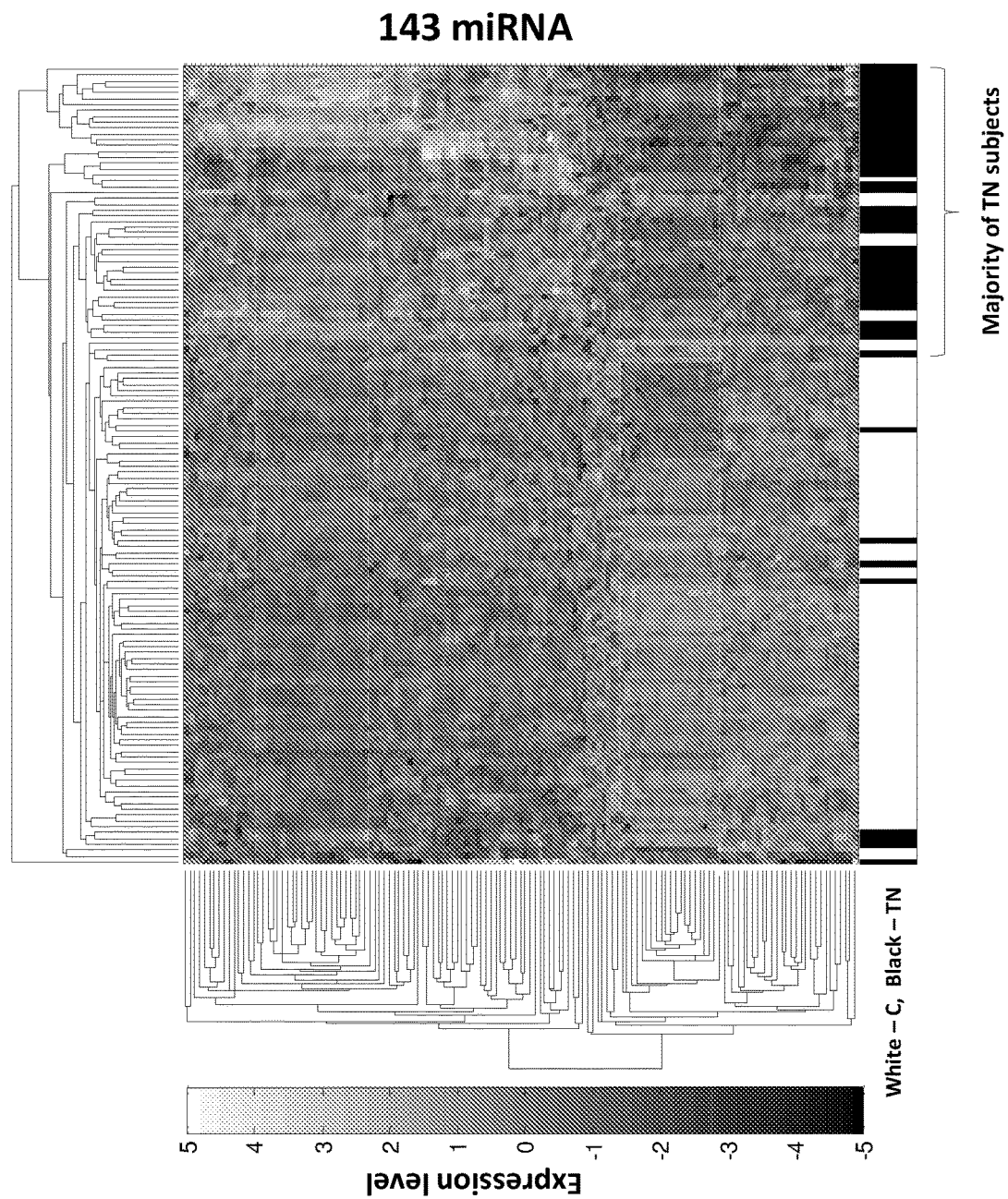
FIG. 8 shows an expression level heat-map of regulated miRNAs in triple negative subtype breast cancer subjects. The heat-map representation of all regulated miRNAs in triple negative subtype breast cancer subjects (Table 5, C vs. TN, p-value<0.01); the expression levels (copy/ml) of miRNAs were presented in log2 scale and standardized to zero mean. The gray-scale represented the concentrations of miRNA. Hierarchical clustering was carried out for both dimensions (the miRNAs and the samples) based on the Euclidean distance. For the horizon dimension: black—triple negative subtype breast cancer subjects, white—control (cancer free (normal) subjects).

Using this set of 161 biomarkers, a more distinct clustering between breast cancer and cancer-free subjects were observed in the heat-map of the miRNA profile (FIG. 5). Looking at the horizontal dimension, majority of breast cancer subjects (black) were clustered into a focused area leaving majority of the cancer-free subjects to the rest of the space in the map. And even better separations were observed when using significantly altered miRNAs to construct the heat-maps for the comparisons between control and luminal A subtype (FIG. 6), control and HER subtype (FIG. 7), control and triple negative subtype (FIG. 8). Almost all the cancer subjects were clustered together, which strongly suggests that the cancer subjects had distinct miRNA profiles.

Figure 9:
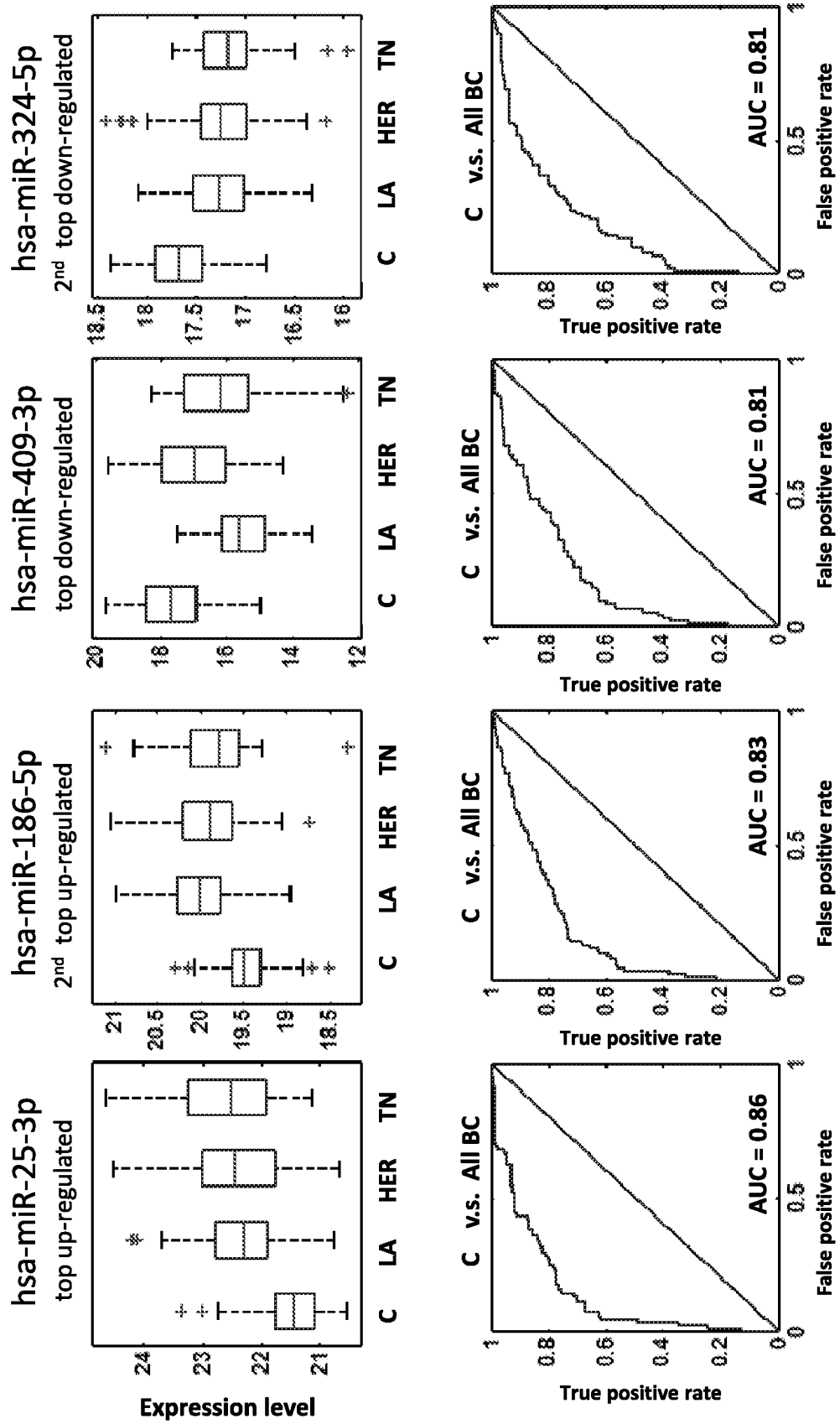
FIG. 9 is a combination of boxplots and receiver operating characteristic curve graphs showing the top upregulated and downregulated miRNAs between normal and breast cancers. The boxplot and receiver operating characteristic curves of topped and 2nd topped (based on AUC) up-regulated and down-regulated miRNAs in all breast cancer subjects compared to the normal subjects. AUC: area under the receiver operating characteristic curve. The boxplot presented the $25^{th}$, $50^{th}$ and $75^{th}$ percentiles in the distribution of log2 scale expression levels (copy/ml). C—Control, LA—luminal A subtype, HER—Her2 subtype, TN—triple negative subtype

The AUC values for the topped ranked upregulated (hsa-miR-25-3p) and second topped ranked (hsa-miR-186-5p) upregulated miRNA in breast cancer for all subtypes were 0.86 and 0.83, respectively (FIG. 9). The AUC values for the topped ranked downregulated (hsa-miR-409-3p) and second topped ranked (hsa-miR-324-5p) downregulated miRNA in breast cancer for all subtypes had a value of only 0.81 (FIG. 9). Thus, without being bound by theory, it is expected that combining multiple miRNAs in a multivariate manner will provide a biomarker panel with enhanced performance for breast cancer diagnosis.

Figure 10:
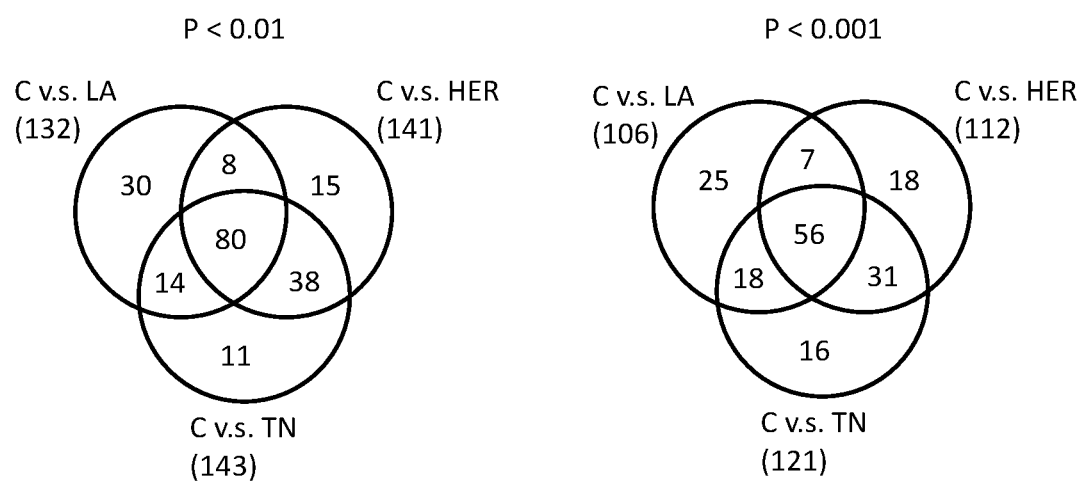
FIG. 10 shows Venn diagrams depicting the overlap between biomarkers for breast cancer. These diagrams illustrate the overlaps of miRNAs that differentially expressed in various subtypes of breast cancers compared to control (based on Table 6). C—Control, LA—luminal A subtype, HER—Her2 subtype, TN—triple negative subtype.

Examining the overlap between regulated miRNAs in luminal A, HER and triple negative subtypes, 80 miRNAs were found to be statistically significant for all subtypes with a p-value of<0.01 after false discovery rate correction; 56 miRNAs had a p-value of<0.001 after false discovery rate correction. (FIG. 10). Each, or the combination of a few, of these 80 miRNAs, that is the first 80 miRNAs as shown in Table 6, can serve as a biomarker or as a panel of biomarkers in, for example, multivariate index assays, for the diagnosis of early stage breast cancer.

Figure 11:
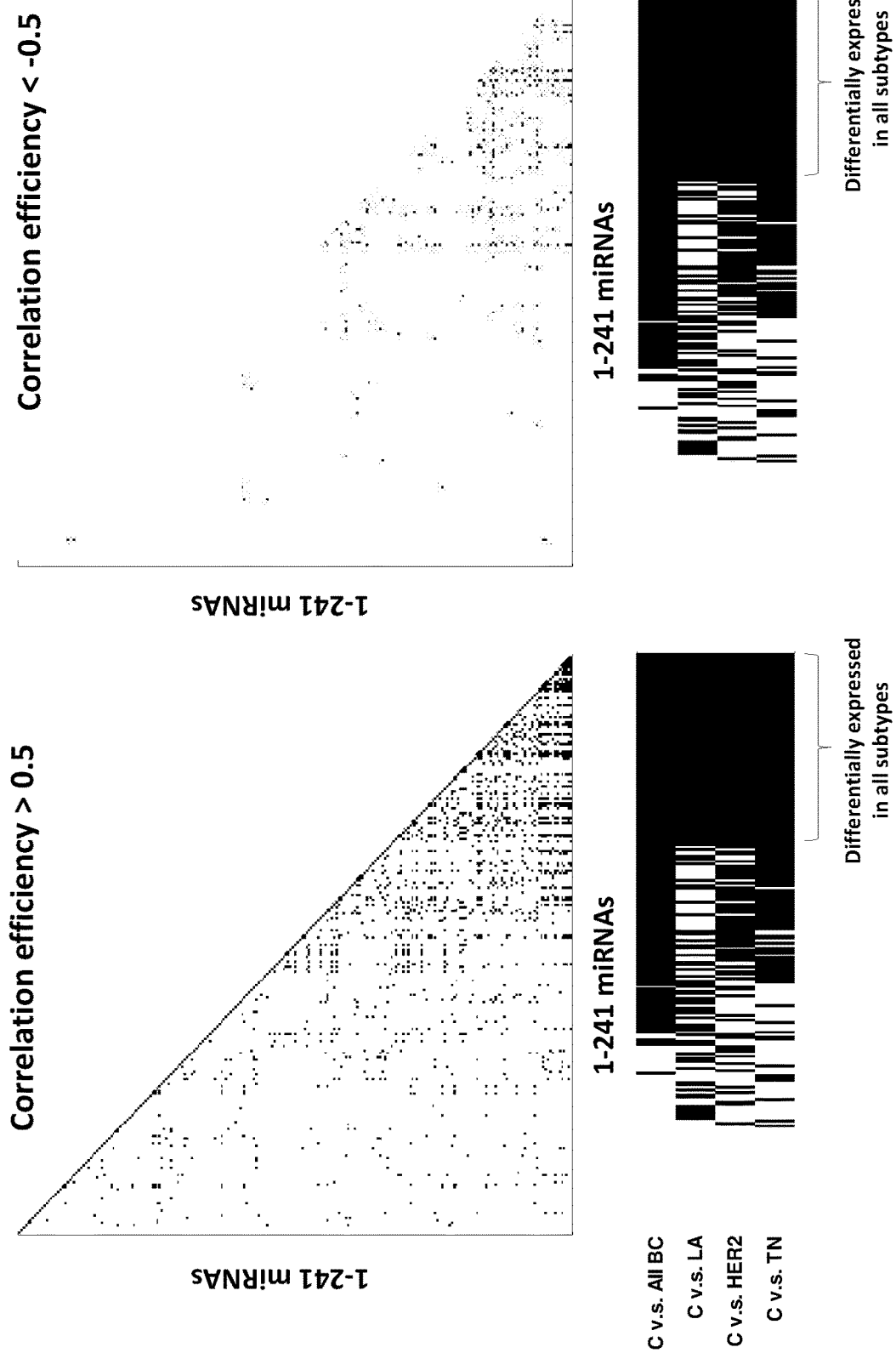
FIG. 11 shows scatterplots and heat-maps showing the results of a correlation analysis between all reliable detected miRNAs. Based on the log2 scale expression levels (copy/mL), the Pearson's linear correlation efficiencies were calculated between all 241 reliable detected miRNA targets (Table 4). Each dot represents a pair of miRNAs where the correlation efficiency is higher than 0.5 (left figure, positively correlated) or low than −0.5 (right figure, negatively correlated). The differentially expressed miRNAs in breast cancer were indicated as black in the horizon dimension. C—Control, LA—luminal A subtype, HER—Her2 subtype, TN—triple negative subtype.

The expression of miRNAs was found to cluster into subgroups as illustrated in the heat-maps shown in FIGS. 3 to 8). Each cluster has about 10 to 20 miRNAs (FIG. 3-8 dashed lines). Analyses of all detectable miRNAs revealed a large number of these miRNAs as positively correlated based on a Pearson correlation efficiency of >0.5 (FIG. 11), especially between those miRNAs altered in breast cancer subjects and those in cancer-free subjects. These miRNAs are indicated in black in the x-axis, towards right hand side of the x-axis, in FIG. 11. This data thus validates the situation that the presence of a solid breast tumour is a major cause of change of miRNA levels in serum. Observations demonstrated that certain groups of miRNAs are similarly regulated among all subjects. As a result, a panel of miRNAs could be assembled by substituting one or more distinct miRNAs with another, so as to enhance the diagnostic performance. Furthermore, all the significantly altered miRNA are deemed critical for the development of a multivariate index diagnostic assay for breast cancer.

III—Search for Multivariate Biomarker Panels

As discussed above, there are different miRNA profiles for each of the various subtypes of cancer. An important criterion to assembling such a multivariate panel is to include at least one miRNA from the specific list for each subtype of cancer, in order to ensure that all cancer subgroups were covered. However, the miRNAs defining the three subtype of cancer were not completely distinct, as same miRNAs were similarly found between them (FIG. 10). At the same time, a large number of cancer-related or cancer non-related miRNAs were found to be positively correlated (FIG. 11), making the choice of the most statistically significant miRNA combinations for early breast cancer diagnosis a challenge.

In view of the complexity of the task, it was decided to identify panels of miRNA with the highest AUC values using a sequence forward floating search algorithm. A state-of-the art linear support vector machine, a well-utilized and recognized modelling tool for the construction of panels of variables, was also used to aid in the selection of the combinations of miRNAs. The model yields a score based on a linear formula accounting for the expression level of each member and their weightages. These linear models are easily accepted and applied in the clinical practice.

Calculation of Cancer Risk Score

MiRNAs can be combined to form a biomarker panel to calculate the cancer risk score according to Formula 1 as shown below. For example, 12 miRNAs frequently selected in the multivariate biomarker panel identification process with prevalence>20% (for example, Table 8) can be combined to form a biomarker panel to calculate the cancer risk score. The formula here demonstrates the use of a linear model for breast cancer risk prediction, where the cancer risk score (unique for each subject) indicates the likelihood of a subject having gastric cancer. This is calculated by the summing the weighted measurements for, for example, 12 miRNAs and a constant of 50.

$$\text{cancer risk score} = 50 + \sum_{i=1}^{12} K_i \times \log_2 \text{copy\_miRNA}_i \quad \text{Formula 1}$$

$\log_2\text{copy\_miRNA}_i$-log transformed copy numbers (copy/ml of serum) of the 12 individual miRNAs'). $K_i$—the coefficients used to weight multiple miRNA targets. The values of $K_i$ were optimized with support vector machine method and scaled to range from 0 to 100. Subjects with cancer risk score lower than 0 will be considered as 0 and subjects with cancer risk score higher than 100 will be considered as 100.

As an illustrative example, the control and cancer subjects in these studies have different cancer risk score values calculated based on the formula shown above. Fitted probability distributions of the cancer risk scores for the control and cancer subjects show a clear separation between the two groups can be found. In this exemplary study, the control subjects were non-cancer subjects selected from the high risk population, which has a probability of 0.0067 to have breast cancer. Based on this prior probability and the fitted probability distributions previously determined, the probability (risk) of an unknown subject having cancer can be calculated based on their cancer risk score values. With higher score, the subject has higher risk of having breast cancer. Furthermore, the cancer risk score can, for example, tell the fold change of the probability (risk) of an unknown subject having breast cancer compared to, for example, the cancer incidence rate in high risk population. For example, an unknown high risk subject having cancer risk score of 70 will have 14.6% probability to have breast cancer, which is about 22 times higher than the average risk of the high risk population.

A critical requirement for the success of such process is the availability of high quality data. The quantitative data of all the detected miRNAs in a large number of well-defined clinical samples not only improves the accuracy, as well as precision, of the result, but also ensures the consistency of the identified biomarker panels for further clinical application using quantitative polymerase chain reaction (qPCR).

With the large number of clinical samples (248 in total), the potential issue of over-fitting of data during modeling was minimized, as there were only 241 candidate miRNAs to be selected from. In addition, to ensure the veracity of the result, multiple four-fold cross-validations were carried out to test the performance of the identified biomarker panel based on the discovery set (¾ of the samples at each fold) in an independent set of validation samples (the remaining ¼ of the samples at each fold). During the cross-validation process, the samples were matched for subtype and stage.

Figure 12:
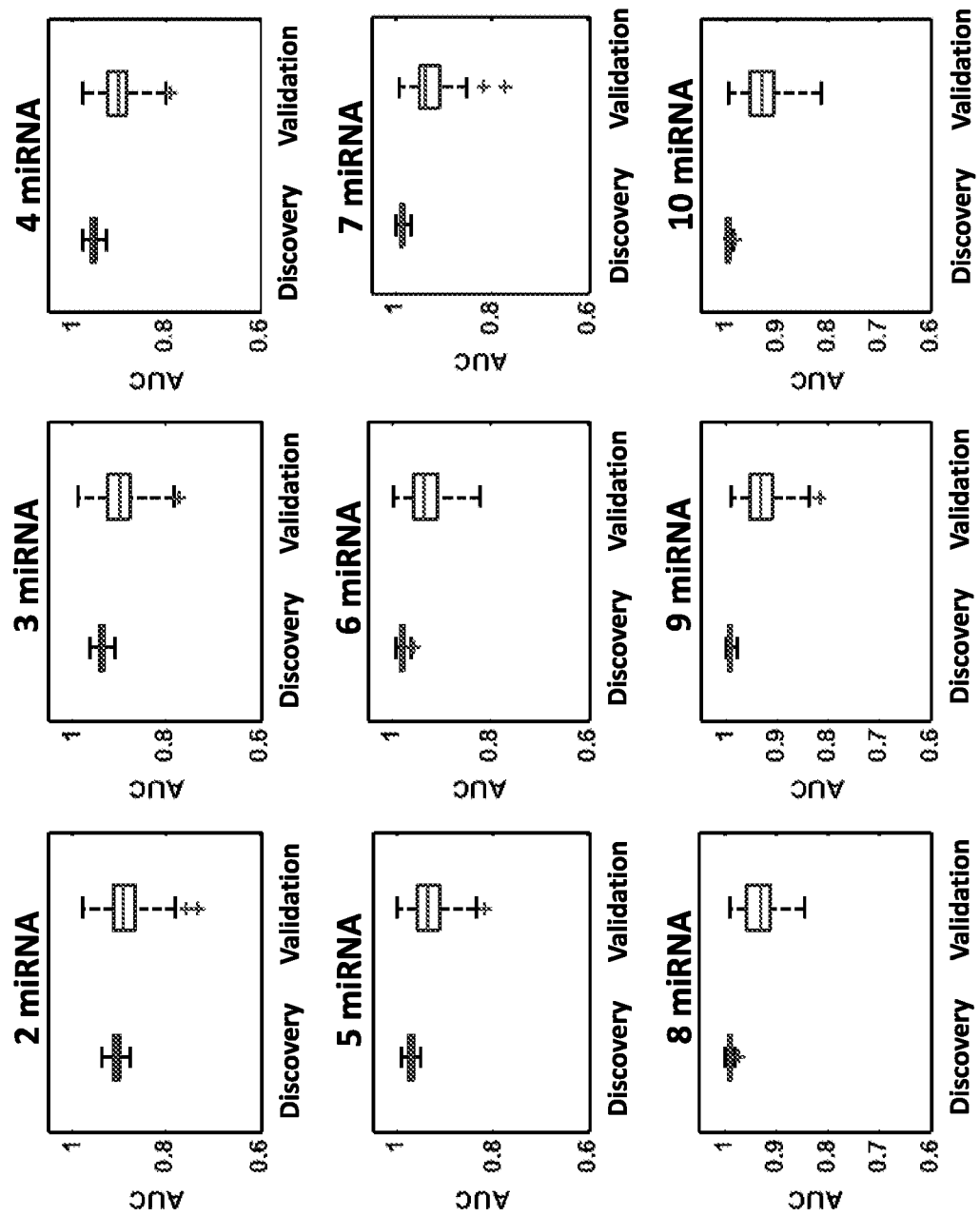
FIG. 12 shows boxplots outlining the identification/discovery of multivariate biomarker panels. The boxplots of the diagnostic power (AUC) of multivariate biomarker panels (number of miRNAs=2–10) in the discovery and validation phases during the four fold cross validation in silico. The biomarker panels with 2 to 10 miRNAs were identified with the sequence forward floating search using linear support vector machine as the model based on the discovery set of samples and validated in another independent set of samples. Multiple times of four fold cross validation were carried out. The boxplot presented the $25^{th}$, $50^{th}$, and $75^{th}$ percentiles in the AUC for the classification of normal and breast cancer subjects.

The boxplots representative of the results, that is the AUC of the biomarker panel in both discovery phase and validation phase, are shown in FIG. 12. The AUC values are quite close in the various discovery sets (box size<0.01) and they approached unity (100% AUC) with increasing number of miRNAs in the panel. As predicted, there was a decrease in AUC values with the validation set for each search (0.02-0.05). Although the size of the box was larger with data in the validation phase, indicative of a spread of values, the difference was<0.5 AUC values.

Figure 13:
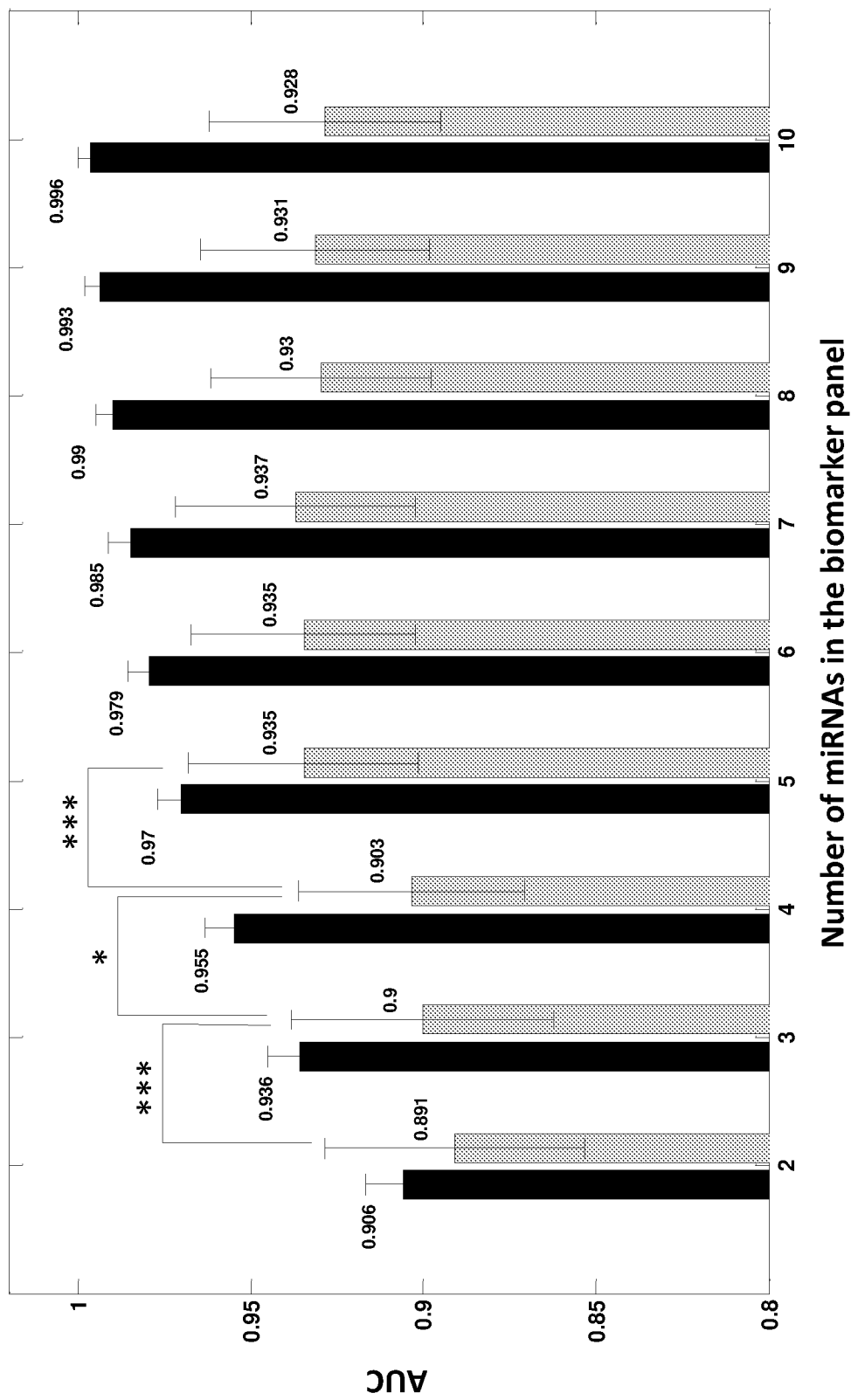
FIG. 13 shows line graphs depicting the calculated area under the curve (AUC) values of multivariate biomarker panels. The mean AUC of various multivariate biomarker panels in the discovery set (black) and validation set (gray) during the cross validation processes. The error bar represented the standard deviation of the AUC. In order to test the significance of the AUC improvement in the validation set when more miRNAs were included in the panel, the right-tailed t-test was carried to compare all the adjacent gray bars. *: p-value<0.05; : p-value<0.01; *: p-value <0.001.

A more quantitative representation of the results was shown in FIG. 13. Although there was always a gradual increase of the AUC in the discovery phase when increasing the number of miRNA in the biomarker panel, there were no further improvements in the AUC values in the validation phase, when the number of the miRNAs was greater than 5. Thus, a biomarker panel with 5 or more miRNAs resulting in an AUC value of around 0.93 was deemed useful for early stage breast cancer diagnosis.

IV—Composition of Multivariate miRNA Biomarker Panels

To examine the composition of multivariate biomarker panels, the occurrences of miRNAs in all the panels containing 5 to 10 miRNAs were counted, whereby the panels with the top 10% and bottom 10% of AUC values were excluded. This was carried out to avoid including falsely discovered biomarkers due to fitting of inaccurate data from subpopulations generated by the randomization process in cross-validation analysis. By excluding these miRNAs chosen in less than 2% of the panels, a total of 44 miRNAs were selected in the discovery process (Table 8), wherein the expression of 37 of these miRNAs were also found to be significantly altered in cancers (Table 6). The inclusion of 7 other miRNAs, although not altered in cancers, were found to significantly improve the AUC values in more than half of the panels, when at least one of these miRNA from the list (51.0%) was included. Without a direct and quantitative measurement of all miRNA targets, these miRNAs would never have been selected in high-through put screening studies (for example, microarray, sequencing) and would have been excluded from further quantitative polymerase chain reaction (qPCR) validation.

NAs in the list with occurrence higher than 10%, only 6 of the miRNAs were found to be commonly regulated in all cancer subtypes, namely hsa-miR-1291, hsa-miR-324-5p, hsa-miR-378a-5p, hsa-miR-125b-5p, hsa-miR-375, hsa-miR-409-3p, while the rest were only significant for one or

TABLE 8

MiRNAs identified in multivariate biomarker panel identification process

| SEQ ID NO: | Name | Prevalence in biomarker panels | Significant for LA | Significant for HER | Significant for TN | Significant for all BC |
|---|---|---|---|---|---|---|
| | | Significant miRNAs | | | | |
| 178 | hsa-miR-409-3p | 96.6% | Yes | Yes | Yes | Yes |
| 177 | hsa-miR-382-5p | 68.0% | No | No | Yes | Yes |
| 173 | hsa-miR-375 | 65.4% | Yes | Yes | Yes | Yes |
| 112 | hsa-miR-23a-3p | 44.3% | No | Yes | Yes | Yes |
| 24 | hsa-miR-124-5p | 37.2% | Yes | No | Yes | Yes |
| 176 | hsa-miR-378a-5p | 35.7% | Yes | Yes | Yes | Yes |
| 26 | hsa-miR-125b-5p | 35.0% | Yes | Yes | Yes | Yes |
| 44 | hsa-miR-140-5p | 23.0% | No | No | Yes | No |
| 199 | hsa-miR-485-5p | 13.6% | No | No | Yes | Yes |
| 115 | hsa-miR-23c | 12.8% | No | Yes | Yes | Yes |
| 33 | hsa-miR-1291 | 12.3% | Yes | Yes | Yes | Yes |
| 146 | hsa-miR-324-5p | 12.0% | Yes | Yes | Yes | Yes |
| 206 | hsa-miR-500a-3p | 10.1% | Yes | No | Yes | Yes |
| 171 | hsa-miR-374a-5p | 9.1% | Yes | Yes | Yes | Yes |
| 198 | hsa-miR-485-3p | 9.0% | Yes | No | Yes | Yes |
| 47 | hsa-miR-143-3p | 7.9% | Yes | Yes | Yes | Yes |
| 213 | hsa-miR-551b-3p | 7.6% | No | Yes | Yes | Yes |
| 77 | hsa-miR-186-5p | 6.5% | Yes | Yes | Yes | Yes |
| 157 | hsa-miR-339-3p | 5.7% | Yes | Yes | Yes | Yes |
| 84 | hsa-miR-193b-3p | 5.2% | Yes | Yes | Yes | Yes |
| 219 | hsa-miR-616-3p | 4.7% | Yes | Yes | Yes | Yes |
| 143 | hsa-miR-320d | 4.2% | Yes | Yes | Yes | Yes |
| 66 | hsa-miR-15b-5p | 3.8% | Yes | Yes | No | No |
| 147 | hsa-miR-32-5p | 3.7% | No | Yes | No | Yes |
| 81 | hsa-miR-191-5p | 3.7% | No | No | Yes | No |
| 3 | hsa-let-7b-5p | 3.3% | Yes | No | Yes | Yes |
| 1 | hsa-let-7a-5p | 3.0% | Yes | Yes | Yes | Yes |
| 232 | hsa-miR-885-5p | 2.8% | Yes | No | No | No |
| 29 | hsa-miR-127-3p | 2.8% | Yes | Yes | Yes | Yes |
| 144 | hsa-miR-320e | 2.8% | No | Yes | No | No |
| 117 | hsa-miR-25-3p | 2.8% | Yes | Yes | Yes | Yes |
| 126 | hsa-miR-299-3p | 2.4% | No | Yes | Yes | Yes |
| 86 | hsa-miR-195-5p | 2.3% | No | Yes | Yes | Yes |
| 32 | hsa-miR-1285-3p | 2.2% | Yes | Yes | Yes | Yes |
| 154 | hsa-miR-337-3p | 2.2% | No | Yes | Yes | Yes |
| 73 | hsa-miR-181d | 2.1% | Yes | Yes | Yes | Yes |
| 43 | hsa-miR-140-3p | 2.1% | No | Yes | Yes | Yes |
| | | Insignificant miRNAs | | | | |
| 22 | hsa-miR-122-5p | 41.8% | No | No | No | No |
| 95 | hsa-miR-200b-3p | 4.2% | No | No | No | No |
| 42 | hsa-miR-139-5p | 3.9% | No | No | No | No |
| 57 | hsa-miR-150-3p | 3.0% | No | No | No | No |
| 227 | hsa-miR-652-3p | 2.5% | No | No | No | No |
| 27 | hsa-miR-126-3p | 2.1% | No | No | No | No |
| 39 | hsa-miR-135a-5p | 2.0% | No | No | No | No |

The identities of the miRNAs selected for the assembly of biomarker panels with 5, 6, 7, 8, 9, and 10 miRNA were summarized. Prevalence was defined by the counts of the miRNA in all panels divided by the total number of panels. The panels with the top 10% and bottom 10% AUC were excluded to avoid counting of falsely discovered biomarkers due to fitting of inaccurate data from subpopulations generated by the randomization process in cross-validation analysis. Only the miRNAs used in more than 2% of the panels were listed. The changes of the miRNAs in various stages of breast cancers were defined based on Table 6.

The miRNAs selected to form the multivariate panels (Table 8) showed variability in detecting various cancer subtypes (Table 6). For the top 13 frequently chosen miRtwo of the subtypes. When comparing the identities of the chosen miRNAs for multivariate panels and single miRNA as diagnostic markers, they were not necessarily the same. For example, the top downregulated (hsa-miR-409-3p) miRNA was highly represented (96.6%) while and the top upregulated (hsa-miR-25-3p) was only used in 2.8% of the panels (FIG. 9). Hence, it was not possible merely to combine the best biomarkers identified for various stages to form the optimal biomarker panel, but rather a panel of markers is formed by reviewing complementary information that gives the best result.

Figure 14:
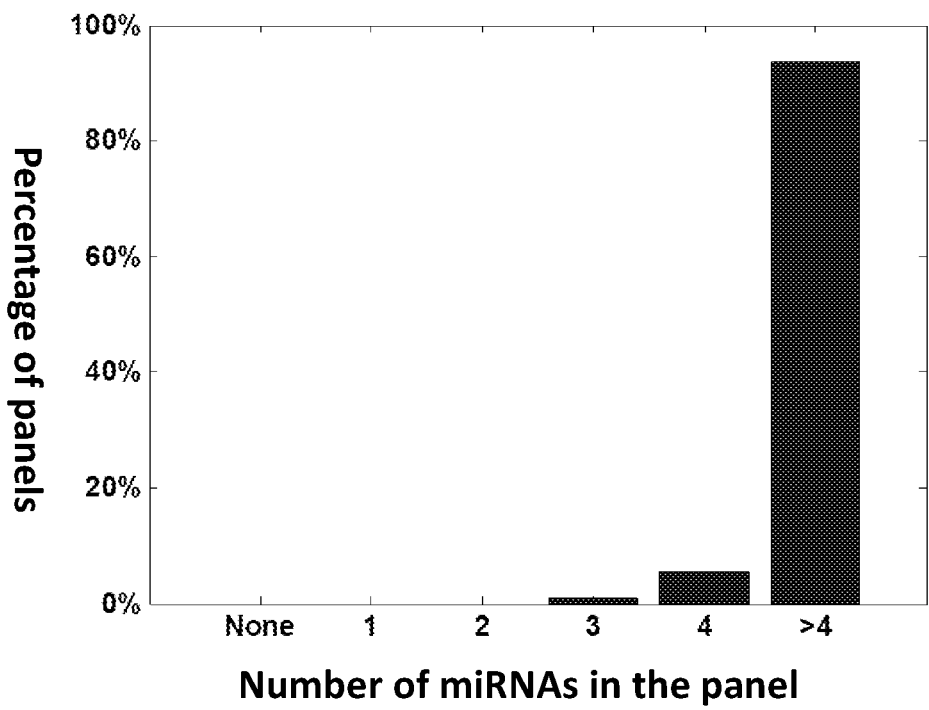
FIG. 14 shows a column graph depicting the percentage of 5-10 miRNA biomarker panels including various numbers of highly selected miRNAs. The percentage of all the 5-10 miRNA biomarker panels discovered in the searching process with various numbers of highly selected miRNAs (in total 44, Table 8). The panels with the top 10% and bottom 10% AUC were excluded.
Figure 15:
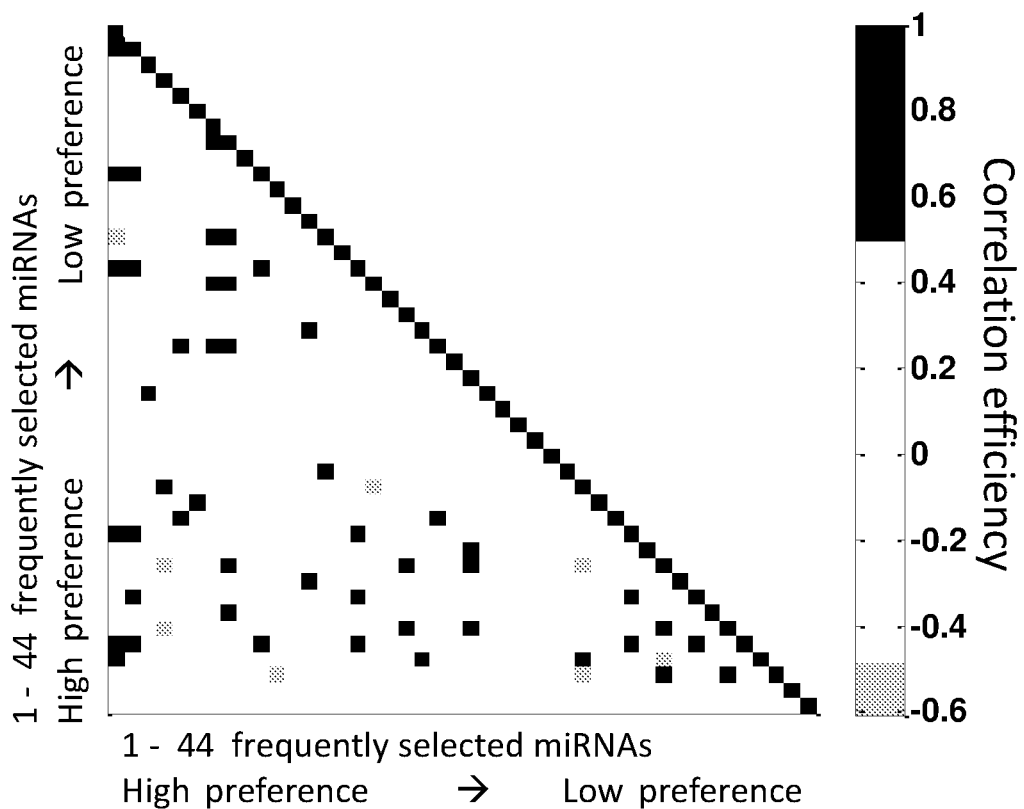
FIG. 15 shows the results of a correlation analysis between all frequently selected miRNAs in the form of a scatter plot. Based on the log2 scale expression levels (copy/mL), the Pearson's linear correlation efficiencies were calculated between 44 frequently selected miRNA targets (Table 8). Each dot represents a pair of miRNAs where the correlation efficiency is higher than 0.5 (black, positively correlated) or low than −0.5 (gray, negatively correlated). The miRNAs were ranked based on their preference (Table 8).

After excluding those miRNAs within the top 10% and bottom 10% AUC values, all the 5 to 10 miRNA biomarker panels included at least 3 miRNAs from the frequently selected list (Table 8), with 93.5% of the panels including 5 or more miRNAs from the frequently selected list (FIG. 14). Based on the correlation analysis, a number of miRNAs in the frequently selected list were correlated with each other (FIG. 15). As discussed, these miRNAs could serve as replacement or substitutes for each other in the biomarker panels and were chosen at various cycles during the cross-validation process. In conclusion, a biomarker panel with at least 5 miRNAs from the frequently selected list (Table 8) is to be used for the diagnosis of early stage breast cancer.

Figure 16:
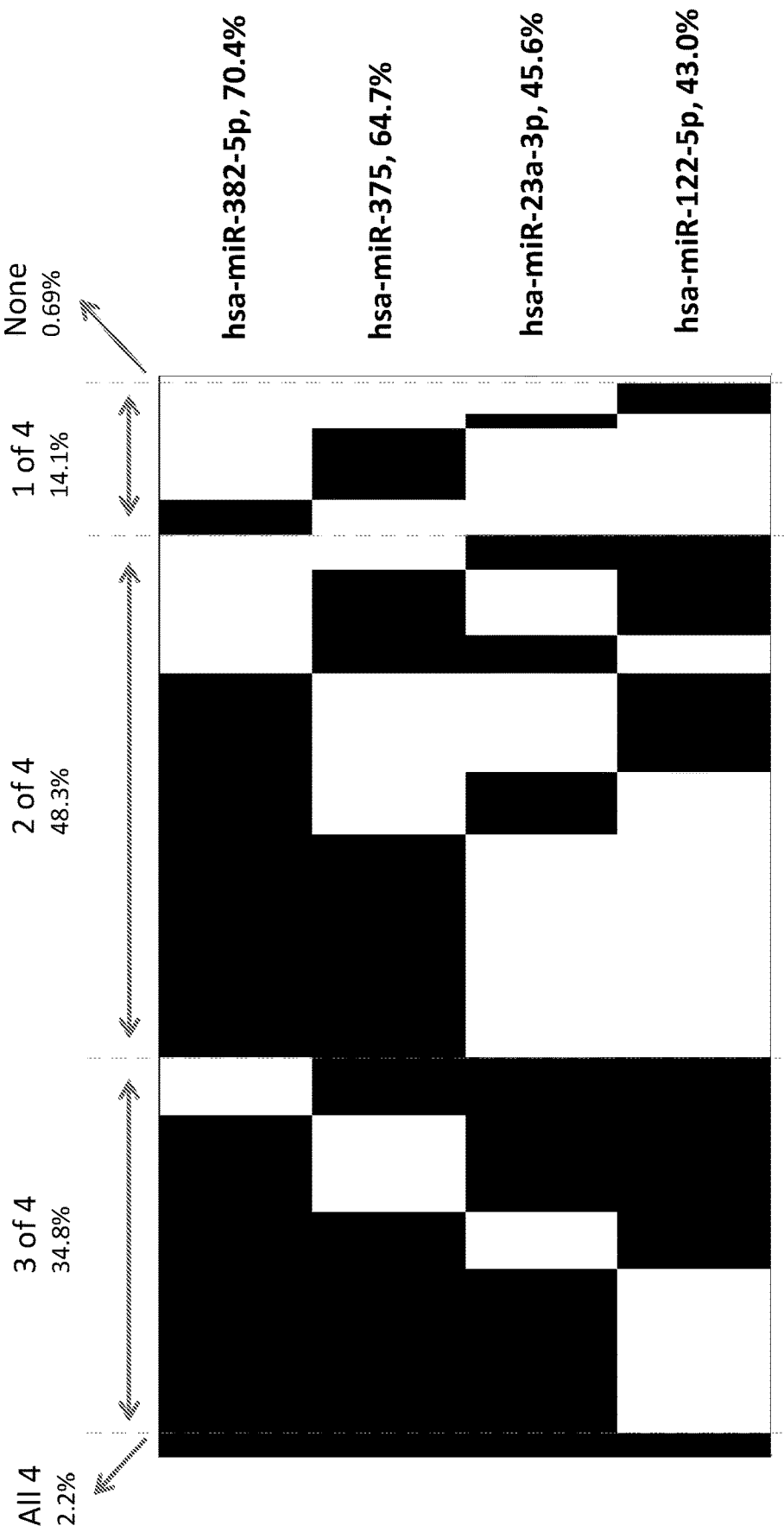
FIG. 16 shows distribution of hsa-miR-382-5p, hsa-miR-375, hsa-miR-23a-3p, hsa-miR-122-5p in all the 5-10 miRNA biomarker panels including hsa-miR-409-3p in the form of a heat-map. Distribution of hsa-miR-382-5p, hsa-miR-375, hsa-miR-23a-3p and hsa-miR-122-5p in all the selected 5-10 miRNA biomarker panels with hsa-miR-409-3p; the black blocks represented the presence of the miRNA in the biomarker panel. The percentages represented the proportions in all the panels.

Further examination of the top 5 most frequently selected miRNAs with a prevalence higher than 40% (Table 8) showed that the top one miRNA, hsa-miR-409-3p, was found in 96.6% of the panels, thereby underlining the importance of this particular miRNA. The distribution of the next four miRNAs (hsa-miR-382-5p, hsa-miR-375, hsa-miR-23a-3p and hsa-miR-122-5p) in all the panels which included hsa-miR-409-3p is illustrated in FIG. 16, whereby very small portion of panels tested were found to have none (0.69%) or all four (2.2%) of these miRNAs. For any pair of the miRNAs, there was no clear sign of coexistence or mutual exclusion, thus suggesting that these four miRNAs were equally important in improving the performance of hsa-miR-409-3p in a biomarker panel. As a result, the most frequent biomarker panels included hsa-miR-409-3p and at least one miRNA from hsa-miR-382-5p, hsa-miR-375, hsa-miR-23a-3p and hsa-miR-122-5p.

Univariate analysis (Student's t-test):

115 novel miRNAs were found to be applicable in the detection of Luminal A subtype breast cancer, which had not been previously reported (Table 9), whereby 73 miRNAs were upregulated and 42 miRNAs were downregulated in cancer patients compared to normal, cancer-free subjects. 125 novel miRNAs found to be applicable for in detection of HER2 subtype breast cancer, which had not been previously reported (Table 10), whereby 78 miRNAs were upregulated and 47 miRNAs were downregulated in cancer patients compared to normal, cancer-free subjects. 125 novel miRNAs found to be applicable in the detection of triple negative subtype breast cancer, which had not been previously reported (Table 11), whereby 70 miRNAs were upregulated and 55 miRNAs were downregulated in cancer patients compared to normal, cancer-free subjects. 141 novel miRNAs found to be applicable in the detection of breast cancer (regardless of subtypes), which had not been previously reported (Table 12), whereby 83 miRNAs were upregulated and 58 miRNAs were downregulated in cancer patients compared to normal, cancer-free subjects. 67 novel miRNAs found to be applicable in the detection of all three subtypes of breast cancer (the overlap of Table 9, 10 and 11), which had not been previously reported (Table 13). Any one or other combinations of the microRNAs from the list can be used for the detection of breast cancer.

TABLE 9

Novel miRNAs differentially expressed between cancer-free (normal) and Luminal A subtype breast cancer.

| SEQ ID NO: | Name | Regulation | FC | SEQ ID NO: | Name | Regulation | FC |
|---|---|---|---|---|---|---|---|
| 179 | hsa-miR-411-3p | Down | 0.7 | 164 | hsa-miR-362-3p | Up | 1.5 |
| 201 | hsa-miR-487b | Down | 0.5 | 84 | hsa-miR-193b-3p | Up | 1.6 |
| 157 | hsa-miR-339-3p | Down | 0.7 | 98 | hsa-miR-206 | Up | 2.9 |
| 169 | hsa-miR-370 | Down | 0.6 | 237 | hsa-miR-96-5p | Up | 1.5 |
| 73 | hsa-miR-181d | Down | 0.6 | 47 | hsa-miR-143-3p | Up | 1.9 |
| 62 | hsa-miR-154-5p | Down | 0.6 | 65 | hsa-miR-15b-3p | Up | 1.3 |
| 110 | hsa-miR-224-5p | Down | 0.7 | 212 | hsa-miR-532-5p | Up | 1.3 |
| 173 | hsa-miR-375 | Down | 0.5 | 166 | hsa-miR-363-3p | Up | 1.8 |
| 203 | hsa-miR-493-5p | Down | 0.7 | 20 | hsa-miR-10a-5p | Up | 1.2 |
| 29 | hsa-miR-127-3p | Down | 0.7 | 209 | hsa-miR-502-3p | Up | 1.9 |
| 178 | hsa-miR-409-3p | Down | 0.2 | 130 | hsa-miR-29c-3p | Up | 1.4 |
| 155 | hsa-miR-337-5p | Down | 0.6 | 175 | hsa-miR-378a-3p | Up | 1.5 |
| 146 | hsa-miR-324-5p | Down | 0.7 | 186 | hsa-miR-4306 | Up | 1.5 |
| 148 | hsa-miR-326 | Down | 0.6 | 12 | hsa-miR-1 | Up | 2.4 |
| 150 | hsa-miR-330-3p | Down | 0.8 | 129 | hsa-miR-29b-3p | Up | 1.3 |
| 158 | hsa-miR-339-5p | Down | 0.8 | 100 | hsa-miR-20b-5p | Up | 1.8 |
| 59 | hsa-miR-151a-3p | Down | 0.8 | 68 | hsa-miR-17-3p | Up | 1.6 |
| 216 | hsa-miR-584-5p | Down | 0.8 | 224 | hsa-miR-629-5p | Up | 1.4 |
| 171 | hsa-miR-374a-5p | Down | 0.7 | 228 | hsa-miR-660-5p | Up | 1.6 |
| 60 | hsa-miR-151a-5p | Down | 0.7 | 77 | hsa-miR-186-5p | Up | 1.5 |
| 123 | hsa-miR-27b-3p | Down | 0.8 | 13 | hsa-miR-101-3p | Up | 2.7 |
| 92 | hsa-miR-199b-3p | Down | 0.8 | 76 | hsa-miR-185-5p | Up | 1.4 |
| 1 | hsa-let-7a-5p | Down | 0.8 | 93 | hsa-miR-19a-3p | Up | 1.3 |
| 24 | hsa-miR-124-5p | Down | 0.6 | 140 | hsa-miR-320a | Up | 1.4 |
| 229 | hsa-miR-668 | Down | 0.6 | 64 | hsa-miR-15a-5p | Up | 1.4 |
| 198 | hsa-miR-485-3p | Down | 0.6 | 94 | hsa-miR-19b-3p | Up | 1.4 |
| 40 | hsa-miR-136-3p | Down | 0.6 | 143 | hsa-miR-320d | Up | 1.2 |
| 136 | hsa-miR-30d-3p | Down | 0.6 | 99 | hsa-miR-20a-5p | Up | 1.3 |
| 105 | hsa-miR-221-3p | Down | 0.8 | 200 | hsa-miR-486-5p | Up | 1.8 |
| 23 | hsa-miR-1226-3p | Down | 0.6 | 220 | hsa-miR-616-5p | Up | 1.4 |
| 226 | hsa-miR-651 | Down | 0.5 | 206 | hsa-miR-500a-3p | Up | 2.2 |
| 160 | hsa-miR-342-5p | Down | 0.5 | 225 | hsa-miR-650 | Up | 1.6 |
| 96 | hsa-miR-200c-3p | Down | 0.7 | 34 | hsa-miR-1299 | Up | 1.6 |
| 124 | hsa-miR-28-3p | Down | 0.8 | 16 | hsa-miR-106b-3p | Up | 1.2 |
| 183 | hsa-miR-425-3p | Down | 0.9 | 211 | hsa-miR-532-3p | Up | 1.2 |
| 90 | hsa-miR-199a-3p | Down | 0.8 | 74 | hsa-miR-1825 | Up | 1.7 |
| 152 | hsa-miR-335-3p | Down | 0.7 | 49 | hsa-miR-144-5p | Up | 1.4 |
| 37 | hsa-miR-130b-5p | Down | 0.9 | 89 | hsa-miR-197-3p | Up | 1.4 |
| 104 | hsa-miR-219-5p | Down | 0.8 | 109 | hsa-miR-22-3p | Up | 1.2 |
| 232 | hsa-miR-885-5p | Down | 0.6 | 3 | hsa-let-7b-5p | Up | 1.5 |

TABLE 9-continued

Novel miRNAs differentially expressed between cancer-free (normal) and Luminal A subtype breast cancer.

| SEQ ID NO: | Name | Regulation | FC | SEQ ID NO: | Name | Regulation | FC |
|---|---|---|---|---|---|---|---|
| 137 | hsa-miR-30d-5p | Down | 0.9 | 69 | hsa-miR-17-5p | Up | 1.4 |
| 35 | hsa-miR-130a-3p | Down | 0.8 | 214 | hsa-miR-573 | Up | 2.2 |
| 221 | hsa-miR-618 | Up | 1.8 | 165 | hsa-miR-362-5p | Up | 1.3 |
| 219 | hsa-miR-616-3p | Up | 1.3 | 182 | hsa-miR-424-5p | Up | 1.6 |
| 222 | hsa-miR-627 | Up | 1.6 | 172 | hsa-miR-374b-5p | Up | 2 |
| 194 | hsa-miR-4732-3p | Up | 1.5 | 163 | hsa-miR-361-5p | Up | 1.3 |
| 208 | hsa-miR-501-5p | Up | 1.7 | 53 | hsa-miR-148a-3p | Up | 1.4 |
| 176 | hsa-miR-378a-5p | Up | 1.7 | 36 | hsa-miR-130b-3p | Up | 1.1 |
| 75 | hsa-miR-183-5p | Up | 1.6 | 66 | hsa-miR-15b-5p | Up | 1.3 |
| 33 | hsa-miR-1291 | Up | 1.5 | 151 | hsa-miR-331-5p | Up | 1.3 |
| 82 | hsa-miR-192-5p | Up | 1.4 | 70 | hsa-miR-181a-2-3p | Up | 1.2 |
| 128 | hsa-miR-29b-2-5p | Up | 1.3 | 19 | hsa-miR-10a-3p | Up | 1.3 |
| 32 | hsa-miR-1285-3p | Up | 1.4 | 156 | hsa-miR-338-5p | Up | 1.6 |
| 215 | hsa-miR-576-5p | Up | 1.3 | 31 | hsa-miR-1280 | Up | 1.2 |
| 131 | hsa-miR-29c-5p | Up | 1.2 | 239 | hsa-miR-99a-5p | Up | 1.2 |
| 2 | hsa-let-7b-3p | Up | 1.3 | 134 | hsa-miR-30b-5p | Up | 1.2 |
| 235 | hsa-miR-93-3p | Up | 1.5 | 79 | hsa-miR-18 a-5p | Up | 1.6 |
| 113 | hsa-miR-23a-5p | Up | 1.4 | 120 | hsa-miR-26b-5p | Up | 1.3 |

MiRNAs differentially expressed between normal, cancer-free and Luminal A subtype of breast cancers (Table 6, C vs. LA) but not reported in other literatures (Table 1). Up: upregulated in breast cancer subjects compared to control subjects without breast cancer. Down: downregulated in breast cancer subjects compared to control subjects without breast cancer. FC: fold change.

TABLE 10

Novel miRNAs differentially expressed between cancer-free (normal) and HER2 subtype breast cancer

| SEQ ID NO: | Name | Regulation | FC | SEQ ID NO: | Name | Regulation | FC |
|---|---|---|---|---|---|---|---|
| 179 | hsa-miR-411-3p | Down | 0.6 | 164 | hsa-miR-362-3p | Up | 1.4 |
| 201 | hsa-miR-487b | Down | 0.6 | 84 | hsa-miR-193b-3p | Up | 1.7 |
| 157 | hsa-miR-339-3p | Down | 0.7 | 98 | hsa-miR-206 | Up | 4 |
| 169 | hsa-miR-370 | Down | 0.6 | 237 | hsa-miR-96-5p | Up | 2 |
| 73 | hsa-miR-181d | Down | 0.8 | 47 | hsa-miR-143-3p | Up | 2.1 |
| 62 | hsa-miR-154-5p | Down | 0.5 | 65 | hsa-miR-15b-3p | Up | 1.5 |
| 110 | hsa-miR-224-5p | Down | 0.7 | 212 | hsa-miR-532-5p | Up | 1.7 |
| 173 | hsa-miR-375 | Down | 0.5 | 166 | hsa-miR-363-3p | Up | 1.6 |
| 203 | hsa-miR-493-5p | Down | 0.5 | 20 | hsa-miR-10a-5p | Up | 1.4 |
| 29 | hsa-miR-127-3p | Down | 0.5 | 209 | hsa-miR-502-3p | Up | 1.4 |
| 178 | hsa-miR-409-3p | Down | 0.6 | 130 | hsa-miR-29c-3p | Up | 1.7 |
| 155 | hsa-miR-337-5p | Down | 0.6 | 175 | hsa-miR-378a-3p | Up | 1.7 |
| 146 | hsa-miR-324-5p | Down | 0.7 | 186 | hsa-miR-4306 | Up | 1.4 |
| 148 | hsa-miR-326 | Down | 0.7 | 12 | hsa-miR-1 | Up | 2.7 |
| 150 | hsa-miR-330-3p | Down | 0.8 | 129 | hsa-miR-29b-3p | Up | 1.3 |
| 158 | hsa-miR-339-5p | Down | 0.6 | 100 | hsa-miR-20b-5p | Up | 1.9 |
| 59 | hsa-miR-151a-3p | Down | 0.7 | 68 | hsa-miR-17-3p | Up | 1.3 |
| 216 | hsa-miR-584-5p | Down | 0.8 | 224 | hsa-miR-629-5p | Up | 1.7 |
| 60 | hsa-miR-151a-5p | Down | 0.6 | 171 | hsa-miR-374a-5p | Up | 2.1 |
| 123 | hsa-miR-27b-3p | Down | 0.8 | 228 | hsa-miR-660-5p | Up | 1.7 |
| 92 | hsa-miR-199b-3p | Down | 0.8 | 77 | hsa-miR-186-5p | Up | 1.4 |
| 1 | hsa-let-7a-5p | Down | 0.5 | 13 | hsa-miR-101-3p | Up | 1.8 |
| 168 | hsa-miR-369-5p | Down | 0.5 | 76 | hsa-miR-185-5p | Up | 1.3 |
| 115 | hsa-miR-23c | Down | 0.7 | 93 | hsa-miR-19a-3p | Up | 1.9 |
| 126 | hsa-miR-299-3p | Down | 0.7 | 140 | hsa-miR-320a | Up | 1.3 |
| 188 | hsa-miR-432-5p | Down | 0.5 | 94 | hsa-miR-19b-3p | Up | 1.9 |
| 213 | hsa-miR-551b-3p | Down | 0.6 | 143 | hsa-miR-320d | Up | 1.3 |
| 174 | hsa-miR-376a-5p | Down | 0.6 | 99 | hsa-miR-20a-5p | Up | 1.4 |
| 138 | hsa-miR-30e-3p | Down | 0.8 | 200 | hsa-miR-486-5p | Up | 1.9 |
| 154 | hsa-miR-337-3p | Down | 0.6 | 162 | hsa-miR-34b-5p | Up | 1.7 |
| 125 | hsa-miR-28-5p | Down | 0.6 | 87 | hsa-miR-196a-5p | Up | 1.7 |
| 187 | hsa-miR-431-5p | Down | 0.6 | 223 | hsa-miR-629-3p | Up | 1.4 |
| 41 | hsa-miR-136-5p | Down | 0.5 | 218 | hsa-miR-596 | Up | 2.3 |
| 238 | hsa-miR-98 | Down | 0.6 | 225 | hsa-miR-650 | Up | 2 |
| 18 | hsa-miR-107 | Down | 0.7 | 34 | hsa-miR-1299 | Up | 1.8 |
| 5 | hsa-let-7d-5p | Down | 0.6 | 16 | hsa-miR-106b-3p | Up | 1.2 |
| 51 | hsa-miR-146a-5p | Down | 0.8 | 207 | hsa-miR-500a-5p | Up | 1.8 |
| 52 | hsa-miR-146b-5p | Down | 0.7 | 211 | hsa-miR-532-3p | Up | 1.2 |
| 112 | hsa-miR-23a-3p | Down | 0.6 | 74 | hsa-miR-1825 | Up | 1.6 |

TABLE 10-continued

Novel miRNAs differentially expressed between cancer-free (normal) and HER2 subtype breast cancer

| SEQ ID NO: | Name | Regulation | FC | SEQ ID NO: | Name | Regulation | FC |
|---|---|---|---|---|---|---|---|
| 121 | hsa-miR-27a-3p | Down | 0.8 | 189 | hsa-miR-450a-5p | Up | 1.6 |
| 15 | hsa-miR-103a-3p | Down | 0.8 | 14 | hsa-miR-101-5p | Up | 2.2 |
| 8 | hsa-let-7f-5p | Down | 0.6 | 167 | hsa-miR-365a-3p | Up | 1.9 |
| 106 | hsa-miR-221-5p | Down | 0.7 | 205 | hsa-miR-499a-5p | Up | 2.2 |
| 66 | hsa-miR-15b-5p | Down | 0.8 | 80 | hsa-miR-18b-5p | Up | 1.3 |
| 107 | hsa-miR-222-3p | Down | 0.8 | 43 | hsa-miR-140-3p | Up | 1.9 |
| 11 | hsa-let-7i-5p | Down | 0.8 | 89 | hsa-miR-197-3p | Up | 1.2 |
| 118 | hsa-miR-26a-5p | Down | 0.8 | 17 | hsa-miR-106b-5p | Up | 1.6 |
| 221 | hsa-miR-618 | Up | 2.3 | 48 | hsa-miR-144-3p | Up | 2.6 |
| 219 | hsa-miR-616-3p | Up | 1.6 | 141 | hsa-miR-320b | Up | 1.4 |
| 222 | hsa-miR-627 | Up | 1.5 | 226 | hsa-miR-651 | Up | 1.7 |
| 194 | hsa-miR-4732-3p | Up | 1.9 | 195 | hsa-miR-483-3p | Up | 1.6 |
| 208 | hsa-miR-501-5p | Up | 1.8 | 147 | hsa-miR-32-5p | Up | 1.5 |
| 176 | hsa-miR-378a-5p | Up | 1.6 | 83 | hsa-miR-193a-5p | Up | 1.5 |
| 75 | hsa-miR-183-5p | Up | 1.8 | 230 | hsa-miR-720 | Up | 2 |
| 33 | hsa-miR-1291 | Up | 2 | 54 | hsa-miR-148a-5p | Up | 1.2 |
| 82 | hsa-miR-192-5p | Up | 1.6 | 191 | hsa-miR-452-5p | Up | 1.3 |
| 128 | hsa-miR-29b-2-5p | Up | 1.1 | 7 | hsa-let-7f-1-3p | Up | 1.3 |
| 32 | hsa-miR-1285-3p | Up | 1.5 | 161 | hsa-miR-34a-5p | Up | 1.3 |
| 215 | hsa-miR-576-5p | Up | 1.6 | 45 | hsa-miR-141-3p | Up | 1.4 |
| 131 | hsa-miR-29c-5p | Up | 1.4 | 144 | hsa-miR-320e | Up | 1.5 |
| 3 | hsa-let-7b-3p | Up | 1.3 | 142 | hsa-miR-320c | Up | 1.4 |
| 235 | hsa-miR-93-3p | Up | 1.3 | 116 | hsa-miR-24-3p | Up | 1.2 |
| 113 | hsa-miR-23a-5p | Up | 1.3 | | | | |

MiRNAs differentially expressed between normal, cancer-free, and HER2 subtype of breast cancers (Table 6, C vs. HER) but not reported in other literatures (Table 1). Up: upregulated in breast cancer subjects compared to control subjects without breast cancer. Down: downregulated in breast cancer subjects compared to control subjects without breast cancer. FC: fold change.

TABLE 11

Novel miRNAs differentially expressed between cancer-free (normal) and triple negative subtype breast cancer

| SEQ ID NO: | Name | Regulation | FC | SEQ ID NO: | Name | Regulation | FC |
|---|---|---|---|---|---|---|---|
| 179 | hsa-miR-411-3p | Down | 0.5 | 82 | hsa-miR-192-5p | Up | 1.9 |
| 201 | hsa-miR-487b | Down | 0.4 | 128 | hsa-miR-29b-2-5p | Up | 1.3 |
| 157 | hsa-miR-339-3p | Down | 0.6 | 32 | hsa-miR-1285-3p | Up | 1.7 |
| 169 | hsa-miR-370 | Down | 0.4 | 215 | hsa-miR-576-5p | Up | 2.2 |
| 73 | hsa-miR-181d | Down | 0.6 | 131 | hsa-miR-29c-5p | Up | 1.4 |
| 62 | hsa-miR-154-5p | Down | 0.3 | 2 | hsa-let-7b-3p | Up | 1.3 |
| 110 | hsa-miR-224-5p | Down | 0.7 | 235 | hsa-miR-93-3p | Up | 1.5 |
| 173 | hsa-miR-375 | Down | 0.5 | 113 | hsa-miR-23a-5p | Up | 1.4 |
| 203 | hsa-miR-493-5p | Down | 0.5 | 164 | hsa-miR-362-3p | Up | 1.6 |
| 29 | hsa-miR-127-3p | Down | 0.4 | 84 | hsa-miR-193b-3p | Up | 1.5 |
| 178 | hsa-miR-409-3p | Down | 0.4 | 98 | hsa-miR-206 | Up | 4 |
| 155 | hsa-miR-337-5p | Down | 0.4 | 237 | hsa-miR-96-5p | Up | 2.3 |
| 146 | hsa-miR-324-5p | Down | 0.7 | 47 | hsa-miR-143-3p | Up | 2.5 |
| 148 | hsa-miR-326 | Down | 0.5 | 65 | hsa-miR-15b-3p | Up | 1.9 |
| 150 | hsa-miR-330-3p | Down | 0.6 | 212 | hsa-miR-532-5p | Up | 1.8 |
| 158 | hsa-miR-339-5p | Down | 0.5 | 166 | hsa-miR-363-3p | Up | 2.1 |
| 59 | hsa-miR-151a-3p | Down | 0.7 | 20 | hsa-miR-10a-5p | Up | 1.2 |
| 216 | hsa-miR-584-5p | Down | 0.7 | 209 | hsa-miR-502-3p | Up | 1.6 |
| 60 | hsa-miR-151a-5p | Down | 0.6 | 130 | hsa-miR-29c-3p | Up | 1.9 |
| 123 | hsa-miR-27b-3p | Down | 0.8 | 175 | hsa-miR-378a-3p | Up | 1.6 |
| 92 | hsa-miR-199b-3p | Down | 0.8 | 186 | hsa-miR-4306 | Up | 1.5 |
| 1 | hsa-let-7a-5p | Down | 0.5 | 12 | hsa-miR-1 | Up | 2.2 |
| 24 | hsa-miR-124-5p | Down | 0.8 | 129 | hsa-miR-29b-3p | Up | 1.4 |
| 229 | hsa-miR-668 | Down | 0.5 | 100 | hsa-miR-20b-5p | Up | 2.5 |
| 198 | hsa-miR-485-3p | Down | 0.5 | 68 | hsa-miR-17-3p | Up | 1.4 |
| 168 | hsa-miR-369-5p | Down | 0.5 | 224 | hsa-miR-629-5p | Up | 1.5 |
| 115 | hsa-miR-23c | Down | 0.7 | 171 | hsa-miR-374a-5p | Up | 2.3 |
| 126 | hsa-miR-299-3p | Down | 0.5 | 228 | hsa-miR-660-5p | Up | 1.8 |
| 40 | hsa-miR-136-3p | Down | 0.6 | 77 | hsa-miR-186-5p | Up | 1.3 |
| 188 | hsa-miR-432-5p | Down | 0.4 | 13 | hsa-miR-101-3p | Up | 2 |
| 213 | hsa-miR-551b-3p | Down | 0.5 | 76 | hsa-miR-185-5p | Up | 1.2 |
| 174 | hsa-miR-376a-5p | Down | 0.5 | 93 | hsa-miR-19a-3p | Up | 2.1 |

TABLE 11-continued

Novel miRNAs differentially expressed between cancer-free (normal) and triple negative subtype breast cancer

| SEQ ID NO: | Name | Regulation | FC | SEQ ID NO: | Name | Regulation | FC |
|---|---|---|---|---|---|---|---|
| 138 | hsa-miR-30e-3p | Down | 0.8 | 140 | hsa-miR-320a | Up | 1.3 |
| 154 | hsa-miR-337-3p | Down | 0.5 | 94 | hsa-miR-19b-3p | Up | 2.3 |
| 136 | hsa-miR-30d-3p | Down | 0.8 | 143 | hsa-miR-320d | Up | 1.3 |
| 125 | hsa-miR-28-5p | Down | 0.6 | 99 | hsa-miR-20a-5p | Up | 1.8 |
| 187 | hsa-miR-431-5p | Down | 0.4 | 200 | hsa-miR-486-5p | Up | 2 |
| 41 | hsa-miR-136-5p | Down | 0.4 | 162 | hsa-miR-34b-5p | Up | 1.8 |
| 238 | hsa-miR-98 | Down | 0.5 | 220 | hsa-miR-616-5p | Up | 1.7 |
| 18 | hsa-miR-107 | Down | 0.8 | 87 | hsa-miR-196a-5p | Up | 2.1 |
| 5 | hsa-let-7d-5p | Down | 0.5 | 223 | hsa-miR-629-3p | Up | 1.4 |
| 51 | hsa-miR-146a-5p | Down | 0.7 | 218 | hsa-miR-596 | Up | 1.5 |
| 52 | hsa-miR-146b-5p | Down | 0.6 | 206 | hsa-miR-500a-3p | Up | 1.4 |
| 112 | hsa-miR-23a-3p | Down | 0.6 | 207 | hsa-miR-500a-5p | Up | 2.2 |
| 121 | hsa-miR-27a-3p | Down | 0.7 | 189 | hsa-miR-450a-5p | Up | 1.6 |
| 105 | hsa-miR-221-3p | Down | 0.8 | 14 | hsa-miR-101-5p | Up | 1.8 |
| 15 | hsa-miR-103a-3p | Down | 0.8 | 167 | hsa-miR-365a-3p | Up | 2.1 |
| 8 | hsa-let-7f-5p | Down | 0.5 | 205 | hsa-miR-499a-5p | Up | 1.6 |
| 199 | hsa-miR-485-5p | Down | 0.5 | 49 | hsa-miR-144-5p | Up | 1.8 |
| 106 | hsa-miR-221-5p | Down | 0.8 | 80 | hsa-miR-18b-5p | Up | 1.4 |
| 177 | hsa-miR-382-5p | Down | 0.4 | 43 | hsa-miR-140-3p | Up | 2.2 |
| 149 | hsa-miR-328 | Down | 0.8 | 17 | hsa-miR-106b-5p | Up | 1.9 |
| 241 | hsa-miR-99b-5p | Down | 0.7 | 109 | hsa-miR-22-3p | Up | 1.4 |
| 240 | hsa-miR-99b-3p | Down | 0.8 | 48 | hsa-miR-144-3p | Up | 2.9 |
| 81 | hsa-miR-191-5p | Down | 0.9 | 3 | hsa-let-7b-5p | Up | 1.6 |
| 221 | hsa-miR-618 | Up | 2.4 | 141 | hsa-miR-320b | Up | 1.2 |
| 220 | hsa-miR-616-3p | Up | 1.4 | 69 | hsa-miR-17-5p | Up | 1.7 |
| 222 | hsa-miR-627 | Up | 1.6 | 193 | hsa-miR-454-5p | Up | 1.5 |
| 194 | hsa-miR-4732-3p | Up | 1.9 | 231 | hsa-miR-874 | Up | 1.5 |
| 208 | hsa-miR-501-5p | Up | 2.2 | 44 | hsa-miR-140-5p | Up | 1.2 |
| 176 | hsa-miR-378a-5p | Up | 2 | 192 | hsa-miR-454-3p | Up | 1.3 |
| 75 | hsa-miR-183-5p | Up | 2.5 | 139 | hsa-miR-30e-5p | Up | 1.3 |
| 33 | hsa-miR-1291 | Up | 2 | | | | |

MiRNAs differentially expressed between normal (cancer-free) and triple negative subtype of breast cancers (Table 6, C vs. TN) but not reported in other literatures (Table 1). Up: upregulated in breast cancer subjects compared to control subjects without breast cancer. Down: downregulated in breast cancer subjects compared to control subjects without breast cancer. FC: fold change.

TABLE 12

Novel miRNAs differentially expressed between normal and breast cancer

| SEQ ID NO: | Name | Regulation | FC | SEQ ID NO: | Name | Regulation | FC |
|---|---|---|---|---|---|---|---|
| 179 | hsa-miR-411-3p | Down | 0.7 | 164 | hsa-miR-362-3p | Up | 1.5 |
| 201 | hsa-miR-487b | Down | 0.5 | 84 | hsa-miR-193b-3p | Up | 1.6 |
| 157 | hsa-miR-339-3p | Down | 0.7 | 98 | hsa-miR-206 | Up | 2.9 |
| 169 | hsa-miR-370 | Down | 0.6 | 237 | hsa-miR-96-5p | Up | 1.5 |
| 73 | hsa-miR-181d | Down | 0.6 | 47 | hsa-miR-143-3p | Up | 1.9 |
| 62 | hsa-miR-154-5p | Down | 0.6 | 65 | hsa-miR-15b-3p | Up | 1.3 |
| 110 | hsa-miR-224-5p | Down | 0.7 | 212 | hsa-miR-532-5p | Up | 1.3 |
| 173 | hsa-miR-375 | Down | 0.5 | 166 | hsa-miR-363-3p | Up | 1.8 |
| 203 | hsa-miR-493-5p | Down | 0.7 | 20 | hsa-miR-10a-5p | Up | 1.2 |
| 29 | hsa-miR-127-3p | Down | 0.7 | 209 | hsa-miR-502-3p | Up | 1.9 |
| 178 | hsa-miR-409-3p | Down | 0.2 | 130 | hsa-miR-29c-3p | Up | 1.4 |
| 155 | hsa-miR-337-5p | Down | 0.6 | 175 | hsa-miR-378a-3p | Up | 1.5 |
| 146 | hsa-miR-324-5p | Down | 0.7 | 186 | hsa-miR-4306 | Up | 1.5 |
| 148 | hsa-miR-326 | Down | 0.6 | 12 | hsa-miR-1 | Up | 2.4 |
| 150 | hsa-miR-330-3p | Down | 0.8 | 129 | hsa-miR-29b-3p | Up | 1.3 |
| 158 | hsa-miR-339-5p | Down | 0.8 | 100 | hsa-miR-20b-5p | Up | 1.8 |
| 59 | hsa-miR-151a-3p | Down | 0.8 | 68 | hsa-miR-17-3p | Up | 1.6 |
| 216 | hsa-miR-584-5p | Down | 0.8 | 224 | hsa-miR-629-5p | Up | 1.4 |
| 171 | hsa-miR-374a-5p | Down | 0.7 | 228 | hsa-miR-660-5p | Up | 1.6 |
| 60 | hsa-miR-151a-5p | Down | 0.7 | 77 | hsa-miR-186-5p | Up | 1.5 |
| 123 | hsa-miR-27b-3p | Down | 0.8 | 13 | hsa-miR-101-3p | Up | 2.7 |
| 92 | hsa-miR-199b-3p | Down | 0.8 | 76 | hsa-miR-185-5p | Up | 1.4 |
| 1 | hsa-let-7a-5p | Down | 0.8 | 93 | hsa-miR-19a-3p | Up | 1.3 |
| 24 | hsa-miR-124-5p | Down | 0.6 | 140 | hsa-miR-320a | Up | 1.4 |
| 229 | hsa-miR-668 | Down | 0.6 | 94 | hsa-miR-19b-3p | Up | 1.4 |
| 198 | hsa-miR-485-3p | Down | 0.6 | 143 | hsa-miR-320d | Up | 1.2 |
| 40 | hsa-miR-136-3p | Down | 0.6 | 99 | hsa-miR-20a-5p | Up | 1.3 |

TABLE 12-continued

Novel miRNAs differentially expressed between normal and breast cancer

| SEQ ID NO: | Name | Regulation | FC | SEQ ID NO: | Name | Regulation | FC |
|---|---|---|---|---|---|---|---|
| 136 | hsa-miR-30d-3p | Down | 0.6 | 200 | hsa-miR-486-5p | Up | 1.8 |
| 105 | hsa-miR-221-3p | Down | 0.8 | 220 | hsa-miR-616-5p | Up | 1.4 |
| 23 | hsa-miR-1226-3p | Down | 0.6 | 206 | hsa-miR-500a-3p | Up | 2.2 |
| 226 | hsa-miR-651 | Down | 0.5 | 225 | hsa-miR-650 | Up | 1.6 |
| 160 | hsa-miR-342-5p | Down | 0.5 | 34 | hsa-miR-1299 | Up | 1.6 |
| 96 | hsa-miR-200c-3p | Down | 0.7 | 16 | hsa-miR-106b-3p | Up | 1.2 |
| 124 | hsa-miR-28-3p | Down | 0.8 | 211 | hsa-miR-532-3p | Up | 1.2 |
| 183 | hsa-miR-425-3p | Down | 0.9 | 74 | hsa-miR-1825 | Up | 1.7 |
| 90 | hsa-miR-199a-3p | Down | 0.8 | 49 | hsa-miR-144-5p | Up | 1.4 |
| 152 | hsa-miR-335-3p | Down | 0.7 | 89 | hsa-miR-197-3p | Up | 1.4 |
| 37 | hsa-miR-130b-5p | Down | 0.9 | 109 | hsa-miR-22-3p | Up | 1.2 |
| 104 | hsa-miR-219-5p | Down | 0.8 | 3 | hsa-let-7b-5p | Up | 1.5 |
| 232 | hsa-miR-885-5p | Down | 0.6 | 69 | hsa-miR-17-5p | Up | 1.4 |
| 137 | hsa-miR-30d-5p | Down | 0.9 | 214 | hsa-miR-573 | Up | 2.2 |
| 35 | hsa-miR-130a-3p | Down | 0.8 | 165 | hsa-miR-362-5p | Up | 1.3 |
| 221 | hsa-miR-618 | Up | 1.8 | 182 | hsa-miR-424-5p | Up | 1.6 |
| 219 | hsa-miR-616-3p | Up | 1.3 | 172 | hsa-miR-374b-5p | Up | 2 |
| 222 | hsa-miR-627 | Up | 1.6 | 163 | hsa-miR-361-5p | Up | 1.3 |
| 194 | hsa-miR-4732-3p | Up | 1.5 | 53 | hsa-miR-148a-3p | Up | 1.4 |
| 208 | hsa-miR-501-5p | Up | 1.7 | 36 | hsa-miR-130b-3p | Up | 1.1 |
| 176 | hsa-miR-378a-5p | Up | 1.7 | 66 | hsa-miR-15b-5p | Up | 1.3 |
| 75 | hsa-miR-183-5p | Up | 1.6 | 151 | hsa-miR-331-5p | Up | 1.3 |
| 33 | hsa-miR-1291 | Up | 1.5 | 70 | hsa-miR-181a-2-3p | Up | 1.2 |
| 82 | hsa-miR-192-5p | Up | 1.4 | 19 | hsa-miR-10a-3p | Up | 1.3 |
| 128 | hsa-miR-29b-2-5p | Up | 1.3 | 156 | hsa-miR-338-5p | Up | 1.6 |
| 32 | hsa-miR-1285-3p | Up | 1.4 | 31 | hsa-miR-1280 | Up | 1.2 |
| 215 | hsa-miR-576-5p | Up | 1.3 | 239 | hsa-miR-99a-5p | Up | 1.2 |
| 131 | hsa-miR-29c-5p | Up | 1.2 | 134 | hsa-miR-30b-5p | Up | 1.2 |
| 2 | hsa-let-7b-3p | Up | 1.3 | 79 | hsa-miR-18a-5p | Up | 1.6 |
| 235 | hsa-miR-93-3p | Up | 1.5 | 120 | hsa-miR-26b-5p | Up | 1.3 |
| 113 | hsa-miR-23a-5p | Up | 1.4 | | | | |

MiRNAs differentially expressed between normal and breast cancers (regardless of subtypes) (Table 6, C vs. ALL BC) but not reported in other literatures (Table 1). Up: upregulated in breast cancer subjects compared to control subjects without breast cancer. Down: downregulated in breast cancer subjects compared to control subjects without breast cancer. FC: fold change.

TABLE 13

Novel miRNAs differentially expressed between normal and all three subtypes of breast cancer

| Name | SEQ ID NO: |
|---|---|
| hsa-let-7a-5p | 1 |
| hsa-let-7b-3p | 2 |
| hsa-miR-1 | 12 |
| hsa-miR-101-3p | 13 |
| hsa-miR-10a-5p | 20 |
| hsa-miR-127-3p | 29 |
| hsa-miR-1285-3p | 32 |
| hsa-miR-1291 | 33 |
| hsa-miR-143-3p | 47 |
| hsa-miR-151a-3p | 59 |
| hsa-miR-151a-5p | 60 |
| hsa-miR-154-5p | 62 |
| hsa-miR-15b-3p | 65 |
| hsa-miR-17-3p | 68 |
| hsa-miR-181d | 73 |
| hsa-miR-183-5p | 75 |
| hsa-miR-185-5p | 76 |
| hsa-miR-186-5p | 77 |
| hsa-miR-192-5p | 82 |
| hsa-miR-193b-3p | 84 |
| hsa-miR-199b-3p | 92 |
| hsa-miR-19a-3p | 93 |
| hsa-miR-19b-3p | 94 |
| hsa-miR-206 | 98 |
| hsa-miR-20a-5p | 99 |
| hsa-miR-20b-5p | 100 |
| hsa-miR-224-5p | 110 |
| hsa-miR-23a-5p | 113 |
| hsa-miR-27b-3p | 123 |
| hsa-miR-29b-2-5p | 128 |
| hsa-miR-29b-3p | 129 |
| hsa-miR-29c-3p | 130 |
| hsa-miR-29c-5p | 131 |
| hsa-miR-320a | 140 |
| hsa-miR-320d | 143 |
| hsa-miR-324-5p | 146 |
| hsa-miR-326 | 148 |
| hsa-miR-330-3p | 150 |
| hsa-miR-337-5p | 155 |
| hsa-miR-339-3p | 157 |
| hsa-miR-339-5p | 158 |
| hsa-miR-362-3p | 164 |
| hsa-miR-363-3p | 166 |
| hsa-miR-370 | 169 |
| hsa-miR-374a-5p | 171 |
| hsa-miR-375 | 173 |
| hsa-miR-378a-3p | 175 |
| hsa-miR-378a-5p | 176 |
| hsa-miR-409-3p | 178 |
| hsa-miR-411-3p | 179 |
| hsa-miR-4306 | 186 |
| hsa-miR-4732-3p | 194 |
| hsa-miR-486-5p | 200 |
| hsa-miR-487b | 201 |
| hsa-miR-493-5p | 203 |

TABLE 13-continued

Novel miRNAs differentially expressed between normal and all three subtypes of breast cancer

| Name | SEQ ID NO: |
|---|---|
| hsa-miR-501-5p | 208 |
| hsa-miR-502-3p | 209 |
| hsa-miR-532-5p | 212 |
| hsa-miR-576-5p | 215 |
| hsa-miR-584-5p | 216 |
| hsa-miR-616-3p | 219 |
| hsa-miR-618 | 221 |
| hsa-miR-627 | 222 |
| hsa-miR-629-5p | 224 |
| hsa-miR-660-5p | 228 |
| hsa-miR-93-3p | 235 |
| hsa-miR-96-5p | 237 |

Sixty seven novel miRNAs differentially expressed between normal and all three subtypes (Luminal A, HER2 and triple negative) of breast cancer (Table 6, the overlap of C vs. LA, C vs. HER, C vs. TN) but not reported in other literatures (Table 1).

TABLE 14

Novel miRNAs for multi-variant biomarker panel for breast cancer detection

| | SEQ ID NO: |
|---|---|
| Significant miRNAs | |
| hsa-miR-409-3p | 178 |
| hsa-miR-382-5p | 177 |
| hsa-miR-375 | 173 |
| hsa-miR-23a-3p | 112 |
| hsa-miR-124-5p | 24 |
| hsa-miR-378a-5p | 176 |
| hsa-miR-140-5p | 44 |
| hsa-miR-485-5p | 199 |
| hsa-miR-23c | 115 |
| hsa-miR-1291 | 33 |
| hsa-miR-324-5p | 146 |
| hsa-miR-500a-3p | 206 |
| hsa-miR-374a-5p | 171 |
| hsa-miR-485-3p | 198 |
| hsa-miR-143-3p | 47 |
| hsa-miR-551b-3p | 213 |
| hsa-miR-186-5p | 77 |
| hsa-miR-339-3p | 157 |
| hsa-miR-193b-3p | 84 |
| hsa-miR-616-3p | 219 |
| hsa-miR-320d | 143 |
| hsa-miR-15b-5p | 66 |
| hsa-miR-32-5p | 147 |
| hsa-miR-191-5p | 81 |
| hsa-let-7b-5p | 3 |
| hsa-let-7a-5p | 1 |
| hsa-miR-885-5p | 232 |
| hsa-miR-127-3p | 29 |
| hsa-miR-320e | 144 |
| hsa-miR-299-3p | 126 |
| hsa-miR-1285-3p | 32 |
| hsa-miR-337-3p | 154 |
| hsa-miR-181d | 73 |
| hsa-miR-140-3p | 43 |
| Insignificant miRNAs | |
| hsa-miR-122-5p | 22 |
| hsa-miR-200b-3p | 95 |
| hsa-miR-139-5p | 42 |
| hsa-miR-150-5p | 57 |
| hsa-miR-652-3p | 227 |
| hsa-miR-126-3p | 27 |
| hsa-miR-135a-5p | 39 |

The list of miRNAs frequently selected for multi-variant biomarker panel breast cancer detection (Table 8) but not reported in other literatures (Table 1). The expression level of the miRNAs were either altered in the breast cancer subjects (Significant miRNAs) or not altered in the breast cancer subjects (Insignificant miRNAs).

Multi-variant biomarker panel search:

38 of the frequently selected novel miRNAs were associated with breast cancer, whereby the expression levels of these miRNAs were found to be different in cancer patients compared to normal, cancer-free subjects (Table 14, Significant miRNAs).

Methods

Pre-analytics (sample collection and microRNA extraction): Serum samples from normal, cancer-free and breast cancer subjects were purchased from the commercial biobank Asterand and stored frozen at −80° C. prior to use. Total RNA from 200 µl of each serum sample was isolated using the well-established TRI Reagent following manufacture's protocol. As serum contains minute amounts of RNA, rationally designed isolation enhancers (MS2) and spike-in control RNAs (MiRXES) were added to the specimen prior to isolation to reduce the loss of RNA and monitor extraction efficiency,.

Real-time quantitative polymerase chain reaction (RT-qPCR): The isolated total RNA and synthetic RNA standards were converted to cDNA in optimized multiplex reverse transcription reactions, with a second set of spike-in control RNAs used to detect the presence of inhibitors and to monitor the efficiency of the polymerase chain reaction. Improm II reverse transcriptase was used to perform the reverse transcription following manufacture's instruction. The synthesized cDNA was then subjected to a multiplex augmentation step and quantified using a Sybr Green based single-plex qPCR assays (MIQE compliant; MiRXES). A ViiA 7 384 Real-Time PCR System or CFX384 Touch Real-Time PCR Detection System was used for real-time quantitative polymerase chain reaction reactions (RT-qPCR). The overview and details of miRNA RT-qPCR measurement workflow was summarized in FIG. 2.

Data processing: The raw Cycles to Threshold (Ct) values were processed and the absolute copy numbers of the target miRNAs in each sample were determined by inter-/extrapolation of the synthetic miRNA standard curves. The technical variations introduced during RNA isolation and the processes of RT-qPCR were normalized by the spike-in control RNAs. For the analysis of single miRNAs, biological variations were further normalized by a set of validated endogenous reference miRNAs stably expressed across all control and disease samples.

LIST OF REFERENCES AS DISCLOSED IN TABLE 1

1. Garcia M, J. A., Ward E M, Center M M, Hao Y, Siegel R L et al, Global Cancer Facts & Figures 2007. American Cancer Society, Atlanta, GA, 2007.
2. Humphrey, L. L., et al., Breast cancer screening: a summary of the evidence for the U.S. Preventive Services Task Force. Ann Intern Med, 2002. 137(5 Part 1): p. 347-60.
3. Force, U.S.P.S.T., Screening for breast cancer: U.S. Preventive Services Task Force recommendation statement. Ann Intern Med, 2009. 151(10): p. 716-26, W-236.
4. Nelson, H. D., et al., Screening for breast cancer: an update for the U.S. Preventive Services Task Force. Ann Intern Med, 2009. 151(10): p. 727-37, W237-42.

5. Tosteson, A. N., et al., Consequences of false-positive screening mammograms. JAMA Intern Med, 2014. 174(6): p. 954-61.

6. Molina, R., et al., Tumor markers in breast cancer-European Group on Tumor Markers recommendations. Tumour Biol, 2005. 26(6): p. 281-93.

7. Liang, H., et al., The origin, function, and diagnostic potential of extracellular microRNAs in human body fluids. Wiley Interdiscip Rev RNA, 2014. 5(2): p. 285-300.

8. Cortez, M. A., et al., MicroRNAs in body fluids—the mix of hormones and biomarkers. Nat Rev Clin Oncol, 2011. 8(8): p. 467-77.

9. Lee, R. C., R. L. Feinbaum, and V. Ambros, The C. elegans heterochronic gene lin-4 encodes small RNAs with antisense complementarity to lin-14. Cell, 1993. 75(5): p. 843-54.

10. Friedman, R. C., et al., Most mammalian mRNAs are conserved targets of microRNAs. Genome Res, 2009. 19(1): p. 92-105.

11. Hayashita, Y., et al., A polycistronic microRNA cluster, miR-17-92, is overexpressed in human lung cancers and enhances cell proliferation. Cancer Res, 2005. 65(21): p. 9628-32.

12. Jovanovic, M. and M. O. Hengartner, miRNAs and apoptosis: RNAs to die for. Oncogene, 2006. 25(46): p. 6176-87.

13. Wu, H.-H., W.-C. Lin, and K.-W. Tsai, Advances in molecular biomarkers for gastric cancer: miRNAs as emerging novel cancer markers. Expert reviews in molecular medicine, 2014. 16.

14. Tong, F., et al., MicroRNAs in gastric cancer: from benchtop to bedside. Digestive diseases and sciences, 2014. 59(1): p. 24-30.

15. Ganepola, G. A., et al., Novel blood-based microRNA biomarker panel for early diagnosis of pancreatic cancer. World J Gastrointest Oncol, 2014. 6(1): p. 22-33.

16. Kosaka, N., H. Iguchi, and T. Ochiya, Circulating microRNA in body fluid: a new potential biomarker for cancer diagnosis and prognosis. Cancer Sci, 2010. 101(10): p. 2087-92.

17. Redova, M., J. Sana, and O. Slaby, Circulating miRNAs as new blood-based biomarkers for solid cancers. Future Oncol, 2013. 9(3): p. 387-402.

18. Jarry, J., et al., The validity of circulating microRNAs in oncology: Five years of challenges and contradictions. Mol Oncol, 2014.

19. Leidner, R. S., L. Li, and C. L. Thompson, Dampening enthusiasm for circulating microRNA in breast cancer. PLoS One, 2013. 8(3): p. e57841.

20. Mestdagh, P., et al., Evaluation of quantitative miRNA expression platforms in the microRNA quality control (miRQC) study. Nat Methods, 2014.

21. Friel, A. M., et al., Relevance of circulating tumor cells, extracellular nucleic acids, and exosomes in breast cancer. Breast Cancer Res Treat, 2010. 123(3): p. 613-25.

22. Mabert, K., et al., Cancer biomarker discovery: current status and future perspectives. Int J Radiat Biol, 2014.

23. Gong, H., et al., Characterization of photosystem II in salt-stressed cyanobacterial Spirulina platensis cells. Biochim Biophys Acta, 2008. 1777(6): p. 488-95.

24. Cissell, K. A. and S. K. Deo, Trends in microRNA detection. Anal Bioanal Chem, 2009. 394(4): p. 1109-16.

25. Tsongalis, G. J., et al., MicroRNA analysis: is it ready for prime time? Clin Chem, 2013. 59(2): p. 343-7.

26. Hindson, B. J., et al., High-throughput droplet digital PCR system for absolute quantitation of DNA copy number. Anal Chem, 2011. 83(22): p. 8604-10.

27. Etheridge, A., et al., Extracellular microRNA: a new source of biomarkers. Mutat Res, 2011. 717(1-2): p. 85-90.

28. Li, Y. and K.V. Kowdley, Method for microRNA isolation from clinical serum samples. Anal Biochem, 2012. 431(1): p. 69-75.

29. Kodahl, A. R., et al., Novel circulating microRNA signature as a potential non-invasive multi-marker test in ER-positive early-stage breast cancer: A case control study. Mol Oncol, 2014.

30. Waters, P. S., et al., Impact of tumour epithelial subtype on circulating microRNAs in breast cancer patients. PLoS One, 2014. 9(3): p. e90605.

31. Si, H., et al., Circulating microRNA-92a and microRNA-21 as novel minimally invasive biomarkers for primary breast cancer. J Cancer Res Clin Oncol, 2013. 139(2): p. 223-9.

32. Mar-Aguilar, F., et al., Serum circulating microRNA profiling for identification of potential breast cancer biomarkers. Dis Markers, 2013. 34(3): p. 163-9.

33. Wang, P. Y., et al., Higher expression of circulating miR-182 as a novel biomarker for breast cancer. Oncol Lett, 2013. 6(6): p. 1681-1686.

34. Kumar, S., et al., Overexpression of circulating miRNA-21 and miRNA-146a in plasma samples of breast cancer patients. Indian J Biochem Biophys, 2013. 50(3): p. 210-4.

35. Chan, M., et al., Identification of circulating microRNA signatures for breast cancer detection. Clin Cancer Res, 2013. 19(16): p. 4477-87.

36. Zeng, R. C., et al., Down-regulation of miRNA-30a in human plasma is a novel marker for breast cancer. Med Oncol, 2013. 30(1): p. 477.

37. Cuk, K., et al., Circulating microRNAs in plasma as early detection markers for breast cancer. Int J Cancer, 2013. 132(7): p. 1602-12.

38. Ng, E. K., et al., Circulating microRNAs as specific biomarkers for breast cancer detection. PLoS One, 2013. 8(1): p. e53141.

39. Eichelser, C., et al., Deregulated serum concentrations of circulating cell-free microRNAs miR-17, miR-34a, miR-155, and miR-373 in human breast cancer development and progression. Clin Chem, 2013. 59(10): p. 1489-96.

40. Liu, J., et al., Analysis of miR-205 and miR-155 expression in the blood of breast cancer patients. Chin J Cancer Res, 2013. 25(1): p. 46-54.

41. Khan, S., et al., miR-379 regulates cyclin B1 expression and is decreased in breast cancer. PLoS One, 2013. 8(7): p. e68753.

42. Cuk, K., et al., Plasma microRNA panel for minimally invasive detection of breast cancer. PLoS One, 2013. 8(10): p. e76729.

43. Sun, Y., et al., Serum microRNA-155 as a potential biomarker to track disease in breast cancer. PLoS One, 2012. 7(10): p. e47003.

44. Alshatwi, A. A., et al., Differential expression profile and genetic variants of microRNAs sequences in breast cancer patients. PLoS One, 2012. 7(2): p. e30049.

45. Schrauder, M. G., et al., Circulating micro-RNAs as potential blood-based markers for early stage breast cancer detection. PLoS One, 2012. 7(1): p. e29770.

46. Schwarzenbach, H., et al., Diagnostic potential of PTEN-targeting miR-214 in the blood of breast cancer patients. Breast Cancer Res Treat, 2012. 134(3): p. 933-41.

47. van Schooneveld, E., et al., Expression profiling of cancerous and normal breast tissues identifies microRNAs that are differentially expressed in serum from patients with (metastatic) breast cancer and healthy volunteers. Breast Cancer Res, 2012. 14(1): p. R34.

48. Guo, L. J. and Q. Y. Zhang, Decreased serum miR-181a is a potential new tool for breast cancer screening. Int J Mol Med, 2012. 30(3): p. 680-6.

49. Wu, Q., et al., Analysis of serum genome-wide microRNAs for breast cancer detection. Clin Chim Acta, 2012. 413(13-14): p. 1058-65.

50. Hu, Z., et al., Serum microRNA profiling and breast cancer risk: the use of miR-484/191 as endogenous controls. Carcinogenesis, 2012. 33(4): p. 828-34.

51. Wu, Q., et al., Next-generation sequencing of microRNAs for breast cancer detection. J Biomed Biotechnol, 2011. 2011: p. 597145.

52. Asaga, S., et al., Direct serum assay for microRNA-21 concentrations in early and advanced breast cancer. Clin Chem, 2011. 57(1): p. 84-91.

53. Roth, C., et al., Circulating microRNAs as blood-based markers for patients with primary and metastatic breast cancer. Breast Cancer Res, 2010. 12(6): p. R90.

54. Zhao, H., et al., A pilot study of circulating miRNAs as potential biomarkers of early stage breast cancer. PLoS One, 2010. 5(10): p. e13735.

55. Heneghan, H. M., et al., Circulating microRNAs as novel minimally invasive biomarkers for breast cancer. Ann Surg, 2010. 251(3): p. 499-505.

56. Heneghan, H. M., et al., Systemic miRNA-195 differentiates breast cancer from other malignancies and is a potential biomarker for detecting noninvasive and early stage disease. Oncologist, 2010. 15(7): p. 673-82.

57. Wang, F., et al., Correlation and quantitation of microRNA aberrant expression in tissues and sera from patients with breast tumor. Gynecol Oncol, 2010. 119(3): p. 586-93.

58. Benjamini, Y. a. H., Y., Controlling the False Discovery Rate: A Practical and Powerful Approach to Multiple Testing. 1995. 57(289-300).

59. Goldhirsch, A., et al., Strategies for subtypes—dealing with the diversity of breast cancer: highlights of the St. Gallen International Expert Consensus on the Primary Therapy of Early Breast Cancer 2011. Ann Oncol, 2011. 22(8): p. 1736-47.

60. Xiong, M., X. Fang, and J. Zhao, Biomarker identification by feature wrappers. Genome Res, 2001. 11(11): p. 1878-87.

61. Saeys, Y., I. Inza, and P. Larranaga, A review of feature selection techniques in bioinformatics. Bioinformatics, 2007. 23(19): p. 2507-17.

What is claimed is:

1. A method of diagnosing a subject as having breast cancer or as being at a risk of developing breast cancer and treating the subject diagnosed as having breast cancer or as being at a risk of developing breast cancer, the method comprising:
   detecting the expression levels of hsa-miR-382-5p (SEQ ID NO: 177), hsa-miR-409-3p (SEQ ID NO: 178) and hsa-miR-375 (SEQ ID NO: 173) in a bodily fluid sample obtained from the subject and
   comparing the expression levels of the same to the expression levels of the same three microRNAs (miRNAs) of a control, wherein hsa-miR-409-3p (SEQ ID NO: 178), hsa-miR-375 (SEQ ID NO: 173) and hsa-miR-382-5p (SEQ ID NO: 177) are downregulated relative to expression levels of the same of the control, wherein said downregulation diagnoses the subject as having breast cancer or as being at a risk of developing breast cancer, and
   treating the subject diagnosed as having breast cancer or as being at a risk of developing breast cancer with an anti-breast cancer compound,
   wherein the control is a bodily fluid sample obtained from a breast cancer-free subject.

2. The method of claim 1, wherein said downregulation is indicative of the subject having any one of the breast cancer subtypes selected from the group consisting of luminal A breast cancer subtype, Her2 overexpression (HER) breast cancer subtype and triple negative (TN or basal) breast cancer subtype.

3. A method of diagnosing a subject as having breast cancer or as being at a risk of developing breast cancer and treating the subject diagnosed as having breast cancer or as being at a risk of developing breast cancer, the method comprising:
   i) detecting the presence of miRNA in a bodily fluid sample obtained from the subject;
   ii) measuring the expression level of at least three miRNA in the bodily fluid sample; and
   iii) using a cancer risk score based on the expression level of the miRNAs measured previously to diagnose the subject as having breast cancer or as being at a risk of developing breast cancer, wherein the at least three miRNA are hsa-miR-409-3p (SEQ ID NO: 178), hsa-miR-382-5p (SEQ ID NO: 177), and hsa-miR-375 (SEQ ID NO: 173), and wherein hsa-miR-409-3p (SEQ ID NO: 178), hsa-miR-382-5p (SEQ ID NO: 177), and hsa-miR-375 (SEQ ID NO: 173) are downregulated as compared to expression levels of the same of a control, and treating the subject diagnosed as having breast cancer or as being at a risk of developing breast cancer with an anti-breast cancer compound,
   wherein the control for comparing the expression level of the at least three miRNA is a bodily fluid sample obtained from a breast cancer-free subject;
   wherein the cancer risk score is a sum of 50 and sum of $K_i$, from i=1 to 12, multiplied with a value of log transformed copy numbers (copy/ml of plasma) of individual miRNAs', wherein $K_i$ is the coefficients used to weight multiple miRNA targets.

4. The method of claim 3, wherein the expression level of the miRNAs is any one of concentration, log (concentration), Ct/Cq number, two to the power of Ct/Cq number.

5. The method of claim 3, wherein the breast cancer is an early stage breast cancer.

6. The method of claim 3, wherein the bodily fluid is selected from the group consisting of cellular and non-cellular components of amniotic fluid, breast milk, bronchial lavage, cerebrospinal fluid, colostrum, interstitial fluid, peritoneal fluids, pleural fluid, saliva, seminal fluid, urine, tears, whole blood, plasma, red blood cells, white blood cells and serum.

7. The method of claim 3, wherein the method further comprises measuring the expression level of at least one further miRNA, which, when compared to the expression level of the same of a control, the expression level is not altered in the subject.

8. The method of claim 7, wherein the at least one further miRNA is hsa-miR-122-5p.

* * * * *